United States Patent
Greene Nguyen et al.

(10) Patent No.: US 12,252,712 B2
(45) Date of Patent: Mar. 18, 2025

(54) USE OF ENGINEERED LIVER TISSUE CONSTRUCTS FOR MODELING LIVER DISORDERS

(71) Applicants: Deborah Lynn Greene Nguyen, San Diego, CA (US); Dwayne E. Carter, San Diego, CA (US); Rhiannon Hardwick, San Diego, CA (US); Alice Chen Walters, San Diego, CA (US); Sharon C. Presnell, Poway, CA (US); Chirag B. Khatiwala, San Diego, CA (US); Rami Nasrallah, San Diego, CA (US)

(72) Inventors: Deborah Lynn Greene Nguyen, San Diego, CA (US); Dwayne E. Carter, San Diego, CA (US); Rhiannon Hardwick, San Diego, CA (US); Alice Chen Walters, San Diego, CA (US); Sharon C. Presnell, Poway, CA (US); Chirag B. Khatiwala, San Diego, CA (US); Rami Nasrallah, San Diego, CA (US)

(73) Assignee: Organovo, Inc., San Diego, CA (US)

( * ) Notice: Subject to any disclaimer, the term of this patent is extended or adjusted under 35 U.S.C. 154(b) by 819 days.

(21) Appl. No.: 16/500,521

(22) PCT Filed: Apr. 3, 2018

(86) PCT No.: PCT/US2018/025960
§ 371 (c)(1),
(2) Date: Oct. 3, 2019

(87) PCT Pub. No.: WO2018/187380
PCT Pub. Date: Oct. 11, 2018

(65) Prior Publication Data
US 2020/0115682 A1    Apr. 16, 2020

Related U.S. Application Data

(60) Provisional application No. 62/480,961, filed on Apr. 3, 2017.

(51) Int. Cl.
| | |
|---|---|
| *C12N 5/071* | (2010.01) |
| *G01N 33/50* | (2006.01) |
| *G01N 33/68* | (2006.01) |
| *G09B 23/30* | (2006.01) |

(52) U.S. Cl.
CPC ....... *C12N 5/0671* (2013.01); *G01N 33/5082* (2013.01); *G01N 33/6893* (2013.01); *G09B 23/306* (2013.01); *C12N 2502/1157* (2013.01); *C12N 2502/1305* (2013.01); *C12N 2502/14* (2013.01); *C12N 2503/04* (2013.01); *C12N 2513/00* (2013.01); *C12N 2533/00* (2013.01); *C12N 2535/00* (2013.01); *G01N 2800/085* (2013.01); *G01N 2800/52* (2013.01)

(58) Field of Classification Search
CPC .......... C12N 5/0671; C12N 2502/1157; C12N 2502/1305; C12N 2502/14; C12N 2513/00; G01N 33/5082; G01N 2800/085
See application file for complete search history.

(56) References Cited

U.S. PATENT DOCUMENTS

| | | | |
|---|---|---|---|
| 4,393,133 A * | 7/1983 | Knowles | C12N 5/067 435/235.1 |
| 8,931,880 B2 | 1/2015 | Murphy et al. | |
| 9,149,952 B2 | 10/2015 | Murphy et al. | |
| 9,227,339 B2 | 1/2016 | Murphy et al. | |
| 9,315,043 B2 | 4/2016 | Murphy et al. | |
| 9,442,105 B2 * | 9/2016 | Shepherd | C12N 5/0656 |
| 9,499,779 B2 | 11/2016 | Murphy et al. | |
| 9,855,369 B2 | 1/2018 | Murphy et al. | |
| 10,174,276 B2 | 1/2019 | Murphy et al. | |
| 10,400,219 B2 | 9/2019 | Shepherd et al. | |
| 10,967,560 B2 | 4/2021 | Murphy et al. | |
| 11,124,774 B2 | 9/2021 | Shepherd et al. | |
| 11,413,805 B2 | 8/2022 | Murphy et al. | |
| 2003/0096411 A1 | 5/2003 | Michalopoulos et al. | |
| 2006/0270032 A1 | 11/2006 | Bhatia et al. | |
| 2008/0070304 A1 | 3/2008 | Forgacs et al. | |
| 2010/0189647 A1 | 7/2010 | Takayama et al. | |

(Continued)

FOREIGN PATENT DOCUMENTS

| | | |
|---|---|---|
| JP | 2010057439 A | 3/2010 |
| WO | WO-2005081970 A2 | 9/2005 |

(Continued)

OTHER PUBLICATIONS

Kanuri et al. In Vitro and in Vivo Models of Non-Alcoholic Fatty Liver Disease (NAFLD). Int. J. Mol. Sci. 2013, 14, 11963-11980 (Year: 2013).*

Kostrzewski et al. Three-dimensional perfused human in vitro model of nonalcoholic fatty liver disease. World J Gastroenterol Jan. 14, 2017; 23(2): 204-215 (Year: 2017).*

Tilg et al. Interleukin-1 and Inflammasomes in Alcoholic Liver Disease/Acute Alcoholic Hepatitis and Nonalcoholic Fatty Liver Disease/Nonalcoholic Steatohepatitis. Hepatology, vol. 64, No. 3, p. 955-965 (Year: 2016).*

(Continued)

*Primary Examiner* — Taeyoon Kim
(74) *Attorney, Agent, or Firm* — Sterne, Kessler, Goldstein & Fox P.L.L.C.

(57) ABSTRACT

The invention is directed to three-dimensional, engineered, bioprinted biological tissue constructs exhibiting a liver disorder, methods of making the constructs, and use of the constructs in assays, such as drug testing and molecular diagnostic testing, including methods of assessing the ability of a candidate therapeutic agent to reverse, reduce, or prevent a liver disorder, and methods for biomarker discovery.

15 Claims, 39 Drawing Sheets

(56) References Cited

U.S. PATENT DOCUMENTS

| | | |
|---|---|---|
| 2010/0190246 A1 | 7/2010 | Hase |
| 2012/0116568 A1 | 5/2012 | Murphy et al. |
| 2013/0164339 A1 | 6/2013 | Murphy et al. |
| 2013/0190210 A1 | 7/2013 | Murphy et al. |
| 2015/0004273 A1 | 1/2015 | Forgacs et al. |
| 2015/0037445 A1 | 2/2015 | Murphy et al. |
| 2015/0082468 A1 | 3/2015 | Bhatia et al. |
| 2015/0093932 A1 | 4/2015 | Ning et al. |
| 2016/0122723 A1 | 5/2016 | Retting et al. |
| 2016/0272946 A1 | 9/2016 | Shepherd et al. |
| 2017/0130192 A1 | 5/2017 | Retting et al. |
| 2017/0199507 A1 | 7/2017 | Murphy et al. |
| 2018/0265839 A1 | 9/2018 | Retting et al. |
| 2018/0313822 A1 | 11/2018 | Murphy et al. |
| 2019/0316093 A1* | 10/2019 | Messner ............ G01N 33/5088 |
| 2020/0197152 A1 | 6/2020 | Murphy et al. |
| 2021/0008788 A1 | 1/2021 | Murphy et al. |
| 2021/0123906 A1 | 4/2021 | Murphy et al. |
| 2021/0291432 A1 | 9/2021 | Murphy et al. |
| 2021/0395700 A1 | 12/2021 | Shepherd et al. |
| 2022/0009156 A1 | 1/2022 | Murphy et al. |
| 2022/0009157 A1 | 1/2022 | Murphy et al. |
| 2022/0195380 A1 | 6/2022 | Retting et al. |

FOREIGN PATENT DOCUMENTS

| | | | |
|---|---|---|---|
| WO | WO-2010008905 A2 | 1/2010 | |
| WO | WO-2012054195 A2 | 4/2012 | |
| WO | WO-2013040078 A2 | 3/2013 | |
| WO | WO-2013040087 A2 | 3/2013 | |
| WO | WO-2013130823 A1 | 9/2013 | |
| WO | WO-2013158508 A1 | 10/2013 | |
| WO | WO2014151921 A1 * | 9/2014 | ............ C12N 5/071 |
| WO | WO-2015017579 A1 | 2/2015 | |
| WO | WO-2017083402 A1 | 5/2017 | |
| WO | WO-2018115533 A1 * | 6/2018 | ........... C12N 5/0062 |

OTHER PUBLICATIONS

Chang, R., et al., "Biofrabrication of a three-dimensional liver micro-organ as in in vitro drug metabolism model," Biofabrication 2:1-11, 11 pages, IOP Publishing Ltd., United Kingdom (2010).

Glicklis, R., et al., "Modeling Mass Transfer in Hepatocyte Spheroids Via Cell Viability, Spheroid Size, and Hepatocellular Functions," Biotechnology and Bioengineering 86:672-680, Wiley, United States (2004).

Guillotin, B. and Guillemot, F., "Cell patterning technologies for organtypic tissue fabrication," Trends in Biotechnology 29(4):183-190, Elsevier Science Publishers B.V., Netherlands (2011).

International Search Report and Written Opinion for International Application No. PCT/US2018/025960, mailed Aug. 23, 2018, 11 pages.

Kano, K., et al., "Long-term maintenance of function of liver cells laminated on vascular endothelial cell sheet using cell sheet engineering," Regenerative Therapy 5:209, abstract No. P-114, The Japanese Society for Regenerative Medicine, Japan (Supplement 2006).

English language translation of document NPL5, Kano, K., et al., "Long-term maintenance of function of liver cells laminated on vascular endothelial cell sheet using cell sheet engineering," Regenerative Therapy 5:209, abstract No. P-114, The Japanese Society for Regenerative Medicine, Japan (Supplement 2006).

Mizumoto, H., et al., "Formation of Cylindrical Multicellular Aggregate (Cylindroid) and Express of Liver Specific Functions of Primary Rat Hepatocytes," Cytotechnology, 31:69-75, Springer, Germany (1999).

Murphy, S.V. and Atala, A., "3D bioprinting of tissues and organs," Nature Biotechnology 32(8):773-785, Nature America Publishing, United States (2014).

Norotte, C., et al., "Scaffold-free Vascular Tissue Engineering Using Bioprinting," Biomaterials 30(30):5910-5917, Elsevier Science, Netherlands (Oct. 2009).

Office Action, mailed Mar. 16, 2016 in Japanese Application No. Tokugan2016-502212, Japanese Patent Office, 9 pages.

Ohashi, K., et al., "Engineering functional two- and three-dimensional liver systems in vivo using hepatic tissue sheets," Nature Medicine 13(7):880-885, Nature Publishing Group, England (2007).

Organovo, Press Release, "Organovo Describes First Fully Cellular 3D Bioprinted Liver Tissue," Apr. 22, 2013, 2 pages.

Pampaloni, F. and Stelzer, E.H.K., "Three-Dimensional Cell Cultures in Toxicology," Biotechnology and Genetic Engineering Reviews 26:117-138, Taylor & Francis, England (2009).

Partial English language translation of FP1, Japanese Publication No. JP-2010057439-A.

Sakai, Y., "Toward engineering of vascularized three-dimensional liver tissue equivalents possessing a clinically significant mass," Biochemical Engineering Journal 48:348-361, Elsevier B.V., Netherlands (2009).

Tsuda, Y., "Preparation of temperature-reactivity patterned culture plate and construction of high-functional patterned co-cultivated cell sheets," Journal of Life Support Engineering 16(1):38-39, JStage, Japan (2004).

English language translation Tsuda, Y., "Preparation of temperature-reactivity patterned culture plate and construction of high-functional patterned co-cultivated cell sheets," Journal of Life Support Engineering 16(1):38-39, JStage, Japan (2004).

Oh, J.M., et al., "Effects of palmitic acid on TNF-α-induced cytotoxicity in SK-Hep-1 cells," Toxicology in Vitro 26(6):783-790, Elsevier, Netherlands (2012).

Gomez-Lechon, María José, et al., "A human hepatocellular in vitro model to investigate steatosis," Chemico-Biological Interactions 165(2):106-116, Elsevier, Netherlands (2007).

Chavez-Tapia, N.C., et al., "Effect of intracellular lipid accumulation in a new model of non-alcoholic fatty liver disease," BMC Gastroenterology 12:20, BMJ Publishing, United Kingdom (2012).

Jarrar, M.H., et al., "Adipokines and cytokines in non-alcoholic fatty liver disease," Aliment Pharmacol. Ther. 27(5):412-421, Wiley, United States (2007).

Kanuri, G., et al., "In vitro and in vivo models of non-alcoholic fatty liver disease (NAFLD)," Int. J. Mol. Sci. 14:11963-11980, MDPI, Switzerland (2013).

Ma, S., et al., "Inhibition of uncoupling protein 2 with genipin exacerbates palmitate-induced hepatic steatosis," Lipids in Health and Disease 11:154, BMC, United Kingdom (2012).

Ratzui, V., et al., "Current efforts and trends in the treatment of NASH," J. Hepatology 62:S65- S75, Elsevier, Netherlands (2015).

Ratzui, V., et al., "Starting the battle to control non-alcoholic steatohepatitis," Lancet 385:922-924, Elsevier, Netherlands (2015).

Teufel, A., et al., "Comparison of Gene Expression Patterns Between Mouse Models of Nonalcoholic Fatty Liver Disease and Liver Tissues From Patients," Gastroenterology 151(3):513-625, Elsevier, Netherlands (2016).

* cited by examiner

USE OF ENGINEERED LIVER TISSUE CONSTRUCTS FOR MODELING LIVER DISORDERS

BACKGROUND OF THE INVENTION

Field of the Invention

The present invention relates to three-dimensional, engineered, bioprinted biological tissue constructs exhibiting a liver disorder, methods of making the constructs, and use of the constructs in assays, such as drug testing and molecular diagnostic testing, including methods of assessing the ability of a candidate therapeutic agent to reverse, reduce, or prevent a liver disorder, and methods for biomarker discovery.

Background Art

Nonalcoholic fatty liver disease (NAFLD) is a chronic disease condition that originates as lipid accumulation within hepatocytes (steatosis) and progresses into nonalcoholic steatohepatitis (NASH), characterized by lipid accumulation, inflammation, oxidative stress, and fibrosis. Approximately 100 million adults across the United States are estimated to have NAFLD, with up to 20 million estimated to have NASH. Left unchecked, the disease can progress to cirrhosis and hepatocellular carcinoma. Because there are no specific biomarkers of this "silent" disease, diagnosis for NASH requires invasive liver biopsies. Despite well-defined morphological features and decades of intense research worldwide, the mechanisms of NAFLD progression as well as therapeutic approaches and noninvasive diagnostics are still resoundingly absent. Though there are no approved treatments for NASH, there are several potential therapeutics in trials; current standard of care consists of treatment of co-morbidities such as hypertension, obesity, or dyslipidemia.

The study of NASH has traditionally utilized rodent models, which are time consuming and do not fully recapitulate the human disease. In vivo models of the disease include both dietary supplementation in rodents (methionine-choline deficient diet, Western diet, atherosclerosis diet, etc.), genetic modifications (ob/ob and db/db mice, fa/fa rats, etc.) and combinations of dietary supplementation in genetically modified rodents. However, in vivo rodent models require significant time to develop the desired disease pathologies, rely upon genetic and/or dietary features that do not directly correlate to the human condition, and still fail to fully recapitulate all features of NASH, thus limiting their utility to study drug efficacy for treatment of the disease. Studies show little overlap in rodent and human gene expression with disease progression (Teufel et al., 2013). Compound success in rodent models does not completely translate to success in clinic (Ratzui et al., 2015).

Attempts to model NAFLD and/or NASH in vitro have also utilized 2D monolayers of hepatocytes treated with various lipid mixtures and/or cytokines (Oh, et al., Tox In Vitro, 2012; Chavez-Tapia, et al., BMC Gastroenterol, 2012; Gomez-Lechon, et al., Chemico-Biol Int, 2007; Ma, et al., Lipids Health Dis, 2012; Jarrar, et al., Aliment Pharmacol Ther, 2007). However, current 2D cell culture models have limited utility due to rapid loss of cellular phenotypes and lack of all the relevant liver cell types. 2D cell cultures also have varying reproducibility in experiments (Kanuri et al., 2013). Thus, 2D in vitro models have continually fallen short in their ability to model NAFLD progression to fibrosis, as well as full retention of the fatty liver phenotype with both significant inflammation and oxidative stress.

Thus, there is a need for a more predictive multicellular human 3D in vitro model to study the molecular aspects involved in liver disorders, such as development of fatty liver disease and its progression from steatosis into NASH with fibrosis. 3D in vitro liver models better recapitulate native human liver biology over extended time in culture. The technological advancement of 3D bioprinting enables controlled, reproducible fabrication of 3D liver mimetics from human cells, yielding durable tissues with complex composition and architecture that retain metabolic competence and liver-specific functions for at least 4 weeks in vitro. Therefore, the present invention introduces 3D, bioprinted in-vitro liver models of liver disorders, such as NAFLD, including a steatosis model and a NASH model. This invention will enable the discovery of novel therapeutics against liver disorders, such as NAFLD progression or regression of NASH, the safety assessment of drugs in a disease relevant background, and the discovery of potential biomarkers in liver disorders, such as to non-invasively delineate NASH from steatosis.

SUMMARY OF THE INVENTION

The present invention relates to a three-dimensional, engineered, bioprinted biological model of a liver disorder, comprising: a three-dimensional, engineered, bioprinted, biological liver tissue construct comprising parenchymal cells and non-parenchymal cells, the parenchymal cells comprising hepatocytes or hepatocyte-like cells, wherein at least one component of the liver tissue construct is bioprinted; and wherein the liver tissue construct exhibits at least one phenotype characteristic of a liver disorder.

In some embodiments, the at least one phenotype is selected from: a lipid accumulation, an inflammation, an oxidative stress, a fibrosis, a hepatocellular ballooning, a microvesicular steatosis, a macrovesicular steatosis, or any combination thereof. In some embodiments, the microvesicular steatosis, the macrovesicular steatosis, or a combination thereof is present in the hepatocytes. In some embodiments, the fibrosis is co-localized with activated smooth muscle actin (SMA$^+$) cells.

In some embodiments, the at least one phenotype is at least two phenotypes.

In some embodiments, the liver disorder is selected from the group consisting of: a non-alcoholic fatty liver disease (NAFLD), a non-alcoholic steatohepatitis (NASH), hepatitis A, hepatitis B, hepatitis C, alpha-1-antitrypsin deficiency, cirrhosis, a cancer, hemochromatosis, alcohol-related liver disease, primary biliary cirrhosis, a drug-related injury, or any combination thereof.

In some embodiments, the liver disorder is a NAFLD, wherein: (a) the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof (b) the NAFLD is a steatosis, and the liver tissue construct exhibits at least one phenotype that is a lipid accumulation; (c) the NAFLD is a non-alcoholic steatohepatitis (NASH), and the liver tissue construct exhibits at least two phenotypes selected from any two or more of: a lipid accumulation, an inflammation, an oxidative stress, a fibrosis, a hepatocellular ballooning, a microvesicular steatosis, or a macrovesicular steatosis; and (d) the NAFLD is an intermediate state between a steatosis and a NASH, and the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof. In some embodiments, the liver tissue construct exhibits: at least one phenotype that is a lipid accumulation and at least one phenotype that is an inflammation; at least one phenotype that is a steatosis and at least one phenotype that is a fibrosis; at least one phenotype that is a fibrosis and at least one phenotype that is a hepatocellular ballooning; or at least one phenotype that is a fibrosis, at least one phenotype that is a hepatocellular ballooning, and at least one phenotype that is a steatosis. In some embodiments, the parenchymal cells further comprise Kupffer cells, and the Kupffer cells contribute to the inflammation. In some embodiments, the liver tissue construct further exhibits the phenotype of a fibrosis. In some embodiments, the non-parenchymal cells further comprise hepatic stellate cells, and the hepatic stellate cells contribute to the fibrosis.

In some embodiments, the liver tissue construct further comprises adipocytes or adipocyte-like cells.

In some embodiments, the liver tissue construct comprises at least one compartment comprising an interior defined by a border, the interior comprising the parenchymal cells, and the border comprising non-parenchymal cells. In some embodiments, the liver tissue construct further comprises a second border surrounding the border that defines the interior, the second border comprising adipocytes or adipocyte-like cells. In some embodiments, the compartment is defined by a planar geometry.

In some embodiments, the liver tissue construct is at least three cells thick in its smallest dimension.

In some embodiments, the liver tissue construct comprises a laminar geometry, wherein a first layer comprises the non-parenchymal cells and a second layer comprises parenchymal cells. In some embodiments, the liver tissue construct further comprises a third layer of non-parenchymal cells, wherein the first layer is below the second layer, and the second layer is below the third layer.

In some embodiments, the non-parenchymal cells comprise one or more of: endothelial cells, hepatic stellate cells, vascular cells, fibroblasts, mesenchymal cells, immune cells, Kupffer cells, natural killer cells, immune cells, biliary epithelial cells, biliary epithelial-like cells, sinusoidal endothelial cells, liver-derived stem/progenitor cells, adipocytes, adipocyte-like cells, and non-liver-derived stem/progenitor cells.

In some embodiments, the parenchymal cells comprise a parenchymal bioink, the parenchymal bioink comprising at least hepatocytes or hepatocyte-like cells. In some embodiments, the parenchymal bioink further comprises Kupffer cells. In some embodiments, the parenchymal bioink further comprises an agent capable of inducing at least one phenotype selected from: a lipid accumulation, an inflammation, an oxidative stress, a fibrosis, a hepatocellular ballooning, a microvesicular steatosis, a macrovesicular steatosis, or any combination thereof.

In some embodiments, the non-parenchymal cells further comprise a non-parenchymal bioink, the non-parenchymal bioink comprising non-parenchymal cells. In some embodiments, the non-parenchymal bioink comprises at least endothelial cells. In some embodiments, the non-parenchymal bioink further comprises hepatic stellate cells. In some embodiments, the non-parenchymal bioink comprises an agent capable of inducing at least one phenotype selected from: a lipid accumulation, an inflammation, an oxidative stress, a fibrosis, a hepatocellular ballooning, a microvesicular steatosis, a macrovesicular steatosis, or any combination thereof. In some embodiments, the agent is at least one of: a fatty acid, a free fatty acid, an unsaturated fatty acid, a saturated fatty acid, a palmitic acid, a linoleic acid, a linolenic acid, a myristic acid, an oleic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a cholesterol, a high glucose, a high insulin, a genipin, a amiodarone, a valproic acid, an ethanol, a fialuridine, a tamoxifen, a triglycerides, an olanzapine, a glucocorticoids, a IL-17A, an aflatoxin B1, a fructose, a HBx protein, a lipopolysaccharide (LPS), a IL-1β, a TNF-α, any agent that is capable of inducing the Kupffer cells to contribute to an inflammation, a TGF-β, a methotrexate, an ethanol, a $CCl_4$, a thioacetamide, a vinyl chloride, a vitamin A, a hepatitis, an nonalcoholic steatohepatitis, an inflammation, a D-galactosamine, a dimethylnitrosamine, a diethylnitrosamine, an reactive oxygen species, a $H_2O_2$, a superoxide radical, a hydroxy radical, a peroxynitrite, an acetaminophen, a glutathione depletion, a chloropropionic acid, an ethacrynic acid, a NAPQI, a buthionine sulfoximine, a $CCl_4$, a clozapine, a chlorpromazine, an estrogen, a selective estrogen receptor modulator, an iron, a copper, a chromium, a vanadium, a arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

In some embodiments, the model comprises a parenchymal cell, a non-parenchymal cell, or a combination thereof from a subject having a liver disorder.

The present invention relates to a method of making a three-dimensional, engineered, bioprinted biological model of a liver disorder, comprising the steps of: contacting a three-dimensional, engineered, bioprinted biological liver tissue construct with an inducing agent that is capable of inducing the liver tissue construct to exhibit at least one phenotype characteristic of a liver disorder, provided that the three-dimensional, engineered, bioprinted, biological liver tissue construct comprises parenchymal cells and non-parenchymal cells, the parenchymal cells comprise hepatocytes and hepatocyte-like cells, and at least one component of the liver tissue construct is bioprinted. In some embodiments, the construct comprises a parenchymal cell, a non-parenchymal cell, or a combination thereof from a subject having a liver disorder. In some embodiments, the parenchymal cell, the non-parenchymal cell, or the combination thereof from the subject having a liver disorder comprises diseased cells, non-diseased cells, or a combination thereof.

The present invention relates to a method of making a three-dimensional, engineered, bioprinted biological model of a liver disorder, comprising the steps of: producing a three-dimensional, engineered, bioprinted biological liver tissue construct that exhibits at least one phenotype characteristic of a liver disorder, wherein the construct comprises a parenchymal cell, a non-parenchymal cell, or a combination thereof from a subject having a liver disorder, provided that the three-dimensional, engineered, bioprinted, biological liver tissue construct comprises parenchymal cells and non-parenchymal cells, the parenchymal cells comprise hepatocytes and hepatocyte-like cells, and at least one component of the liver tissue construct is bioprinted. In some embodiments, the parenchymal cell, the non-parenchymal cell, or the combination thereof from the subject having a liver disorder comprises diseased cells, non-diseased cells, or a combination thereof. In some embodiments, the liver tissue construct is capable of exhibiting the at least one phenotype in the absence of induction of the phenotype by an inducing agent.

The present invention relates to a method of assessing the ability of a candidate therapeutic agent to reverse, reduce or prevent a liver disorder, the method comprising: contacting a candidate therapeutic agent with a three-dimensional, engineered, bioprinted, biological liver tissue construct exhibiting at least one phenotype characteristic of a liver disorder, provided that the three-dimensional, engineered, bioprinted, biological liver tissue construct comprises parenchymal cells and non-parenchymal cells, the parenchymal cells comprise hepatocytes or hepatocyte-like cells, and at least one component of the liver tissue construct is bioprinted; determining the viability or functionality of liver tissue cells; and assessing the ability of the candidate therapeutic agent to reverse, reduce or prevent the liver disorder based on the determined viability or functionality of the liver tissue cells as compared to a control liver tissue construct that does not exhibit the phenotype characteristic of the liver disorder. In some embodiments, the construct comprises a parenchymal cell, a non-parenchymal cell, or a combination thereof from a subject having a liver disorder. In some embodiments, the parenchymal cell, the non-parenchymal cell, or the combination thereof from the subject having a liver disorder comprises diseased cells, non-diseased cells, or a combination thereof. In some embodiments, the liver tissue construct is capable of exhibiting the at least one phenotype in the absence of induction of the phenotype by an inducing agent.

The present invention relates to a method of making a three-dimensional, engineered, bioprinted biological model of a liver disorder and assessing the ability of a candidate therapeutic agent to reverse, reduce or prevent the liver disorder, the method comprising: contacting a three-dimensional, engineered, bioprinted biological liver tissue construct with: (i) an inducing agent that is capable of inducing the liver tissue construct to exhibit at least one phenotype characteristic of a liver disorder, and (ii) a candidate therapeutic agent, provided that the three-dimensional, engineered, bioprinted, biological liver tissue construct comprises parenchymal cells and non-parenchymal cells, the parenchymal cells comprise hepatocytes and hepatocyte-like cells, and at least one component of the liver tissue construct is bioprinted; determining the viability or functionality of liver tissue cells; and assessing the ability of the candidate therapeutic agent to reverse, reduce or prevent the liver disorder based on the determined viability or functionality of the liver tissue cells as compared to a control liver tissue construct that does not exhibit the phenotype characteristic of the liver disorder. In some embodiments, the inducing agent and the candidate therapeutic agent are applied daily to the liver tissue construct during a first time period. In some embodiments, the first time period is approximately 7 days, approximately 14 days, or approximately 21 days. In some embodiments, after the first time period, the method further comprises applying the candidate therapeutic agent to the liver tissue construct for a second time period. In some embodiments, the construct comprises a parenchymal cell, a non-parenchymal cell, or a combination thereof from a subject having a liver disorder. In some embodiments, the parenchymal cell, the non-parenchymal cell, or the combination thereof from the subject having a liver disorder comprises diseased cells, non-diseased cells, or a combination thereof.

In some embodiments of the methods of assessing the ability of a candidate therapeutic agent to reverse, reduce or prevent a liver disorder, the method further comprises: removing the therapeutic agent, and assessing whether the absence of the agent results in improved viability or functionality of the liver tissue cells.

In some embodiments of the methods of assessing the ability of a candidate therapeutic agent to reverse, reduce or prevent a liver disorder, the viability or functionality of the liver tissue cells is determined by measuring an indicator of metabolic activity.

In some embodiments of the methods of assessing the ability of a candidate therapeutic agent to reverse, reduce or prevent a liver disorder, the viability or functionality of the liver tissue cells is determined by evaluating, as compared to a control, one or more of the following activities: albumin production, urea production, alanine aminotransferase, LDH activity, histology, cell type-specific IHC, or any combination thereof. In some embodiments, the cell type-specific IHC is CD31, desmin, α-SMA, reelin, LOXL2, CK18, p62, CD11b, albumin, CD68, CD 163, or any combination thereof.

In some embodiments of the methods of assessing the ability of a candidate therapeutic agent to reverse, reduce or prevent a liver disorder, the viability or functionality of the liver tissue cells is determined by evaluating one or more of the following: Oil Red O, Perilipin IHC, PLIN5 IHC, Collagen I IHC, Collagen IV IHC, Sirius Red, fibrosis trichrome, or any combination thereof.

In some embodiments of the methods of assessing the ability of a candidate therapeutic agent to reverse, reduce or prevent a liver disorder, the viability or functionality of the liver tissue cells is determined by evaluating, as compared to a control, gene and/or expression for one or more of the following: fatty acid regulation, hepatic stellate cell activation, or fibrosis. In some embodiments, the gene expression for fatty acid regulation is CD36, FATP2, FATP5, FABP1, PPARs, or PPARγ. In some embodiments, the gene expression for hepatic stellate cell activation or fibrosis is a TGFβ, a TIMP, a collagen, or α-SMA.

In some embodiments of the methods of assessing the ability of a candidate therapeutic agent to reverse, reduce or prevent a liver disorder, the viability or functionality of the liver tissue cells is determined by evaluating, as compared to a control, the secretion of a pro-inflammatory cytokine.

In some embodiments of the methods of assessing the ability of a candidate therapeutic agent to reverse, reduce or prevent a liver disorder, the method further comprises the step of assessing a toxicity of the candidate therapeutic agent on the liver tissue cells. In some embodiments, the toxicity is hepatotoxicity. In some embodiments, the method further comprises the step of assessing the toxicity of the candidate therapeutic agent on the liver tissue construct that exhibits the liver disorder against the toxicity of the candidate therapeutic agent on the liver tissue construct that does not exhibit the liver disorder.

In some embodiments of the methods of assessing the ability of a candidate therapeutic agent to reverse, reduce or prevent a liver disorder, the liver cells evaluated for viability, functionality, or toxicity comprise at least parenchymal cells. In some embodiments, the parenchymal cells comprise hepatocytes or hepatocyte-like cells. In some embodiments, the parenchymal cells further comprise Kupffer cells.

In some embodiments of the methods of assessing the ability of a candidate therapeutic agent to reverse, reduce or prevent a liver disorder, the liver cells evaluated for viability, functionality, or toxicity comprise at least non-parenchymal cells. In some embodiments, the non-parenchymal cells comprise endothelial cells. In some embodiments, the non-parenchymal cells further comprise hepatic stellate cells.

In some embodiments of the methods of assessing the ability of a candidate therapeutic agent to reverse, reduce or prevent a liver disorder, the liver tissue construct is affixed to a non-human animal such that the candidate therapeutic agent is applied to the liver tissue construct while the liver tissue construct is affixed to the non-human animal. In some embodiments, the non-human animal is an immunocompromised rodent. In some embodiments, the non-human animal is reconstituted with a human immune system. In some embodiments, the liver tissue construct is affixed to the non-human animal by implanting the liver tissue construct into the non-human animal.

The present invention relates to a method of identifying a biomarker associated with at least one phenotype characteristic of a liver disorder, the method comprising: contacting a three-dimensional, engineered, bioprinted biological liver tissue construct with an inducing agent that is capable of inducing the liver tissue construct to exhibit the at least one phenotype, provided that the three-dimensional, engineered, bioprinted, biological liver tissue construct comprises parenchymal cells and non-parenchymal cells, the parenchymal cells comprise hepatocytes and hepatocyte-like cells, and at least one component of the liver tissue construct is bio-printed; and identifying a biomarker as a biological molecule that is differentially expressed by the construct that exhibits the at least one phenotype as compared to a control construct without the at least one phenotype. In some embodiments, the construct comprises a parenchymal cell, a non-parenchymal cell, or a combination thereof from a subject having a liver disorder. In some embodiments, the parenchymal cell, the non-parenchymal cell, or the combination thereof from the subject having a liver disorder comprises diseased cells, non-diseased cells, or a combination thereof.

The present invention relates to a method of identifying a biomarker associated with at least one phenotype characteristic of a liver disorder, the method comprising: preparing a three-dimensional, engineered, bioprinted biological liver tissue construct that exhibits at least one phenotype characteristic of a liver disorder, wherein the construct comprises a parenchymal cell, a non-parenchymal cell, or a combination thereof from a subject having a liver disorder, provided that the three-dimensional, engineered, bioprinted, biological liver tissue construct comprises parenchymal cells and non-parenchymal cells, the parenchymal cells comprise hepatocytes and hepatocyte-like cells, and at least one component of the liver tissue construct is bioprinted; and identifying a biomarker as a biological molecule that is differentially expressed by the construct that exhibits the at least one phenotype as compared to a control construct without the at least one phenotype. In some embodiments, the parenchymal cell, the non-parenchymal cell, or the combination thereof from the subject having a liver disorder comprises diseased cells, non-diseased cells, or a combination thereof. In some embodiments, the liver tissue construct is capable of exhibiting the at least one phenotype in the absence of induction of the phenotype by an inducing agent.

In some embodiments of the methods of identifying a biomarker associated with at least one phenotype characteristic of a liver disorder, the method further comprises determining whether the biomarker is differentially expressed in liver tissue in a subject having a liver disorder as compared to expression of the biological molecule in liver tissue in a subject without the liver disorder.

In some embodiments of the methods of identifying a biomarker associated with at least one phenotype characteristic of a liver disorder, the biological molecule is a protein or a nucleic acid molecule.

In some embodiments of the methods of identifying a biomarker associated with at least one phenotype characteristic of a liver disorder, the biological molecule is a cytokine, DNA, or RNA.

In some embodiments of the methods of identifying a biomarker associated with at least one phenotype characteristic of a liver disorder, the biological molecule is a microRNA.

In some embodiments of the methods of identifying a biomarker associated with at least one phenotype characteristic of a liver disorder, expression of the biological molecule is determined by performing a microarray analysis, RNA sequencing, or mass spectrometry.

In some embodiments of any of the above methods, the at least one phenotype is selected from: a lipid accumulation, an inflammation, an oxidative stress, a fibrosis, a hepatocellular ballooning, a microvesicular steatosis, a macrovesicular steatosis, or any combination thereof. In some embodiments, the microvesicular steatosis, the macrovesicular steatosis, or a combination thereof is present in the hepatocytes. In some embodiments, the fibrosis is co-localized with activated smooth muscle actin (SMA$^+$) cells.

In some embodiments of any of the above methods, the at least one phenotype is at least two phenotypes.

In some embodiments of any of the above methods, the liver disorder is selected from the group consisting of: a non-alcoholic fatty liver disease (NAFLD), a non-alcoholic steatohepatitis (NASH), hepatitis A, hepatitis B, hepatitis C, alpha-1-antitrypsin deficiency, cirrhosis, a cancer, hemochromatosis, alcohol-related liver disease, primary biliary cirrhosis, a drug-related injury, or any combination thereof.

In some embodiments of any of the above methods, the liver disorder is a NAFLD, wherein: (a) the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof; (b) the NAFLD is a steatosis, and the liver tissue construct exhibits at least one phenotype that is a lipid accumulation; (c) the NAFLD is a NASH, and the liver tissue construct exhibits at least two phenotypes selected from any two or more of: a lipid accumulation, an inflammation, an oxidative stress, a fibrosis, a hepatocellular ballooning, a microvesicular steatosis, a macrovesicular steatosis, or any combination thereof and (d) the NAFLD is an intermediate state between a steatosis and a NASH, and the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof.

In some embodiments of any of the above methods, the method further comprises the step of inducing the at least one phenotype after the liver tissue construct is bio-printed or during the bio-printing of the liver tissue construct.

In some embodiments of any of the above methods, at least one cell type in the liver tissue construct exhibited the at least one phenotype before bio-printing.

In some embodiments, the at least one cell type was genetically modified to exhibit the at least one phenotype before bio-printing.

In some embodiments of any of the above methods, the liver tissue construct is induced to exhibit the at least one phenotype by contacting the liver tissue construct with at least one inducing agent selected from: a fatty acid, a free fatty acid, an unsaturated fatty acid, a saturated fatty acid, a palmitic acid, a linoleic acid, a linolenic acid, a myristic acid, an oleic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a cholesterol, a high glucose, a high insulin, a fatty acid uptake enhancer, a genipin, a amiodarone, a valproic acid, an ethanol, a fialuridine, a tamoxifen, a triglycerides, an olanzapine, a glucocorticoids, an IL-17A, an aflatoxin B1, a fructose, a HBx protein, a lipopolysaccharide (LPS), an IL-1β, a TNF-α, an agent that is capable of activating the Kupffer cells to contribute to an inflammation, a TGF-β, a methotrexate, an ethanol, a CCl4, a thioacetamide, a vinyl chloride, a vitamin A, a hepatitis, an nonalcoholic steatohepatitis, an inflammation, a D-galactosamine, a dimethylnitrosamine, a diethylnitrosamine, a reactive oxygen species, a H2O2, a superoxide radical, a hydroxy radical, a peroxynitrite, an acetaminophen, a glutathione depletion, a chloropropionic acid, an ethacrynic acid, a NAPQI, a buthionine sulfoximine, a CCl4, a clozapine, a chlorpromazine, an estrogen, a selective estrogen receptor modulator, an iron, a copper, a chromium, a vanadium, a arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

In some embodiments of any of the above methods, the liver tissue construct is induced to exhibit at least one phenotype of a NAFLD by contacting the liver tissue construct with two or more agents selected from: a fructose, a fatty acid, a lipopolysaccharide (LPS), a IL1β, a TNFα, or any combination thereof.

In some embodiments of any of the above methods, the liver construct is induced to exhibit at least one phenotype that is a lipid accumulation by contacting the liver tissue construct with at least one inducing agent selected from: a fatty acid, a free fatty acid, an unsaturated fatty acid, a saturated fatty acid, a palmitic acid, a linoleic acid, a linolenic acid, a myristic acid, an oleic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a cholesterol, a high glucose, a high insulin, a genipin, a amiodarone, a valproic acid, an ethanol, a fialuridine, a tamoxifen, a triglycerides, an olanzapine, a glucocorticoids, a IL-17A, an aflatoxin B1, a fructose, a HBx protein, or any combination thereof. In some embodiments, the method further comprises contacting the liver tissue construct with a fatty acid uptake enhancer. In some embodiments, the fatty acid uptake enhancer is a genipin.

In some embodiments of any of the above methods, the liver tissue construct is induced to exhibit at least one phenotype that is an inflammation, wherein the parenchymal cells further comprise Kupffer cells, and wherein the method comprises the step of activating the Kupffer cells to contribute to the inflammation. In some embodiments, the step of activating the Kupffer cells occurs before or after a step of inducing lipid accumulation in the liver tissue construct. In some embodiments, the step of activating the Kupffer cells comprises contacting the liver tissue construct with at least one inducing agent selected from: a lipopolysaccharide (LPS), a IL-1β, an agent that is capable of activating the Kupffer cells to contribute to the inflammation, or any combination thereof.

In some embodiments of any of the above methods, the non-parenchymal cells further comprise hepatic stellate cells, and the method comprises the step of activating the hepatic stellate cells to contribute to a fibrosis. In some embodiments, the step of activating the hepatic stellate cells occurs by activating the Kupffer cells, which in turn activate the hepatic stellate cells, wherein the step of activating the hepatic stellate cells activates the Kupffer cells, or wherein the steps of activating the hepatic stellate cells and Kupffer cells occurs simultaneously, thereby enabling the induction of an inflammation and the fibrosis to occur simultaneously.

In some embodiments of any of the above methods, the liver construct is induced to exhibit at least one phenotype that is a fibrosis by contacting the liver tissue construct with at least one inducing agent selected from: a TGF-β, a methotrexate, an ethanol, a CCl4, a thioacetamide, a vinyl chloride, a vitamin A, a hepatitis, an nonalcoholic steatohepatitis, an inflammation, a D-galactosamine, a dimethylnitrosamine, a diethylnitrosamine, or any combination thereof.

In some embodiments of any of the above methods, the liver construct is induced to exhibit at least one phenotype that is an oxidative stress by contacting the liver tissue construct with at least one inducing agent selected from: a reactive oxygen species, a H2O2, a superoxide radical, a hydroxy radical, a peroxynitrite, an acetaminophen, a glutathione depletion, a chloropropionic acid, an ethacrynic acid, a NAPQI, a buthionine sulfoximine, a CCl4, a clozapine, a chlorpromazine, an estrogen, a selective estrogen receptor modulator, an iron, a copper, a chromium, a vanadium, a arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

In some embodiments of any of the above methods, the method comprises a step of simultaneously inducing the phenotype of an inflammation, a steatosis, an oxidative stress, and/or a fibrosis.

In some embodiments of any of the above methods, the method comprises a step of inducing one or more phenotypes before a step of simultaneously inducing two or more other phenotypes.

In some embodiments of any of the above methods, the liver construct is induced to exhibit at least one phenotype that is a lipid accumulation by culturing the liver tissue construct with adipocytes or adipocyte-like cells.

In some embodiments of any of the above methods, the liver tissue construct further comprises adipocytes or adipocyte-like cells.

In some embodiments of any of the above methods, the liver tissue construct comprises at least one compartment comprising an interior defined by a border, the interior comprising the parenchymal cells, and the border comprising non-parenchymal cells. In some embodiments, the liver tissue construct further comprises a second border surrounding the border that defines the interior, the second border comprising adipocytes or adipocyte-like cells. In some embodiments, the compartment is defined by a planar geometry.

In some embodiments of any of the above methods, the liver tissue construct is at least three cells thick in its smallest dimension.

In some embodiments of any of the above methods, the liver tissue construct comprises a laminar geometry, wherein a first layer comprises the non-parenchymal cells and a second layer comprises parenchymal cells. In some embodiments, the liver tissue construct further comprises a third layer of non-parenchymal cells, wherein the first layer is below the second layer, and the second layer is below the third layer.

In some embodiments of any of the above methods, the non-parenchymal cells comprise one or more of: endothelial cells, hepatic stellate cells, vascular cells, fibroblasts, mesenchymal cells, immune cells, Kupffer cells, natural killer cells, immune cells, biliary epithelial cells, biliary epithelial-like cells, sinusoidal endothelial cells, liver-derived stem/progenitor cells, adipocytes, adipocyte-like cells, and non-liver-derived stem/progenitor cells.

DETAILED DESCRIPTION OF THE INVENTION

Figure 1:
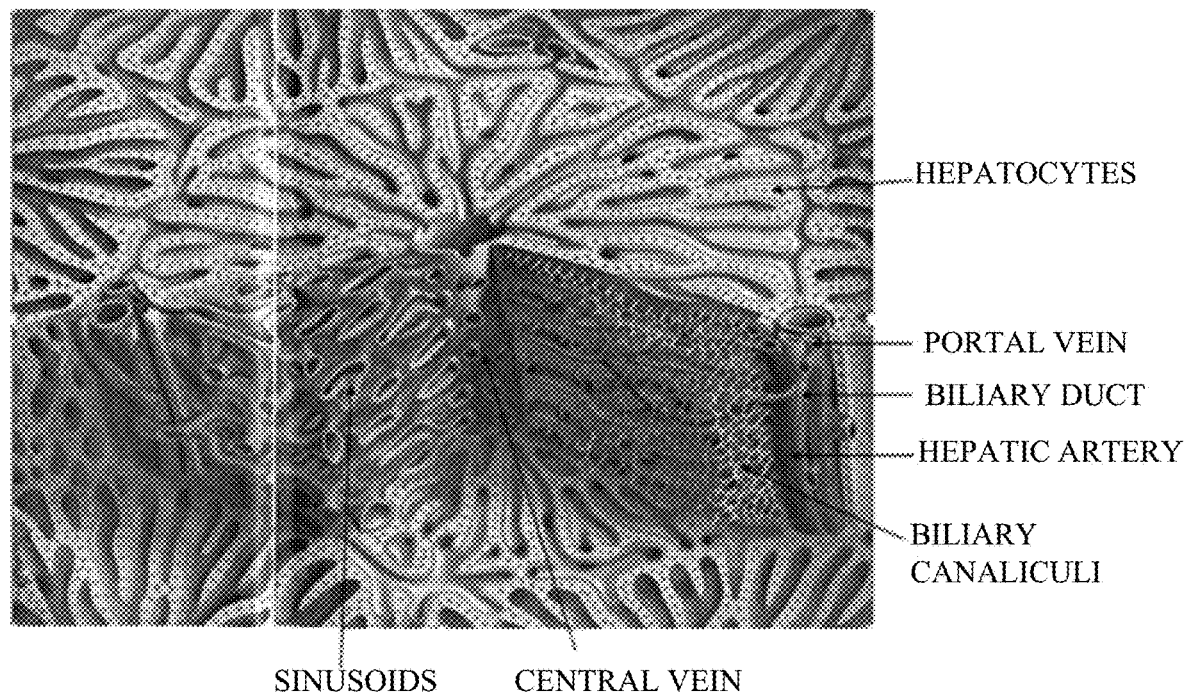
FIG. 1 is a non-limiting, exemplary illustration of native liver tissue geometry.

The present invention relates to three-dimensional, engineered, bioprinted liver tissue constructs for disease modeling, and methods of making and using the same. The liver disorder models disclosed herein represent first-in-class, fully human 3D in-vitro tissue models of liver disorders. The liver disorder models will help in the advancement of research, biomarker identification, drug discovery, and drug safety and development, thereby shortening the path to drug development and significantly impacting patient lives.

A technical challenge of creating a liver disorder model is the adverse effects of the agents that cause such liver disorder, leading to compromised viability and functionality of the living cells. For example, 2D cell culture models lack the longevity necessary to induce and progress a liver disease. Thus, to build a robust liver disorder model for drug efficacy testing, a technical challenge is keeping the living cells viable and functional over a sufficient period of time (i.e., 3, 7, 14, 21, 28, 35 days) to cover (i) the initial time period needed to induce the disorder in the liver tissue construct, and (ii) the post-induction time period to evaluate the drug efficacy and/or toxicity of a candidate therapeutic agent on the liver disorder.

Another technical challenge is the complexity involved in inducing certain liver disorders. For example, NASH is a highly complex liver disorder exhibiting several different phenotype characteristics such as lipid accumulation, inflammation, oxidative stress, hepatocellular injury resulting in a swollen, "ballooned" phenotype with cytoskeletal collapse, and fibrosis. As such, to successfully induce the NASH liver disorder model, several different agents are involved, some sequentially applied and some simultaneously applied, thereby compounding the potentially toxic effects of such agents on the viability and functionality of the living cells. Moreover, unlike 2D cell cultures, the 3D bioprinted liver tissue constructs have multicellular complexity, which adds another degree of complexity in maintaining an acceptable level of viability and functionality of these different cell types as they interact with the different agents used to induce the liver disorder.

Further, another technical challenge is the need to induce liver disorders in a significantly shorter amount of time in an in-vitro 3D, bioprinted liver model, as compared to its in-vivo state in a human. For example, in its in-vivo state in a human, NASH is a chronic condition that originates as lipid accumulation and progresses, sometimes slowly over the course of several years, to NASH. By contrast, in an in-vitro 3D, bioprinted liver model, it is not practical to wait years for a liver disorder to develop. Instead, there is a need to quickly induce the liver disorder in a time period as short as days in order to maximize the post-induction time period for drug testing, such as assessing a therapeutic drug's efficacy on reversing, reducing, or preventing the liver disorder, or toxicity testing. For example, if the liver tissue cells can remain reasonably viable and functional for at least 28 days, then the ability to quickly induce the liver disorder in about 21 days or less will maximize the post-induction time period remaining for drug efficacy and toxicity testing. Therefore, the present invention aims to reduce the time period needed to induce liver disorders without severely compromising the viability and functionality of the liver tissue cells.

To solve these and other technical challenges, the present invention introduces 3D, bioprinted liver tissue constructs exhibiting a liver disorder, and accompanying methods of making and using such liver tissue constructs.

Certain Definitions

Unless otherwise defined, all technical terms used herein have the same meaning as commonly understood by one of ordinary skill in the art to which this invention belongs.

As used in this specification and the appended claims, the singular forms "a," "an," and "the" include plural references unless the context clearly dictates otherwise.

The use of the alternative (e.g., "or") should be understood to mean either one, both, or any combination thereof of the alternatives. Any reference to "or" herein is intended to encompass "and/or" unless otherwise stated. The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of and/or" consisting essentially of are also provided.

As used herein, "about" means±10% of the recited value. For example, about 10 includes 9-11.

As described herein, any concentration range, percentage range, ratio range or integer range is to be understood to include the value of any integer within the recited range and, when appropriate, fractions thereof (such as one tenth and one hundredth of an integer), unless otherwise indicated.

As used herein, "array" means a scientific tool including an association of multiple elements spatially arranged to allow a plurality of tests to be performed on a sample, one or more tests to be performed on a plurality of samples, or both. In some embodiments, a plurality of the models as disclosed herein are configured to form an array. In some embodiments, the arrays are adapted for, or compatible with, screening methods and devices, including those associated with medium- or high-throughput screening. In further embodiments, an array allows a plurality of tests to be performed simultaneously. In further embodiments, an array allows a plurality of samples to be tested simultaneously. In some embodiments, the arrays are cellular microarrays. In further embodiments, a cellular microarray is a laboratory tool that allows for the multiplex interrogation of living cells on the surface of a solid support. In other embodiments, the arrays are tissue microarrays. In further embodiments, tissue microarrays include a plurality of separate tissues or tissue samples assembled in an array to allow the performance of multiple biochemical, metabolic, molecular, or histological analyses (Murphy et al., 2013). In some embodiments, the array is present in the wells of a microtiter plate.

As used herein, "assay" means a procedure for testing or measuring the presence or activity of a substance (e.g., a chemical, molecule, biochemical, protein, hormone, or drug, etc.) in an organic or biologic sample (e.g., cell aggregate, tissue, organ, organism, etc.).

As used herein, "biocompatible membrane" means a membrane that is not toxic to tissue.

As used herein, "bio-ink" means a liquid, semi-solid, or solid composition for use in bioprinting. In some embodiments, bio-ink comprises cell solutions, cell aggregates, cell-comprising gels, multicellular bodies, or tissues. In some embodiments, the bio-ink additionally comprises non-cellular materials that provide specific biomechanical properties that enable bioprinting. In some embodiments, the bio-ink comprises an extrusion compound. In some cases, the extrusion compound is engineered to be removed after the bioprinting process. In other embodiments, at least some portion of the extrusion compound remains entrained with the cells post-printing and is not removed.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter). Suitable bioprinters include the NovoGen Bioprinter™ from Organovo, Inc. (San Diego, CA) and those described in U.S. Pat. No. 9,149,952 and U.S. Publication Appl. Nos. 2015/0093932, 2015/0004273, and 2015/0037445.

As used herein, "cohere," "cohered," and "cohesion" refer to cell-cell adhesion properties that bind cells, cell aggregates, multicellular aggregates, multicellular bodies, and/or layers thereof. The terms are used interchangeably with "fuse," "fused," and "fusion."

As used herein, "cylindrical" means having substantially the form of a cylinder. In various embodiments, cylindrical bio-ink has substantially the form of a cylinder and is about 99, 98, 97, 96, 95, 94, 93, 92, 91, 90, 85, 80, 75, 70, 65, or 60 percent, including increments therein, cylindrical in form. In further various embodiments, cylindrical bio-ink has substantially the form of a cylinder along about 99, 98, 97, 96, 95, 94, 93, 92, 91, 90, 85, 80, 75, 70, 65, 60, 55, or 50 percent, including increments therein, of its length. In some embodiments, "cylindrical" means having substantially the form of a cylinder at the time of fabrication.

As used herein, "laminar" means a multi-layered bioprinted tissue in which two or more planar layers are combined to increase the overall thickness of the tissue in the Z-plane. In some embodiments, each planar layer is substantially similar in architecture and/or composition. In other embodiments, each planar layer is substantially distinct in architecture and/or composition.

As used herein, "layer" means an association of cells in X and Y planes that is one or multiple cells thick. In various embodiments, a layer forms a contiguous, substantially contiguous, or non-contiguous sheet of cells.

As used herein, "multi-layered" means being comprised of two or more layers of tissue, wherein each tissue layer is one or more cell-layers in thickness. In some embodiments, layers of tissue are deposited one at a time. In other embodiments, multiple layers are deposited simultaneously. Optionally, each layer is comprised of multiple cell types. Further, the multiple cell types within each layer are optionally arranged relative to each other in a spatially-defined architecture in the X-Y planes (i.e., horizontal planes). Furthermore, addition of layers in the Z-plane (i.e., vertical plane), in some cases, results in controlled spatial positioning of the cells within the layers relative to each other so that a spatially-defined architecture is continued in the Z-plane.

As used herein, "multi-potent cells" refers to cells that are capable of undergoing differentiation to two or more cell types. Multi-potent cells include, for example, mesenchymal stem/stromal cells, induced pluripotent stem cells, and embryonic stem cells.

As used herein, "parenchymal cells" means at least one cell type is a hepatocyte or a hepatocyte-like cell. As used herein, "non-parenchymal cells" refers to cells that are not hepatocytes or hepatocyte-like cells. Therefore, parenchymal cells can include hepatocytes and non-parenchymal cells. By way of a non-limiting example, parenchymal cells can include hepatocytes and Kupffer cells.

As used herein, "planar" means a layer of multicellular bioprinted tissue in which multiple bio-ink compositions and/or void spaces are spatially arranged into a defined pattern relative to each other substantially within the X-Y plane of the tissue layer. See, e.g., FIGS. 18A-E. In various embodiments, a planar layer is substantially planar, for example, about 99, 98, 97, 96, 95, 94, 93, 92, 91, 90, 85, 80, 75, 70, 65, or 60 percent, including increments therein, spatially arranged into a defined pattern within the X-Y plane of the tissue layer.

As used herein, "scaffold" refers to synthetic scaffolds such as polymer scaffolds and porous hydrogels (including, e.g., a biopaper into which a cell is embedded), non-synthetic scaffolds such as pre-formed extracellular matrix layers, dead cell layers, and decellularized tissues, and any other type of pre-formed scaffold that is integral to the physical structure of the engineered tissue and not able to be removed from the tissue without damage/destruction of said tissue. In further embodiments, decellularized tissue scaffolds include decellularized native tissues or decellularized cellular material generated by cultured cells in any manner; for example, cell layers that are allowed to die or are decellularized, leaving behind the extracellular matrix (ECM) they produced while living. The term "scaffoldless," therefore, is intended to imply that pre-formed scaffold is not an integral part of the engineered tissue at the time of use, either having been removed or remaining as an inert component of the engineered tissue. "Scaffoldless" is used interchangeably with "scaffold-free" and "free of preformed scaffold."

As used herein a "subject" is an organism of any mammalian species including but not limited to humans, primates, apes, monkey, dogs, cats, mice, rats, rabbits, pigs, horses and others. A subject can be any mammalian species alive or dead. Subject includes recently deceased subjects or biopsy samples taken from a living subject. In some embodiments, the subject is a human. The terms "subject" and "patient" and "donor" are used interchangeably herein.

As used herein "therapeutic substance" means any molecule, biologic, compound or composition that is approved to treat a disease, under investigation to treat a disease, or that elicits a biological response such as changes in DNA, RNA, peptide, polypeptide or protein.

As used herein, "tissue" means an aggregate of cells.

Tissue Engineering

Tissue engineering is an interdisciplinary field that applies and combines the principles of engineering and life sciences toward the development of biological substitutes that restore, maintain, or improve tissue function through augmentation, repair, or replacement of an organ or tissue. The basic approach to classical tissue engineering is to seed living cells into a biocompatible and eventually biodegradable environment (e.g., a scaffold), and then culture this construct in a bioreactor so that the initial cell population expands further and matures to generate the target tissue upon implantation. With an appropriate scaffold that mimics the biological extracellular matrix (ECM), the developing tissue, in some cases, adopts both the form and function of the desired organ after in vitro and in vivo maturation. However, achieving high enough cell density with a native tissue-like architecture is challenging due to the limited ability to control the distribution and spatial arrangement of the cells throughout the scaffold. These limitations often result in tissues or organs with poor mechanical properties and/or insufficient function. Additional challenges exist with regard to biodegradation of the scaffold, entrapment of residual polymer, and industrial scale-up of manufacturing processes. Scaffoldless approaches have been attempted. Current scaffoldless approaches are subject to several limitations: Complex planar and/or laminar geometries, such as multi-layered structures wherein one or more layers is compositionally or architecturally distinct from other layers or wherein one or more layers comprise multiple cell types in spatially-defined positions relative to each other, often require definitive, high-resolution placement of cell types within a specific architecture to reproducibly achieve a native tissue-like outcome. Scale and geometry are limited by diffusion and/or the requirement for functional vascular networks for nutrient supply. The viability of the tissues is, in some cases, compromised by confinement material that limits diffusion and restricts the cells' access to nutrients.

Disclosed herein, in certain embodiments, are engineered mammalian tissues, engineered liver tissues/constructs, arrays thereof, and methods of fabrication. The tissue engineering methods disclosed herein have the following advantages: They are capable of producing cell-comprising tissues and/or organs. They mimic the environmental conditions found within the development, homeostasis, and/or pathogenesis of natural tissues by re-creating native tissue-like intercellular interactions. They optionally achieve living, three-dimensional tissues and compound tissues with a broad array of complex topologies and geometries (e.g., multilayered structures, segments, sheets, tubes, sacs, etc.). They are compatible with automated or semi-automated means of manufacturing and are scalable.

Bioprinting enables improved methods of generating micro-scale tissue analogues including those useful for in vitro assays (see below).

Bioprinting

In some embodiments, at least one component of the engineered liver tissues/constructs, and arrays thereof is bioprinted. In further embodiments, bioprinted constructs are made with a method that utilizes a rapid prototyping technology based on three-dimensional, automated, computer-aided deposition of cells, including cell solutions, cell suspensions, cell-comprising gels or pastes, cell concentrations, multicellular bodies (e.g., cylinders, spheroids, ribbons, etc.), and, optionally, confinement material onto a biocompatible support surface (e.g., composed of hydrogel and/or a porous membrane) by a three-dimensional delivery device (e.g., a bioprinter). As used herein, in some embodiments, the term "engineered," when used to refer to tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules. In still further embodiments, three-dimensional tissue structures form through the post-printing fusion of cells or multicellular bodies which, in some cases, is similar to self-assembly phenomena in early morphogenesis.

Figure 9:
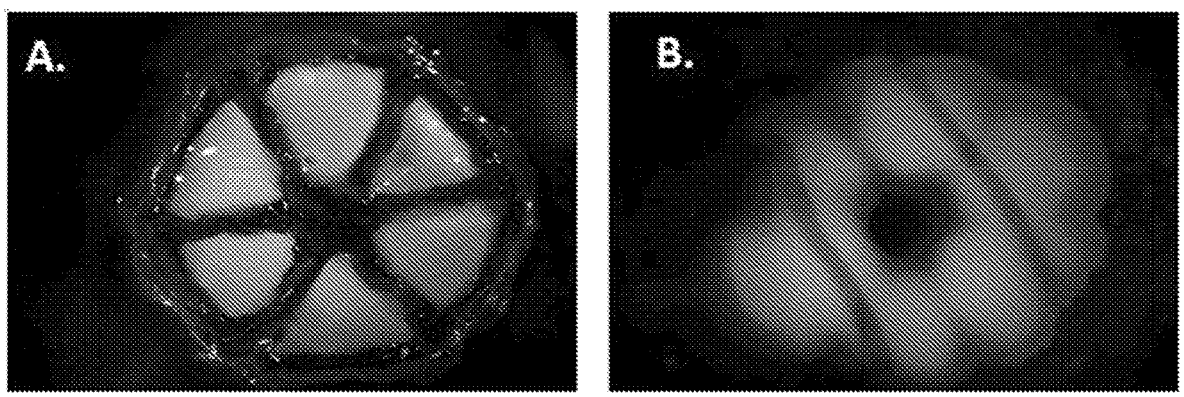
FIG. 9 is a non-limiting example of a co-printed mold (4% Gelatin and 2% Alginate) bio-printed using a Syringe Deposition Module (SDM) of a MMX Bioprinter produces constructs (A) that fuse and mature into hepatic tissues 72 hours post print (B). In this example, the bio-printed tissue is dense demonstrated by the H and E staining (C) and viable as demonstrated by relatively fewer TUNEL stained cells (D) compared to proliferating cells (E).
Figure 9:
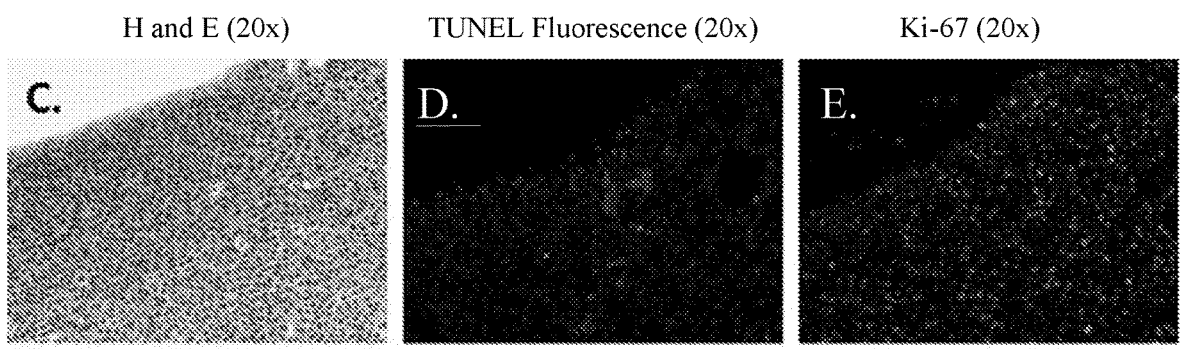

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage. Parenchymal cells of the liver are particularly susceptible to damage by shear force and other biomechanical stress; thus the combined use of bio-ink and the bioprinting process described herein provides a distinct advantage over alternative technologies as highlighted by the favorable viability of the parenchymal cells after bioprinting as highlighted in FIG. 9.

In some embodiments, the method of bioprinting is continuous and/or substantially continuous. A non-limiting example of a continuous bioprinting method is to dispense bio-ink (i.e., cells, cells combined with an excipient or extrusion compound, or aggregates of cells) from a bioprinter via a dispense tip (e.g., a syringe, needle, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries, thereby resulting in one or more tissue layers with planar geometry achieved via spatial patterning of distinct bio-inks and/or void spaces. In further embodiments, a repeating pattern of bioprinted function units comprises a layer and a plurality of layers are bioprinted adjacently (e.g., stacked) to form an engineered tissue or organ with laminar geometry. In various embodiments, 2, 3, 4, 5, 6, 7, 8, 9, 10, 11, 12, 13, 14, 15, or more layers are bioprinted adjacently (e.g., stacked) to form an engineered tissue or organ. In further embodiments, one or more layers of a tissue with laminar geometry also has planar geometry.

In some embodiments, a functional unit consists of a number of fused or cohered tubular structures which are arranged in both the horizontal and vertical dimensions to form a contiguous liver tissue structure that contains void spaces or channels at regular intervals which allows perfusion across and/or through the engineered liver tissue. See FIGS. 17 and 19.

In some embodiments, a bioprinted functional unit repeats in a tessellated pattern. A "tessellated pattern" is a plane of figures that fills the plane with no overlaps and no gaps. FIG. 6A shows an example of a functional unit that is optionally repeated to produce the tessellation pattern depicted in FIGS. 6B-D and 7. Advantages of continuous and/or tessellated bioprinting includes, by way of non-limiting example, increased productivity of bioprinted tissue. Another non-limiting, exemplary advantage is eliminating the need to align the bioprinter with previously deposited elements of bio-ink. In some embodiments, continuous bioprinting facilitates printing larger tissues from a large reservoir of bio-ink, optionally using a syringe mechanism. Continuous bioprinting is also a convenient way to co-print spatially-defined boundaries, using an extrusion compound, a hydrogel, a polymer, bio-ink, or any printable material that is capable of retaining its shape post-printing; wherein the boundaries that are created are optionally filled in via the bioprinting of a one or more bio-inks, thereby creating a mosaic tissue with spatially-defined planar geometry, see for example, the embodiments illustrated in FIGS. 3A, 5A, 5B, 6, 8, and 11.

In some embodiments, methods in continuous bioprinting involve optimizing and/or balancing parameters such as print height, pump speed, robot speed, or combinations thereof independently or relative to each other. In certain cases, the bioprinter head speed for deposition was 3 mm/s, with a dispense height of 0.5 mm for the first layer and dispense height was increased 0.4 mm for each subsequent layer. In some embodiments, the dispense height is approximately equal to the diameter of the bioprinter dispense tip. Without limitation a suitable and/or optimal dispense distance does not result in material flattening or adhering to the dispensing needle. In various embodiments, the bioprinter dispense tip has an inner diameter of about, 20, 50, 100, 150, 200, 250, 300, 350, 400, 450, 500, 550, 600, 650, 700, 750, 800, 850, 900, 950, 1000 μm, or more, including increments therein. In various embodiments, the bio-ink reservoir of the bioprinter has a volume of about 0.05, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100 cubic centimeters, or more, including increments therein. The pump speed is, in some cases, suitable and/or optimal when the residual pressure build-up in the system is low. Favorable pump speeds, in some cases, depend on the ratio between the cross-sectional areas of the reservoir and dispense needle with larger ratios requiring lower pump speeds. In some embodiments, a suitable and/or optimal print speed enables the deposition of a uniform line without affecting the mechanical integrity of the material.

In some embodiments, the speed and scalability of the techniques and methods disclosed herein are utilized to design, build, and operate industrial and/or commercial facilities for production of engineered liver tissues and/or organs for implantation or use in generation of cell-based tools for research and development, such as in vitro assays. In further embodiments, the engineered liver tissues and/or organs and arrays thereof are produced, stored, distributed, marketed, advertised, and sold as, for example, cellular arrays (e.g., microarrays or chips), tissue arrays (e.g., microarrays or chips), and kits for biological assays and high-throughput drug screening. In other embodiments, the engineered liver tissues and/or organs and arrays thereof are produced and utilized to conduct biological assays and/or drug screening as a service.

Engineered Liver Tissues

Referring to FIG. 1, native liver tissue is comprised of multiple cell types, arranged in a distinct, spatially-patterned architecture relative to each other. Each liver lobule constitutes an operating functional unit of liver and is roughly hexagonal in shape. Parenchymal cells, such as hepatocytes, largely constitute the lobules with various non-parenchymal cells (bile duct cells, sinusoidal endothelial cells, stellate cells, and Kupffer cells) in adjunct positions surrounding the lobule and radiating between the portal veins and bile ducts (along the periphery of the lobule) toward the central vein (in the center of the lobule). The positioning of non-parenchymal cells and the flow of blood and bile along the sinusoids and bile canaliculi, respectively, act together to form the proper micro-environment for the hepatocytes and thus influence the state of health and function of those cells. Various pathological conditions, like cirrhosis or fibrosis in the liver, lead to loss of critical metabolic functions as the hepatocyte microenvironment is disrupted and the architecture of the liver is progressively destroyed due to overproduction of extracellular matrix, inflammation, and production of pathogenic cytokines and growth factors.

Bioprinting enables compartmentalized liver tissue to be generated from multiple cellular inputs in 3D, thus recapitulating key elements of native tissue architecture and function. Lobulated tissues can be generated per the examples provided herein, wherein the parenchymal and non-parenchymal cells are spatially arranged relative to each other, creating a planar geometry within each layer of tissue that is fabricated. Subsequent layers can be added that either reproduce the geometry of the first layer precisely, or introduce additional features such as void spaces or channels or additional biological elements, such as tumor cells or other biological or biochemical components associated with pathogenic or reparative/regenerative processes. In addition to lobulated patterns, one can utilize the accompanying diagrams to appreciate that bioprinted tissue could be generated that reproduces specific spatial relationships within tissues, including but not limited to: vascular/parenchymal; vascular/hepatocyte; hepatocyte/bile duct; fibrotic tissue/vasculature; fibrotic tissue/hepatocyte; hepatocyte/immune cells; parenchymal/non-parenchymal, hepatic sinusoid/blood or blood surrogate. In further embodiments, the liver tissue analogues comprise: hepatocytes or hepatocyte-like cells and optionally bile duct epithelial cells and optionally, non-parenchymal cell types including, but not limited to, stellate cells, endothelial cells, Kupffer cells, immune cells, or myofibroblasts.

Also disclosed herein, in certain embodiments, are engineered liver tissues comprising cohered, mammalian cells, and further comprising one or more layers of mammalian cells, wherein at least one component of the tissue was bioprinted. In some embodiments, one or more of the tissue layers is characterized by a planar geometry, wherein multiple cell types or bio-ink types and/or void spaces exist in spatially-defined positions in the X-Y planes. In some embodiments, the tissues are multi-layered wherein at least one of the layers is architecturally or compositionally distinct from the other layers, giving the tissue a characteristic laminar geometry. In further embodiments, the layers are of similar thickness in the Z-plane. In still further embodiments, the layers are of variable thickness in the Z-plane. In further embodiments, any single layer is one cell layer in thickness. In some embodiments, the tissues are liver analogues. In further embodiments, the liver tissue analogues comprise: hepatocytes or hepatocyte-like cells and optionally bile duct epithelial cells and optionally, non-parenchymal cell types including, but not limited to, stellate cells, endothelial cells, Kupffer cells, immune cells, or myofibroblasts. In some embodiments, the resulting liver tissue constructs are at least about 50 microns in thickness in the x, y, and z planes.

In some embodiments, the engineered liver tissues/constructs, are bioprinted, a methodology described herein. In further embodiments, at least one component of the engineered tissue is bioprinted. In still further embodiments, additional components of the tissue are bioprinted. In some embodiments, the tissues are free of any pre-formed scaffold as described further herein at the time of manufacture or at the time of use. In some embodiments, as a result of being fabricated by tissue engineering techniques, including bioprinting, the tissues of the present invention are further distinguished from tissues developed in vivo, as part of an organism.

In some embodiments, the engineered liver tissue includes any type of mammalian cell. In various further embodiments, the engineered liver tissue includes 1, 2, 3, 4, 5, 6, 7, 8, 9, 10, 11, 12, 13, 14, 15, 16, 17, 18, 19, 20 or more cell types. In some embodiments, the cells of the engineered liver tissue are "cohered" or "adhered" to one another. In further embodiments, cohesion or adhesion refers to cell-cell adhesion properties that bind cells, multicellular aggregates, multicellular bodies, and/or layers thereof.

In some embodiments, the engineered liver tissues/constructs, include one or more layers of cells. In further embodiments, one or more of the layers is characterized by having a planar geometry. In still further embodiments, multiple layers of the engineered tissue have a planar geometry; wherein the planar geometries are variable among layers or are the same. In still further embodiments, planar geometries (X-Y planes) in individual layers are aligned in the Z-plane during fabrication so that additional geometry is created in the Z-plane in the composite tissue. In some embodiments, one or more of the layers within the multi-layered architecture is characterized further by having planar geometry.

In some embodiments, a layer of cells comprises one or more sheets of cells. In various embodiments, a sheet of cells is about 1, 2, 3, 4, 5, 6, 7, 8, 9, 10, 20, 30, 40, 50, 60, 70, 80, 90, 100 or more cells thick, including increments therein. In other various embodiments, a sheet of cells is about 3, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more µm thick, including increments therein. In some embodiments, a layer of tissue comprises fused aggregates of cells. In further embodiments, prior to fusion, the aggregates of cells have, by way of non-limiting examples, a defined shape and/or architecture, being substantially spherical, elongate, substantially cylindrical and ribbon-like shape. In various embodiments, fused aggregates of cells form a layer about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more µm thick, including increments therein.

In some embodiments, the one or more layers include any type of mammalian cell. In various further embodiments, each layer includes 1, 2, 3, 4, 5, 6, 7, 8, 9, 10, 11, 12, 13, 14, 15, 16, 17, 18, 19, 20 or more cell types. In some embodiments, the engineered liver tissues/constructs include one or more layers of endothelial cells on one or more surfaces. In other embodiments, the engineered liver tissues/constructs include one or more layers of epithelial cells on one or more surfaces.

The engineered liver tissues, in various embodiments, are any suitable size. In some embodiments, the size of bioprinted liver tissue, change over time. In further embodiments, an engineered liver tissue shrinks or contracts after bioprinting due to, for example, cell migration, cell death, intercellular interactions, contraction, or other forms of shrinkage. In other embodiments, an engineered liver tissue grows or expands after bioprinting due to, for example, cell migration, cell growth and proliferation, production of extracellular matrix or other cell-produced components of native tissue, cell/tissue maturation or other forms of expansion.

In some embodiments, the physical dimensions of the engineered liver tissues are limited by the capacity for nutrients, including oxygen, to diffuse into the interior of the construct. In various embodiments, the engineered liver tissues/constructs are at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, or 1000 µm in their smallest dimension at the time of bioprinting. In various embodiments, the engineered liver tissues are at least about 0.25, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, or 5.0 mm in their smallest dimension at the time of bioprinting. In further embodiments, the engineered liver tissues/constructs are between about 25 µm and about 500 µm in their smallest dimension at the time of bioprinting.

The engineered liver tissues, in various embodiments, are any suitable shape. In some embodiments, the shape is selected to mimic a particular natural tissue or organ. In further embodiments, the shape is selected to mimic a particular pathology, condition, or disease state. In some embodiments, the engineered liver tissues have a shape that is substantially planar. In further embodiments, planar tissues have any suitable planar geometry including, by way of non-limiting examples, square, rectangle, polygon, circle, oval, or irregular. In some embodiments, a planar geometry is generated in an engineered liver tissue by positioning specific cellular or bio-ink components and/or void spaces in the X-Y planes relative to each other.

In some embodiments, the engineered liver tissues/constructs are secured to a containment vessel by a means suitable to fix the position of the tissue in space relative to the containment vessel. In some embodiments, the engineered liver tissues are confined by a biocompatible material that provides physical support on one or more sides and constrains the space that the engineered liver tissue occupies. In further embodiments, the engineered liver tissues are affixed to a surface. In further embodiments, the engineered liver tissues are affixed to a biocompatible surface. In still further embodiments, a plurality of tissues are associated by affixation to a surface and spatially arranged to form an array, as described herein. In some embodiments, engineered liver tissues are subjected to shear force, caused by fluid flow, on one or more sides. In further embodiments, application of shear force serves to facilitate the maturation and development of a tissue and/or facilitate the migration, differentiation, proliferation, deposition of extracellular matrix, or transport of proteins or molecules into or out of cells within the tissue. In other embodiments, the engineered liver tissues are subjected to continuous or periodic perfusion, recirculation, or agitation of liquid nutrients on one or more surfaces. In other embodiments, the engineered liver tissues and arrays thereof are housed in a multi-well bioreactor that provides continuous or periodic recirculation of the liquid culture media for each construct.

Tissue Geometries

Native tissues are characterized by the presence of spatial and compositional patterns driven by the cellular and extracellular (i.e., void spaces, extracellular matrices, proteinaceous matter, etc.) components of a tissue. Inherent challenges to tissue engineering strategies that deploy synthetic scaffolding to achieve three-dimensionality is the inability to reproduce both the geometric and biologic attributes of native tissue. To date, attempts to create native tissue-like laminar or planar geometry within a scaffold structure while also enabling the incorporation of cells at a density that mimics native tissue have been hampered by technical limitations. Bioprinting overcomes both inherent challenges (planar/laminar geometry and cell density) through the spatially-defined deposition of bio-ink comprised of cells, according to the examples illustrated in FIGS. 18A-E. In some embodiments, planar geometries are created from multiple bio-ink formulations, whereby two or more tissue components (i.e., stromal, epithelial, vascular, bone, cartilage, parenchymal, cortical, medullary, papillary, lobular, etc.) are fabricated in a manner that positions each tissue component/cell population/bio-ink formulation in a defined position relative to each other in the X, Y, and/or Z planes. In some embodiments, the planar geometry incorporates void spaces. In further embodiments, the void spaces within the planar geometry accommodate fluids that mimic at least one element of bodily fluids, such as blood, lymph, bile, urine, secretions, and the like. In further embodiments, the void spaces optionally contain non-adherent cell types or bodily-fluid-derived components (e.g., blood cells, marrow cells, lymphatic cells, immune cells, cancer cells, platelets, proteins, etc.). In still further embodiments, non-adherent cell types of bodily-fluid-derived components optionally exist as a component of non-void spaces having been introduced into the cell-comprising components of the planar geometry before, during, or after fabrication. In still further embodiments, non-adherent cellular components or bodily-fluid-derived components are recruited from void spaces into cell-comprising spaces within the planar geometry as a result of intercellular interactions or response to secreted factors.

In some embodiments, fluid flow or perfusion is optionally initiated through the void spaces within a geometry. In some embodiments, planar geometries enable the generation of tissue-tissue or tissue-liquid interfaces. In further embodiments, the tissues are fabricated into containers that are optically clear to enable real-time observation of cells at the interface(s) created by the geometry.

In some embodiments, tissues comprise multiple layers wherein at least one of the layers is architecturally or compositionally distinct from other layers within the construct, thereby creating a laminar architecture in the Z-plane. Examples of laminar architecture include barrier tissues that possess an endothelial or epithelial barrier to an underlying interstitial tissue as depicted by the examples shown in FIG. 18F. In some embodiments, one or more layers of a tissue incorporate vascular or microvascular components. In further embodiments, the incorporation of vascular or microvascular components leads to the formation of microvascular or pseudovascular networks within one or more components of the engineered tissue. In some embodiments, one or more components of the tissue with laminar geometry are bioprinted. In some embodiments, one or more tissues with laminar geometry are fabricated adjacent to each other, thereby creating a tissue interface.

In some embodiments, one or more layers of a multi-layered engineered tissue with laminar geometry also comprise planar geometry, according to the non-limiting examples set forth in FIG. 18G. In some embodiments, the same planar geometry is continued in each layer, resulting in a three-dimensional tissue with continuous architecture in the X, Y, and Z planes. In some embodiments, the composition or planar geometry of one or more laminar layers is varied, such that the resulting three-dimensional tissue possesses a complex architecture in the X, Y and Z planes.

Referring to FIG. 18A, in a particular embodiment, an engineered liver tissue is fabricated with a planar geometry representing an architecturally-correct tissue with a vascular network. In this embodiment, an engineered liver tissue is fabricated with a first bio-ink including parenchymal cells, such as liver cells. Each layer of parenchymal cells optionally includes any planar pattern. In this embodiment, an engineered liver tissue is fabricated with a second bio-ink including vascular-related cells, such as endothelial cells, smooth muscle cells, and fibroblast to form a vascular network. Optionally, this architecture may be created by first bioprinting and establishing the vascular network, and then fabricating liver tissue surrounding that network in a second step.

Referring to FIG. 18B, in a particular embodiment, an engineered liver tissue is fabricated with a planar geometry representing a tissue zonal junction. This could be utilized, for example, to replicate the three specific zones of the hepatic acinus from the periportal region to the centrilobular region.

Referring to FIG. 18C, in a particular embodiment, an engineered liver tissue is fabricated with a planar geometry representing a lobulated tissue. In this embodiment, an engineered liver tissue is fabricated with a first bio-ink including liver cells to form lobules. Each geometric lobule optionally includes a spatially-directed architecture within its boundaries. In this embodiment, an engineered liver tissue is fabricated with a second bio-ink including stromal/vascular cells to form borders around the lobules.

Referring to FIG. 18D, in a particular embodiment, an engineered liver tissue is fabricated with a planar geometry representing a perfused/arrayed tissue. In this embodiment, a first component forms channels, vessels, or tubes with lumens. In this embodiment, a second component forms tissue patches that are optionally the same size/shape or different sizes/shapes, optionally include one cell type or a plurality of cell types, and optionally include one or more spatial patterns achieved by directed patterning in the X, Y, and or Z planes.

Referring to FIG. 18E, in a particular embodiment, an engineered liver tissue is fabricated with a planar geometry representing a solid+liquid/liquid tissue interface. In this embodiment, a first bio-ink forms the outer wall of a luminal structure, a second bio-ink forms the inner wall of a luminal structure where required, and third component is optionally a fluid containing cells or other biologically relevant components.

Referring to FIG. 18F, in a particular embodiment, an engineered liver tissue is fabricated with a laminar geometry representing a barrier tissue. In this embodiment, a barrier layer is optionally endothelial or epithelial and an interstitial layer forms the wall and/or surface of a luminal tissue, which rests upon a porous mesh or membrane.

Referring to FIG. 18G, in a particular embodiment, an engineered liver tissue is fabricated with a plurality of layers, each with a planar geometry and stacked to form a tissue with a laminar geometry. In this embodiment, the planar geometry of the X and Y axes is continued through the Z-axis into the fabricated tissue. Features of the geometry optionally include contiguous channels or cellular compartments.

Cells

Disclosed herein, in some embodiments, are engineered liver tissues (e.g., liver analogues) comprising one or more types of mammalian cells. In further embodiments, the engineered liver tissues comprise hepatocytes or hepatocyte-like cells. In still further embodiments, suitable hepatocytes or hepatocyte-like cells include, but are not limited to, primary hepatocytes, cell lines such as HepG2 cells, tissue-specific progenitors such as HepaRG cells, or combinations thereof. In further embodiments, the engineered liver tissues comprise bile duct epithelial or bile duct epithelial-like cells. In further embodiments, the engineered liver tissues comprise non-parenchymal cells. In still further embodiments, suitable non-parenchymal cells include, but are not limited to, vascular cells, endothelial cells, fibroblasts, myofibroblasts, adipocytes, adipogenic cells, mesenchymal cells, immune cells, Kupffer cells, stellate cells, biliary epithelial cells, biliary epithelial-like cells, sinusoidal endothelial cells, liver-derived stem/progenitor cells, non-liver-derived stem/progenitor cells, and combinations thereof.

In some embodiments, any mammalian cell is suitable for inclusion in the engineered liver tissues and arrays thereof. In further embodiments, at least one component of the engineered liver tissues is an adherent cell type. In further embodiments, the mammalian cells are, by way of non-limiting examples, liver cells, parenchymal cells, non-parenchymal cells, contractile or muscle cells (e.g., smooth muscle cells, and myoblasts), connective tissue cells (e.g., fibroblasts), bone marrow cells, endothelial cells, epithelial cells, vascular cells, blood cells, lymph cells, pericytes, mesothelial cells, stromal cells, undifferentiated cells (e.g., embryonic cells, stem cells, and progenitor cells), endoderm-derived cells, mesoderm-derived cells, ectoderm-derived cells, and combinations thereof.

In some embodiments, the engineered liver tissues include endothelial cells, such as human endothelial cells. In some embodiments, suitable endothelial cells originate from tissue including, by way of non-limiting example, liver tissue, blood, blood vessel, lymphatic vessel, tissue of the digestive tract, tissue of the genitourinary tract, adipose tissue, tissue of the respiratory tract, tissue of the reproductive system, bone marrow, and umbilical tissue.

In some embodiments, the cells are adult, differentiated cells. In further embodiments, "differentiated cells" are cells with a tissue-specific phenotype consistent with, for example, a hepatocyte or an endothelial at the time of isolation, wherein tissue-specific phenotype (or the potential to display the phenotype) is maintained from the time of isolation to the time of use. In other embodiments, the cells are adult, non-differentiated cells. In further embodiments, "non-differentiated cells" are cells that do not have, or have lost, the definitive tissue-specific traits. In some embodiments, non-differentiated cells include stem cells. In further embodiments, "stem cells" are cells that exhibit potency and self-renewal. Stem cells include, but are not limited to, totipotent cells, pluripotent cells, multipotent cells, oligopotent cells, unipotent cells, and progenitor cells. In various embodiments, stem cells are embryonic stem cells, adult stem cells, amniotic stem cells, and induced pluripotent stem cells. In yet other embodiments, the cells are a mixture of adult, differentiated cells and adult, non-differentiated cells.

In some embodiments, the engineered liver tissues include parenchymal cells are derived from multi-potent stem/progenitor cells. In various embodiments, the parenchymal cells are suitably derived from fetal mammalian liver tissue; embryonic stem cells (ESC); induced pluripotent stem cells (IPSC); adult stem/progenitor cells derived from the liver; and adult stem/progenitor cells derived from a tissue other than liver. In some embodiments, engineered liver tissues are derived from multi-potent stem/progenitor cells that have been either partially or fully differentiated into endodermal or hepatic phenotype prior to use in the fabrication of liver tissue constructs.

In some embodiments, the construct comprises stem/progenitor cells that have been exposed to one or more differentiation signals. In further embodiments, the differentiation signal comprises one or more of: biomechanical signals, soluble signals (e.g., a biochemical signal), and physical signals. Stem/progenitor cells are suitably exposed to one or more differentiation signals at many time points in the engineered liver tissue fabrication process. In some embodiments, the stem/progenitor cells were exposed to one or more differentiation signals before fabrication of the construct. In other embodiments, the stem/progenitor cells were exposed to one or more differentiation signals during fabrication of the construct. In yet other embodiments, the stem/progenitor cells were exposed to one or more differentiation signals after fabrication of the construct.

In various embodiments, the cell types and/or source of the cells are selected, configured, treated, or modulated based on a specific research goal or objective. In some embodiments, one or more specific cell types are selected, configured, treated, or modulated to facilitate investigation of a particular disease or condition. In some embodiments, one or more specific cell types are selected, configured, treated, or modulated to facilitate investigation of a disease or a condition of a particular subject. In some embodiments, one or more specific cell types are derived from two or more distinct human donors. In some embodiments, one or more specific cell types are derived from a particular vertebrate subject. In further embodiments, one or more specific cell types are derived from a particular mammalian subject. In still further embodiments, one or more specific cell types are derived from a particular human subject. In further embodiments, one or more specific cell types are derived from a particular subject with a specific phenotype associated with disease or tissue functionality. In some embodiments, the one or more cell types are a parenchymal cell as described herein, a non-parenchymal cell as described herein, or a combination thereof from a subject having a liver disorder. In some embodiments, the one or more cell types comprise diseased cells, non-diseased cells, or a combination thereof. In still further embodiments, the subject-specific cells are isolated from the target tissue of interest by way of biopsy or tissue sampling. In further embodiments, the subject-specific cells are utilized to fabricate tissue immediately after isolation. In other embodiments, the subject-specific cells are manipulated in vitro prior to use in the fabrication of three-dimensional tissues; wherein the manipulation includes one or more of: expansion, differentiation, directed differentiation, proliferation, exposure to proteins or nucleic acids, incorporation of genetic vectors, incorporation of genetic or non-genetic cell-tracing moieties, de-differentiation (i.e., generation of induced pluripotent stem cells or equivalents), cryopreservation. In some embodiments, subject-specific cells are isolated from a tissue other than the target tissue. In further embodiments, the subject-specific cells require differentiation into cell types of interest within the target tissue. In still further embodiments, subject-specific cells that require differentiation are differentiated prior to, during, or after fabrication into a three-dimensional structure.

Methods of Culturing Cells

The cell types used in the engineered liver tissues of the invention are suitably cultured in any manner known in the art. Methods of cell and tissue culturing are known in the art, and are described, for example, in Freshney, R., Culture of Animal Cells: A Manual of Basic Techniques, Wiley (1987), the contents of which are incorporated herein by reference for such information. General mammalian cell culture techniques, cell lines, and cell culture systems suitably used in conjunction with the present invention are also described in Doyle, A., Griffiths, J. B., Newell, D. G., (eds.) Cell and Tissue Culture: Laboratory Procedures, Wiley (1998), the contents of which are incorporated herein by reference for such information.

Appropriate growth conditions for mammalian cells in culture are well known in the art. Cell culture media generally include essential nutrients and, optionally, additional elements such as growth factors, salts, minerals, vitamins, platelet-rich plasma, etc., that are optionally selected according to the cell type(s) being cultured. In some embodiments, particular ingredients are selected to enhance cell growth, differentiation, secretion of specific proteins, etc. In general, standard growth media include Dulbecco's Modified Eagle Medium (DMEM) with 4 g/L glucose, supplemented with 1-20% fetal bovine serum (FBS), calf serum, or human serum, insulin (4 micrograms/mL), dexamethasone (1.0 micromolar), amphotericin B (0.25 micrograms/mL) and Glutamax (1×). Williams E media supplemented with insulin (1 g/L), sodium selenite (0.0067 g/L), transferrin (0.55 g/L), dexamethasone (1 micromolar), penicillin (100 U/mL), streptomycin (0.1 mg/mL), amphotericin B (0.25 micrograms/mL) and Glutamax (1×), or various other media known in the art. Preferably cells are cultured under sterile conditions in an atmosphere of 1-21% O2 and preferably 3-5% CO2, at a temperature at or near the body temperature of the animal of origin of the cell. For example, human cells are preferably cultured at approximately 37° C.

The cells are optionally cultured with cellular differentiation agents to induce differentiation of the cell along the desired line. For instance, cells are optionally cultured with growth factors, cytokines, etc. In some embodiments, the term "growth factor" refers to a protein, a polypeptide, or a complex of polypeptides, including cytokines that are produced by a cell and affect itself and/or a variety of other neighboring or distant cells. Typically growth factors affect the growth and/or differentiation of specific types of cells, either developmentally or in response to a multitude of physiological or environmental stimuli. Some, but not all, growth factors are hormones. Exemplary growth factors are insulin, insulin-like growth factor (IGF), nerve growth factor (NGF), vascular endothelial growth factor (VEGF), keratinocyte growth factor (KGF), fibroblast growth factors (FGFs), including basic FGF (bFGF), platelet-derived growth factors (PDGFs), including PDGF-AA and PDGF-AB, hepatocyte growth factor (HGF), transforming growth factor alpha (TGF-α), transforming growth factor beta (TGF-β), including TGFβ1 and TGFβ3, epidermal growth factor (EGF), granulocyte-macrophage colony-stimulating factor (GM-CSF), granulocyte colony-stimulating factor (G-CSF), interleukin-6 (IL-6), IL-8, and the like. Growth factors are discussed in, among other places, Molecular Cell Biology, Scientific American Books, Darnell et al., eds., 1986; Principles of Tissue Engineering, 2d ed., Lanza et al., eds., Academic Press, 2000. The skilled artisan will understand that any and all culture-derived growth factors in the conditioned media described herein are within the scope of the invention.

Bio-Ink and Multicellular Aggregates

Disclosed herein, in certain embodiments, are three-dimensional living tissues, including liver tissues/constructs, arrays thereof, and methods that comprise bioprinted cells. In some embodiments, cells are bioprinted by depositing or extruding bio-ink from a bioprinter. In some embodiments, "bio-ink" includes liquid, semi-solid, or solid compositions comprising a plurality of cells. In some embodiments, bio-ink comprises liquid or semi-solid cell solutions, cell suspensions, or cell concentrations. In further embodiments, a cell solution, suspension, or concentration comprises a liquid or semi-solid (e.g., viscous) carrier and a plurality of cells. In still further embodiments, the carrier is a suitable cell nutrient media, such as those described herein. In some embodiments, bio-ink comprises a plurality of cells that optionally cohere into multicellular aggregates prior to bioprinting. In further embodiments, bio-ink comprises a plurality of cells and is bioprinted to produce a specific planar and/or laminar geometry; wherein cohesion of the individual cells within the bio-ink takes place before, during and/or after bioprinting. In some embodiments, the bio-ink is produced by 1) collecting a plurality of cells in a fixed volume; wherein the cellular component(s) represent at least about 30% and at most 100% of the total volume. In some embodiments, bio-ink comprises semi-solid or solid multicellular aggregates or multicellular bodies. In further embodiments, the bio-ink is produced by 1) mixing a plurality of cells or cell aggregates and a biocompatible liquid or gel in a pre-determined ratio to result in bio-ink, and 2) compacting the bio-ink to produce the bio-ink with a desired cell density and viscosity. In some embodiments, the compacting of the bio-ink is achieved by centrifugation, tangential flow filtration ("TFF"), or a combination thereof. In some embodiments, the compacting of the bio-ink results in a composition that is extrudable, allowing formation of multicellular aggregates or multicellular bodies. In some embodiments, "extrudable" means able to be shaped by forcing (e.g., under pressure) through a nozzle or orifice (e.g., one or more holes or tubes). In some embodiments, the compacting of the bio-ink results from growing the cells to a suitable density. The cell density necessary for the bio-ink will vary with the cells being used and the tissue or organ being produced. In some embodiments, the cells of the bio-ink are cohered and/or adhered. In some embodiments, "cohere," "cohered," and "cohesion" refer to cell-cell adhesion properties that bind cells, multicellular aggregates, multicellular bodies, and/or layers thereof. In further embodiments, the terms are used interchangeably with "fuse," "fused," and "fusion." In some embodiments, the bio-ink additionally comprises support material, cell culture medium (or supplements thereof), extracellular matrix (or components thereof), cell adhesion agents, cell death inhibitors, anti-apoptotic agents, anti-oxidants, extrusion compounds, and combinations thereof.

In various embodiments, the cells are any suitable cell. In further various embodiments, the cells are vertebrate cells, mammalian cells, human cells, or combinations thereof. In some embodiments, the type of cell used in a method disclosed herein depends on the type of construct or tissue being produced. In some embodiments, the bio-ink comprises one type of cell (also referred to as a "homogeneous" or "monotypic" bio-ink). In some embodiments, the bio-ink comprises more than one type of cell (also referred to as a "heterogeneous" or "polytypic" bio-ink).

Cell Culture Media

In some embodiments, the bio-ink comprises a cell culture medium. The cell culture medium is any suitable medium. In various embodiments, suitable cell culture media include, by way of non-limiting examples, Dulbecco's Phosphate Buffered Saline, Earle's Balanced Salts, Hanks' Balanced Salts, Tyrode's Salts, Alsever's Solution, Gey's Balanced Salt Solution, Kreb's-Henseleit Buffer Modified, Kreb's-Ringer Bicarbonate Buffer, Puck's Saline, Dulbecco's Modified Eagle's Medium, Dulbecco's Modified Eagle's Medium/Nutrient F-12 Ham, Nutrient Mixture F-10 Ham (Ham's F-10), Medium 199, Minimum Essential Medium Eagle, RPMI-1640 Medium, Ames' Media, BGJb Medium (Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, or combinations thereof. In some embodiments, the cell culture medium is modified or supplemented. In some embodiments, the cell culture medium further comprises albumin, selenium, transferrins, fetuins, sugars, amino acids, vitamins, growth factors, cytokines, hormones, antibiotics, lipids, lipid carriers, cyclodextrins, platelet-rich plasma, or a combination thereof.

Extracellular Matrix

In some embodiments, the bio-ink further comprises one or more components of an extracellular matrix or derivatives thereof. In some embodiments, "extracellular matrix" includes proteins that are produced by cells and transported out of the cells into the extracellular space, where they serve as a support to hold tissues together, to provide tensile strength, and/or to facilitate cell signaling. Examples, of extracellular matrix components include, but are not limited to, collagens, fibronectin, laminins, hyaluronates, elastin, and proteoglycans. For example, in some embodiments, the multicellular aggregates contain various ECM proteins (e.g., gelatin, fibrinogen, fibrin, collagens, fibronectin, laminins, elastin, and/or proteoglycans). The ECM components or derivatives of ECM components are optionally added to the cell paste used to form the multicellular aggregate. The ECM components or derivatives of ECM components added to the cell paste are optionally purified from a human or animal source, or produced by recombinant methods known in the art. Alternatively, the ECM components or derivatives of ECM components are naturally secreted by the cells in the elongate cellular body, or the cells used to make the elongate cellular body are optionally genetically manipulated by any suitable method known in the art to vary the expression level of one or more ECM components or derivatives of ECM components and/or one or more cell adhesion molecules or cell-substrate adhesion molecules (e.g., selectins, integrins, immunoglobulins, and adherins). In some embodiments, the ECM components or derivatives of ECM components promote cohesion of the cells in the multicellular aggregates. For example, gelatin and/or fibrinogen is suitably added to the cell paste, which is used to form multicellular aggregates. The fibrinogen is converted to fibrin by the addition of thrombin.

In some embodiments, the bio-ink further comprises an agent that encourages cell adhesion.

Figure 15:
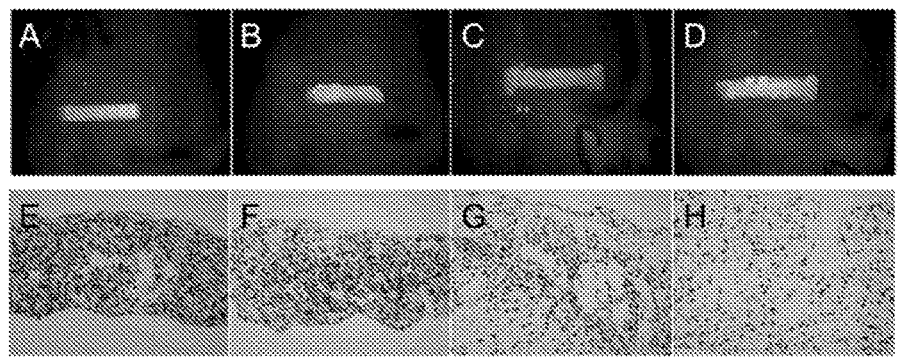
FIG. 15 is a non-limiting example of stimulation of bioprinted hepatic stellate cell tissues with TGF-β1. Incubation of bioprinted hepatic stellate cell sheets with increasing concentrations of TGF-β1 (0, 1, 10, 50 ng/mL), results in changes in gross observation of the bioprinted tissues as increases in cytokine concentration lead to increases in tissue outgrowth formation (A-D, 0-50 ng/mL). Trichrome staining of tissue sections from bioprinted hepatic stellate-containing tissues reveals increases in collagen deposition and construct size and dramatic decreases in cell density (E-H, 0-50 ng/mL).

In some embodiments, the bio-ink further comprises an agent that inhibits cell death (e.g., necrosis, apoptosis, or autophagocytosis). In some embodiments, the bio-ink further comprises an anti-apoptotic agent. Agents that inhibit cell death include, but are not limited to, small molecules, antibodies, peptides, peptibodies, or combination thereof. In some embodiments, the agent that inhibits cell death is selected from: anti-TNF agents, agents that inhibit the activity of an interleukin, agents that inhibit the activity of an interferon, agents that inhibit the activity of an GCSF (granulocyte colony-stimulating factor), agents that inhibit the activity of a macrophage inflammatory protein, agents that inhibit the activity of TGF-B (transforming growth factor B) (see, e.g., FIGS. 15 and 16), agents that inhibit the activity of an MMP (matrix metalloproteinase), agents that inhibit the activity of a caspase, agents that inhibit the activity of the MAPK/JNK signaling cascade, agents that inhibit the activity of a Src kinase, agents that inhibit the activity of a JAK (Janus kinase), or a combination thereof. In some embodiments, the bio-ink comprises an anti-oxidant. In some embodiments, the bio-ink comprises oxygen-carriers or other cell-specific nutrients.

Extrusion Compounds

In some embodiments, the bio-ink further comprises an extrusion compound (i.e., a compound that modifies the extrusion properties of the bio-ink). Examples of extrusion compounds include, but are not limited to gels, hydrogels, peptide hydrogels, amino acid-based gels, surfactant polyols (e.g., Pluronic F-127 or PF-127), thermo-responsive polymers, hyaluronates, alginates, extracellular matrix components (and derivatives thereof), collagens, gelatin, other biocompatible natural or synthetic polymers, nanofibers, and self-assembling nanofibers. In some embodiments, extrusion compounds are removed after bioprinting by physical, chemical, or enzymatic means.

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums (e.g., tragacanth). In some embodiments, single-phase gels are generally aqueous, but will also be made using alcohols and oils. Two-phase gels consist of a network of small discrete particles.

Gels, in some cases, are classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

Suitable hydrogels include those derived from collagen, hyaluronate, hyaluronan, fibrin, alginate, agarose, chitosan, and combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, Novo-Gel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

In some embodiments, hydrogel-based extrusion compounds are thermoreversible gels (also known as thermoresponsive gels or thermogels). In some embodiments, a suitable thermoreversible hydrogel is not a liquid at room temperature. In specific embodiments, the gelation temperature (Tgel) of a suitable hydrogel is about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., including increments therein. In certain embodiments, the Tgel of a suitable hydrogel is about 10° C. to about 40° C. In further embodiments, the Tgel of a suitable hydrogel is about 20° C. to about 30° C. In some embodiments, the bio-ink (e.g., comprising hydrogel, one or more cell types, and other additives, etc.) described herein is not a liquid at room temperature. In some embodiments, a suitable thermoreversible hydrogel is not a liquid at mammalian body temperature. In specific embodiments, the gelation temperature (Tgel) of a suitable hydrogel is about 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 41° C., 43° C., 44° C., 45° C., 46° C., 47° C., 48° C., 49° C., 50° C., 51° C., 52° C., including increments therein. In certain embodiments, the Tgel of a suitable hydrogel is about 22° C. to about 52° C. In further embodiments, the Tgel of a suitable hydrogel is about 32° C. to about 42° C. In some embodiments, the bio-ink (e.g., comprising hydrogel, one or more cell types, and other additives, etc.) described herein is not a liquid at mammalian body temperature. In specific embodiments, the gelation temperature (Tgel) of a bio-ink described herein is about 10° C., about 15° C., about 20° C., about 25° C., about 30° C., about 35° C., about 40° C., about 45° C., about 50° C., about 55° C., including increments therein. In a specific embodiment, the Tgel of a bio-ink described herein is about 10° C. to about 15° C. In another specific embodiment, the Tgel of a bio-ink described herein is about 15° C. to about 20° C. In another specific embodiment, the Tgel of a bio-ink described herein is about 20° C. to about 25° C. In another specific embodiment, the Tgel of a bio-ink described herein is about 25° C. to about 30° C. In another specific embodiment, the Tgel of a bio-ink described herein is about 30° C. to about 35° C. In another specific embodiment, the Tgel of a bio-ink described herein is about 35° C. to about 40° C. In another specific embodiment, the Tgel of a bio-ink described herein is about 40° C. to about 45° C. In another specific embodiment, the Tgel of a bio-ink described herein is about 45° C. to about 50° C.

Polymers composed of polyoxypropylene and polyoxyethylene form thermoreversible gels when incorporated into aqueous solutions. These polymers have the ability to change from the liquid state to the gel state at temperatures maintainable in a bioprinter apparatus. The liquid state-to-gel state phase transition is dependent on the polymer concentration and the ingredients in the solution.

Poloxamer 407 (Pluronic F-127 or PF-127 or Lutrol) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer is optionally further purified by suitable methods that will enhance gelation properties of the polymer. It contains approximately 70% ethylene oxide, which accounts for its hydrophilicity. It is one of the series of poloxamer ABA block copolymers. PF-127 has good solubilizing capacity, low toxicity and is, therefore, considered a suitable extrusion compound.

In some embodiments, the viscosity of the hydrogels and bio-inks presented herein is measured by any means described. For example, in some embodiments, an LVDV-II+CP Cone Plate Viscometer and a Cone Spindle CPE-40 is used to calculate the viscosity of the hydrogels and bio-inks. In other embodiments, a Brookfield (spindle and cup) viscometer is used to calculate the viscosity of the hydrogels and bio-inks. In some embodiments, the viscosity ranges referred to herein are measured at room temperature. In other embodiments, the viscosity ranges referred to herein are measured at body temperature (e.g., at the average body temperature of a healthy human).

In further embodiments, the hydrogels and/or bio-inks are characterized by having a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise.

In some embodiments, the bio-ink comprises cells and extrusion compounds suitable for continuous bioprinting. In specific embodiments, the bio-ink has a viscosity of about 1500 mPa·s. In some embodiments, a mixture of Pluronic F-127 and cellular material is suitable for continuous bioprinting. Such a bio-ink is suitably prepared by dissolving Pluronic F-127 powder by continuous mixing in cold (4° C.) phosphate buffered saline (PBS) over 48 hours to 30% (w/v). Pluronic F-127 is also suitably dissolved in water. In some embodiments, cells are cultivated and expanded using standard sterile cell culture techniques. In further embodiments, the cells are pelleted at 200 g for example, and re-suspended in the 30% Pluronic F-127 and aspirated into a reservoir affixed to a bioprinter where it is, in some embodiments, allowed to solidify at a gelation temperature from about 10 to about 25° C. Gelation of the bio-ink prior to bioprinting is optional. The bio-ink, including bio-ink comprising Pluronic F-127 is optionally dispensed as a liquid.

In various embodiments, the concentration of Pluronic F-127 is any value with suitable viscosity and/or cytotoxicity properties. In some embodiments, a suitable concentration of Pluronic F-127 is able to support weight while retaining its shape when bioprinted. In some embodiments, the concentration of Pluronic F-127 is about 10%, about 15%, about 20%, about 25%, about 30%, about 35%, about 40%, about 45%, or about 50%. In some embodiments, the concentration of Pluronic F-127 is between about 30% and about 40%, or between about 30% and about 35%.

In some embodiments, the concentration of gelatin is 6% and the concentration of alginate is 0.5% in the extrusion compound or excipient. In other embodiments, the concentration of gelatin is 4% and the concentration of alginate is 2% in the extrusion compound or excipient.

In some embodiments, the non-cellular components of the bio-ink (e.g., extrusion compounds, etc.) are removed prior to use. In further embodiments, the non-cellular components are, for example, hydrogels, peptide hydrogels, amino acid-based gels, surfactant polyols, thermo-responsive polymers, hyaluronates, alginates, collagens, or other biocompatible natural or synthetic polymers. In still further embodiments, the non-cellular components are removed by physical, chemical, or enzymatic means. In some embodiments, a proportion of the non-cellular components remain associated with the cellular components at the time of use.

In some embodiments, the cells are pre-treated to increase cellular interaction. For example, cells are suitably incubated inside a centrifuge tube after centrifugation in order to enhance cell-cell interactions prior to shaping the bio-ink.

Exemplary Cell Ratios

In some embodiments, the bio-ink comprises multicellular bodies, which further comprise non-parenchymal liver cells (e.g. endothelial cells, hepatic stellate cells, Kupffer cells). In further embodiments, the ratio of endothelial cells to hepatic stellate cells to Kupffer cells is any suitable ratio. In further embodiments, the ratio of endothelial cells to hepatic stellate cells to Kupffer cells is about 90:10:0 to about 10:90:0. In still further embodiments, the ratio of endothelial cells to hepatic stellate cells to Kupffer cells is 45:45:10.

In some embodiments, the bio-ink comprises multicellular bodies, which further comprise hepatocytes (e.g., primary hepatocytes, HepG2 or HepaRG) and additional cell types at a ratio of 100:0. In further embodiments, the ratio of hepatocytes to additional, non-parenchymal cell types (e.g., endothelial cells) is 95:5. In further embodiments, the ratio of hepatocytes to additional, non-parenchymal cell types (e.g., endothelial cells, stellate cells) is 50:50. In still further embodiments, the ratio of parenchymal to non-parenchymal cells (e.g., endothelial cells, stellate cells, Kupffer cells) is 50:35:10:5, 55:40:5:5, or 50-55:35-40:10-5:10-5.

Self-Sorting of Cells

In some embodiments, multicellular aggregates used to form the construct or tissue comprises all cell types to be included in the engineered tissue (e.g., hepatocytes, endothelial cells, hepatic stellate cells and Kupffer cells); in such an example each cell type migrates to an appropriate position (e.g., during maturation) to form the engineered tissue, such as an engineered liver tissue. In other embodiments, the multicellular aggregates used to form the structure comprises fewer than all the cell types to be included in the engineered tissue. In some embodiments, cells of each type are uniformly distributed within a multicellular aggregates, or region or layer of the tissue. In other embodiments, cells of each type localize to particular regions within a multicellular aggregate or layers or regions of the tissue.

For example, in the case of an engineered liver tissue comprising hepatocytes, endothelial cells, hepatic stellate cells and Kupffer cells, in a suitable ratio (e.g., 70-80:15-10:10-5:5, such as, for example, 70:15:10:5, 80:10:5:5, 75:15:5:5, or 70:20:5:5), neighboring, bioprinted cohered polytypic bio-ink units fuse. During maturation, endothelial cells localize to some extent to both the periphery and core of the construct and organize into microvascular structures. In some embodiments, localization of cell types within a construct mimics the layered structure of in vivo or ex vivo mammalian tissues.

Pre-Formed Scaffold

In some embodiments, disclosed herein are engineered, implantable tissues and organs that are free or substantially free of any pre-formed scaffold. In further embodiments, "scaffold" refers to synthetic scaffolds such as polymer scaffolds and porous hydrogels (including, e.g., a biopaper into which a cell is embedded), non-synthetic scaffolds such as pre-formed extracellular matrix layers, dead cell layers, and decellularized tissues, and any other type of pre-formed scaffold that is integral to the physical structure of the engineered tissue and/or organ and not removed from the tissue and/or organ. In still further embodiments, decellularized tissue scaffolds include decellularized native tissues or decellularized cellular material generated by cultured cells in any manner; for example, cell layers that are allowed to die or are decellularized, leaving behind the ECM they produced while living.

In some embodiments, the engineered liver tissues/constructs and arrays thereof do not utilize any pre-formed scaffold, e.g., for the formation of the tissue, any layer of the tissue, or formation of the tissue's shape. As a non-limiting example, the engineered liver tissues of the present invention do not utilize any pre-formed, synthetic scaffolds such as polymer scaffolds, pre-formed extracellular matrix layers, or any other type of pre-formed scaffold at the time of manufacture or at the time of use. In some embodiments, the engineered liver tissues are substantially free of any pre-formed scaffolds. In further embodiments, the cellular components of the tissues contain a detectable, but trace or trivial amount of scaffold, e.g., less than 2.0%, less than 1.0%, or less than 0.5% of the total composition. In still further embodiments, trace or trivial amounts of scaffold are insufficient to affect long-term behavior of the tissue, or array thereof, or interfere with its primary biological function. In additional embodiments, scaffold components are removed post-printing, by physical, chemical, or enzymatic methods, yielding an engineered tissue that is free or substantially-free of scaffold components.

In some embodiments, the engineered liver tissues free, or substantially free, of pre-formed scaffold disclosed herein are in stark contrast to those developed with certain other methods of tissue engineering in which a scaffolding material is first formed, and then cells are seeded onto the scaffold, and subsequently the cells proliferate to fill and take the shape of the scaffold for example. In one aspect, the methods of bioprinting described herein allow production of viable and useful tissues that are free or substantially free of pre-formed scaffold. In another aspect, the cells of the invention are, in some embodiments, held in a desired three-dimensional shape using a confinement material. The confinement material is distinct from a scaffold at least in the fact that the confinement material is temporary and/or removable from the cells and/or tissue.

Arrays

In some embodiments, disclosed herein are arrays of engineered liver tissues/constructs. In some embodiments, an "array" is a scientific tool including an association of multiple elements spatially arranged to allow a plurality of tests to be performed on a sample, one or more tests to be performed on a plurality of samples, or both. In some embodiments, the arrays are adapted for, or compatible with, screening methods and devices, including those associated with medium- or high-throughput screening. In further embodiments, an array allows a plurality of tests to be performed simultaneously. In further embodiments, an array allows a plurality of samples to be tested simultaneously. In some embodiments, the arrays are cellular microarrays. In further embodiments, a cellular microarray is a laboratory tool that allows for the multiplex interrogation of living cells on the surface of a solid support. In other embodiments, the arrays are tissue microarrays. In further embodiments, tissue microarrays include a plurality of separate tissues or tissue samples assembled in an array to allow the performance of multiple biochemical, metabolic, molecular, or histological analyses.

Figure 16:
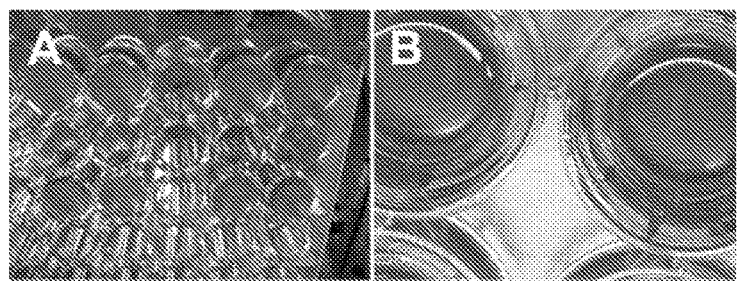
FIG. 16 is a non-limiting example of bioprinting in multi-well formats. Bioprinted tissue constructs are generated in multi-well plates (A) or within multi-well culture inserts (B), which are optionally placed in an appropriate multi-well plate for long-term maintenance and maturation. Here, tissue constructs were bioprinted in a 48-well polystyrene plate (A) and on the porous membrane of a 6-well cell culture insert (B).

In some embodiments, the engineered liver tissues/constructs each exist in a well of a biocompatible multi-well container (see, e.g., FIG. 16). In some embodiments, each tissue is placed into a well. In other embodiments, each tissue is bioprinted into a well. In further embodiments, the wells are coated. In various further embodiments, the wells are coated with one or more of: a biocompatible hydrogel, one or more proteins, one or more chemicals, one or more peptides, one or more antibodies, and one or more growth factors, including combinations thereof. In some embodiments, the wells are coated with NovoGel™. In other embodiments, the wells are coated with agarose. In some embodiments, each tissue exists on a porous, biocompatible membrane within a well of a biocompatible multi-well container. In some embodiments, each well of a multi-well container contains two or more tissues.

In some embodiments, the engineered liver tissues/constructs are secured to a biocompatible surface on one or more sides. Many methods are suitable to secure a tissue to a biocompatible surface. In various embodiments, a tissue is suitably secured to a biocompatible surface, for example, along one or more entire sides, only at the edges of one or more sides, or only at the center of one or more sides. In various further embodiments, a tissue is suitably secured to a biocompatible surface with a holder or carrier integrated into the surface or associated with the surface. In various further embodiments, a tissue is suitably secured to a biocompatible surface with one or more pinch-clamps or plastic nubs integrated into the surface or associated with the surface. In some embodiments, a tissue is suitably secured to a biocompatible surface by cell-attachment to a porous membrane. In some embodiments, the engineered liver tissues/constructs are held in an array configuration by affixation to a biocompatible surface on one or more sides. In further embodiments, the tissue is affixed to a biocompatible surface on 1, 2, 3, 4, or more sides. In some embodiments, the biocompatible surface any surface that does not pose a significant risk of injury or toxicity to the tissue or an organism contacting the tissue. In further embodiments, the biocompatible surface is any surface suitable for traditional tissue culture methods. Suitable biocompatible surfaces include, by way of non-limiting examples, treated plastics, membranes, porous membranes, coated membranes, coated plastics, metals, coated metals, glass, treated glass, and coated glass, wherein suitable coatings include hydrogels, ECM components, chemicals, proteins, etc., and coatings or treatments provide a means to stimulate or prevent cell and tissue adhesion to the biocompatible surface.

In some embodiments, securing of an engineered tissue to a biocompatible surface on one or more sides facilitates subjecting the tissue to shear force, caused by fluid flow. In further embodiments, the engineered liver tissues/constructs, are subjected to shear force, caused by fluid flow. In various embodiments, the engineered liver tissues are subjected to shear force on 1, 2, 3, 4, or more sides. In further embodiments, the engineered liver tissues/constructs are subjected to recirculation, perfusion, or agitation of the liquid nutrients that contact the tissues on one or more exposed surfaces.

In some embodiments, the arrays of engineered tissues, including liver tissues/constructs, comprise an association of two or more elements. In various embodiments, the arrays comprise an association of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 elements, including increments therein. In further embodiments, each element comprises one or more cells, multicellular aggregates, tissues, organs, or combinations thereof.

In some embodiments, the arrays of engineered tissues, including liver tissues/constructs, comprise multiple elements spatially arranged in a pre-determined pattern. In further embodiments, the pattern is any suitable spatial arrangement of elements. In various embodiments, patterns of arrangement include, by way of non-limiting examples, a two-dimensional grid, a three-dimensional grid, one or more lines, arcs, or circles, a series of rows or columns, and the like. In further embodiments, the pattern is chosen for compatibility with medium- or high-throughput biological assay or screening methods or devices.

In various embodiments, the cell types and/or source of the cells used to fabricate one or more tissues in an array are selected based on a specific research goal or objective. In further various embodiments, the specific tissues in an array are selected based on a specific research goal or objective. In some embodiments, one or more specific engineered liver tissues are included in an array to facilitate investigation of a particular disease or condition. In some embodiments, one or more specific engineered liver tissues are included in an array to facilitate investigation of a disease or a condition of a particular subject. In further embodiments, one or more specific engineered liver tissues within the array are generated with one or more cell types derived from two or more distinct human donors. In some embodiments, each tissue within the array is substantially similar with regard to cell types, sources of cells, layers of cells, ratios of cells, and methods of construction, size, shape, and the like. In other embodiments, one or more of the tissues within the array is unique with regard to cell types, sources of cells, layers of cells, ratios of cells, methods of construction, size, shape, and the like. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, is/are unique. In other various embodiments, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, is/are unique.

In some embodiments, each tissue within the array is maintained independently in culture. In further embodiments, the culture conditions of each tissue within the array are such that they are isolated from the other tissues and cannot exchange media or factors soluble in the media. In other embodiments, two or more individual tissues within the array exchange soluble factors. In further embodiments, the culture conditions of two or more individual tissues within the array are such that they exchange media and factors soluble in the media with other tissues. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, exchange media and/or soluble factors. In other various embodiments, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, exchange media and/or soluble factors.

In Vitro Assays

In some embodiments, the engineered liver tissues and arrays disclosed herein are for use in in vitro assays. In some embodiments, an "assay" is a procedure for testing or measuring the presence or activity of a substance (e.g., a chemical, molecule, biochemical, drug, etc.) in an organic or biologic sample (e.g., cell aggregate, tissue, organ, organism, etc.). In further embodiments, assays include qualitative assays and quantitative assays. In still further embodiments, a quantitative assay measures the amount of a substance in a sample.

In various embodiments, the engineered liver tissues and arrays are for use in, by way of non-limiting examples, image-based assays, measurement of secreted proteins, expression of markers, and production of proteins. In various further embodiments, the engineered liver tissue and arrays are for use in assays to detect or measure one or more of: molecular binding (including radioligand binding), molecular uptake, activity (e.g., enzymatic activity and receptor activity, etc.), gene expression, protein expression, receptor agonism, receptor antagonism, cell signaling, apoptosis, chemosensitivity, transfection, cell migration, chemotaxis, cell viability, cell proliferation, safety, efficacy, metabolism, toxicity, infectivity, and abuse liability.

In some embodiments, the engineered liver tissues and arrays are for use in immunoassays. In further embodiments, immunoassays are competitive immunoassays or noncompetitive immunoassays. In a competitive immunoassay, for example, the antigen in a sample competes with labeled antigen to bind with antibodies and the amount of labeled antigen bound to the antibody site is then measured. In a noncompetitive immunoassay (also referred to as a "sandwich assay"), for example, antigen in a sample is bound to an antibody site; subsequently, labeled antibody is bound to the antigen and the amount of labeled antibody on the site is then measured.

In some embodiments, the engineered liver tissue and arrays are for use in enzyme-linked immunosorbent assays (ELISA). In further embodiments, an ELISA is a biochemical technique used to detect the presence of an antibody or an antigen in a sample. In ELISA, for example, at least one antibody with specificity for a particular antigen is utilized. By way of further example, a sample with an unknown amount of antigen is immobilized on a solid support (e.g., a polystyrene microtiter plate) either non-specifically (via adsorption to the surface) or specifically (via capture by another antibody specific to the same antigen, in a "sandwich" ELISA). By way of still further example, after the antigen is immobilized, the detection antibody is added, forming a complex with the antigen. The detection antibody is, for example, covalently linked to an enzyme, or is itself detected by a secondary antibody that is linked to an enzyme through bioconjugation.

For example, in some embodiments, an array, microarray, or chip of cells, multicellular aggregates, or tissues is used for drug screening or drug discovery. In further embodiments, an array, microarray, or chip of tissues is used as part of a kit for drug screening or drug discovery. In some embodiments, each engineered liver tissue/construct exists within a well of a biocompatible multi-well container, wherein the container is compatible with one or more automated drug screening procedures and/or devices. In further embodiments, automated drug screening procedures and/or devices include any suitable procedure or device that is computer or robot-assisted.

In further embodiments, arrays for drug screening assays or drug discovery assays are used to research or develop drugs potentially useful in any therapeutic area. In still further embodiments, suitable therapeutic areas include, by way of non-limiting examples, infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, and immunology.

In some embodiments, the engineered liver tissue and arrays are for use in cell-based screening. In further embodiments, the cell-based screening is for one or more infectious diseases such as viral infection or parasitic infection (e.g., *plasmodium* infection, etc.). In further embodiments, the cell-based screening is for liver fibrosis (e.g., cirrhosis). In further embodiments, the cell-based screening is for liver cancer. In further embodiments, the cell-based screening is for liver steatosis (e.g., fatty liver). In further embodiments, the cell-based screening is for one or more metabolic deficiencies. In further embodiments, the cell-based screening is for one or more protein deficiencies. In other embodiments, the engineered liver tissues and arrays are for use in the study of cancer initiation, progression, or metastasis. In still further embodiments, the engineered liver tissues and arrays are for use in the study of the interaction of other cell types, such as cancer cells, pathogen-bearing cells, pathogenic cells, immune cells, blood-derived cells, or stem/progenitor cells, with liver tissue and the cells comprising liver tissue.

In some embodiments, the constructs or arrays thereof are for use in assessing the performance of biologics, including antibodies, mammalian cells, bacteria, biologically-active proteins, hormones, etc. In some embodiments the construct or arrays thereof are for use to detect, quantify, and study immunologic sampling by Kupffer and stellate cells, including the effects of gram-negative or gram-positive antigen-stimulated signaling from Kupffer or stellate cells to bordering hepatocytes (e.g., response to lipopolysaccharide (LPS)). In some embodiments, the constructs or arrays thereof are useful for the production of hepatotrophic viruses, including HBV and HCV. In further embodiments, the constructs or arrays thereof are used as a vehicle for production of *Plasmodium* spp. (a parasite) in the exo-erythrocytic form. In still further embodiments, liver construct-derived *Plasmodium* are utilized in comparative in vitro assays to identify effective therapies for exo-erythrocytic forms of the parasite. In other embodiments, the construct or arrays thereof are utilized as anti-host therapies for Hepatitis C Virus (HCV) or *Plasmodium*, including the conduct of anti-host antibody studies. In other embodiments, the liver constructs or arrays thereof are useful in the study of cancer initiation, progression, or metastasis. In other embodiments, the liver constructs or arrays thereof are useful in the study of cell-cell and cell-tissue interactions between the mammalian liver cells/tissue comprising the construct and one or more additional cell types, including but not limited to pathogen-bearing cells, living pathogenic cells, cancer cells, immune cells, blood cells, stem/progenitor cells, or genetically-manipulated cells.

In some embodiments, the array comprises engineered liver tissue constructs and additional tissue constructs. In further embodiments, the liver tissue construct is in direct contact with an additional tissue construct on one or more surfaces. In still further embodiments, the liver tissue is connected to one or more additional tissues constructs or cells via a fluid path or common fluid reservoir. In still further embodiments, the liquid media that contacts the engineered liver tissue construct contains living mammalian cells such as immune cells, blood-derived cells, or tumor-derived cells. In other embodiments, the liquid media that contacts the engineered liver tissue construct contains bacteria, viruses, parasites, or other pathogens. In some embodiments, the engineered liver tissue and arrays are for use as vehicle to propagate hepatotrophic viruses for three dimensional structural studies including X-ray or cryo-EM.

Extracorporeal Support

In some embodiments, the engineered liver tissues comprise a plurality of layers, each layer comprising cylindrical bio-ink, the bio-ink axially-aligned substantially in parallel, the bio-ink comprising parenchymal liver cells; and optionally, non-parenchymal cells among the cylindrical bio-ink; and optionally, void spaces or perfusable channels among the cylindrical bio-ink. In further embodiments, an engineered liver tissue is used to provide extracorporeal support to a subject in need thereof. In still further embodiments, blood is passed over or through the construct to filter the blood and supplement the subjects liver function.

Figure 17:
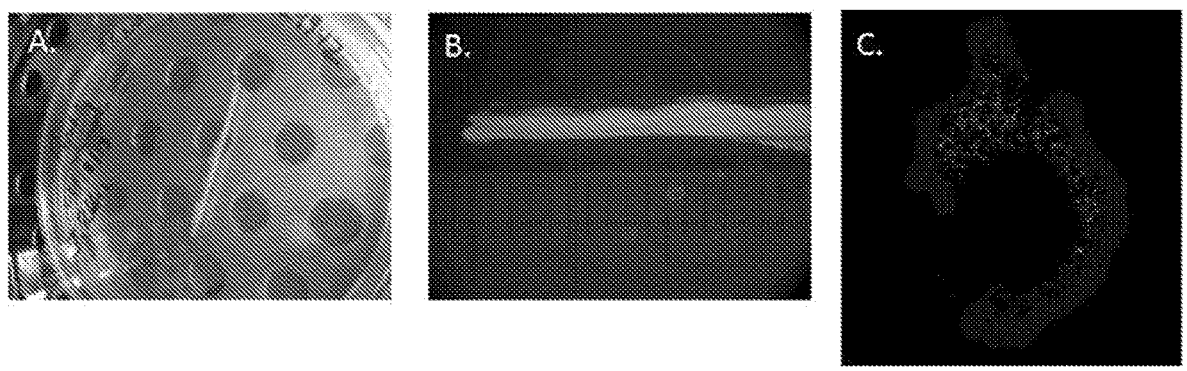
FIG. 17 is a non-limiting example of bio-printed hepatic tubular structure designed and printed for extracorporeal support (A). 40 mm length bio-ink cylinders comprising 70% HepG2/25% HUVEC/5% Hepatic Stellate were bioprinted and conditioned (B). A channel was created in the center of the structure by use of a removable, bio-inert hydrogel (C).
Figure 18:
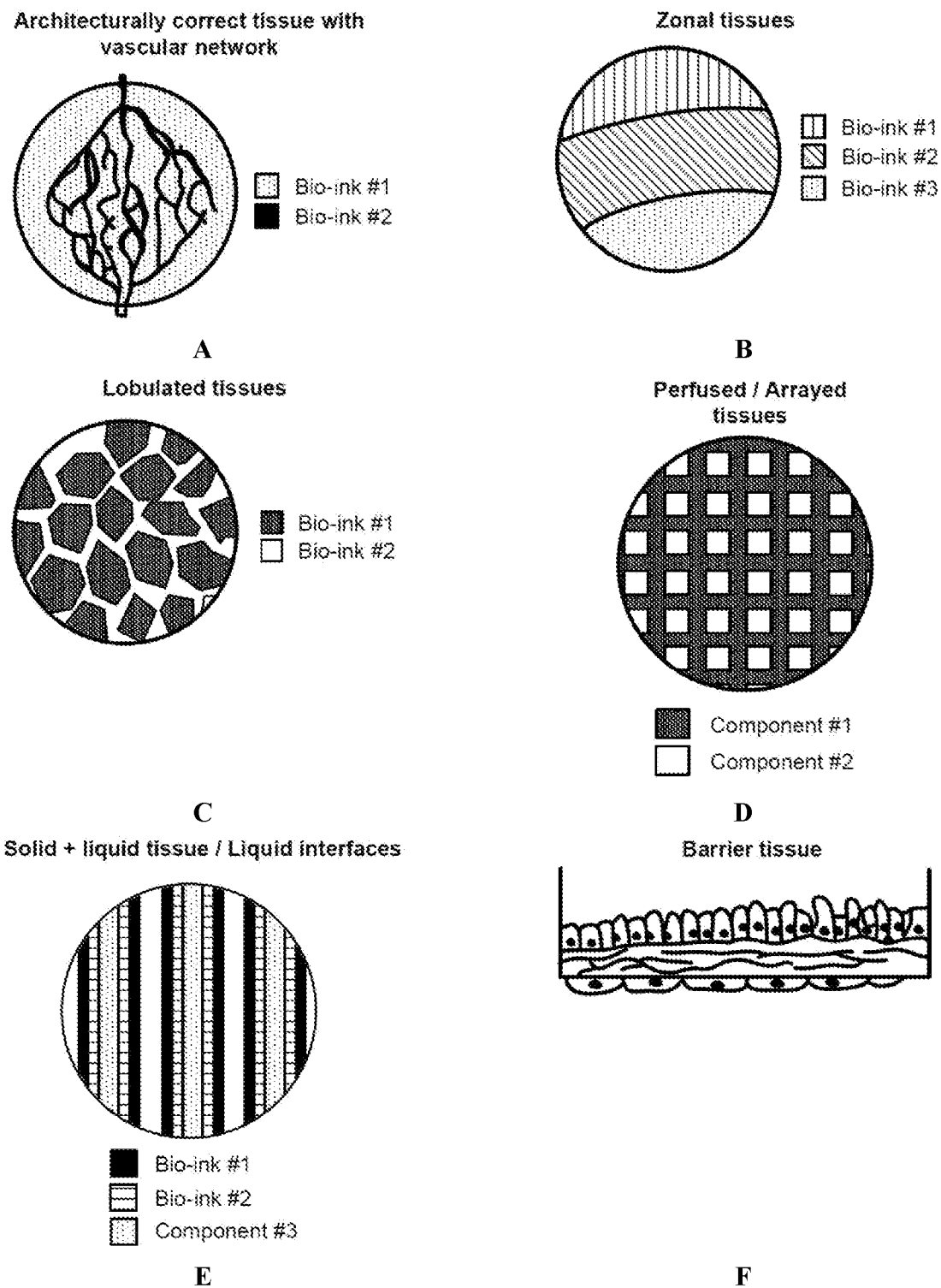
FIG. 18 is a series of non-limiting examples of planar and laminar geometries, including combinations thereof that are compatible with the methods of construction described herein, and reproduce architectural or spatial elements of native tissue architecture and biology. Exemplary geometries include an architecturally correct tissue with a vascular network (A), a zonal tissue (B), a lobulated tissue (C), a perfused/arrayed tissue (D), a tissue with a solid+liquid/liquid interface (E), a barrier tissue (F), and a layered tissue with laminar geometry (G).
Figure 18:
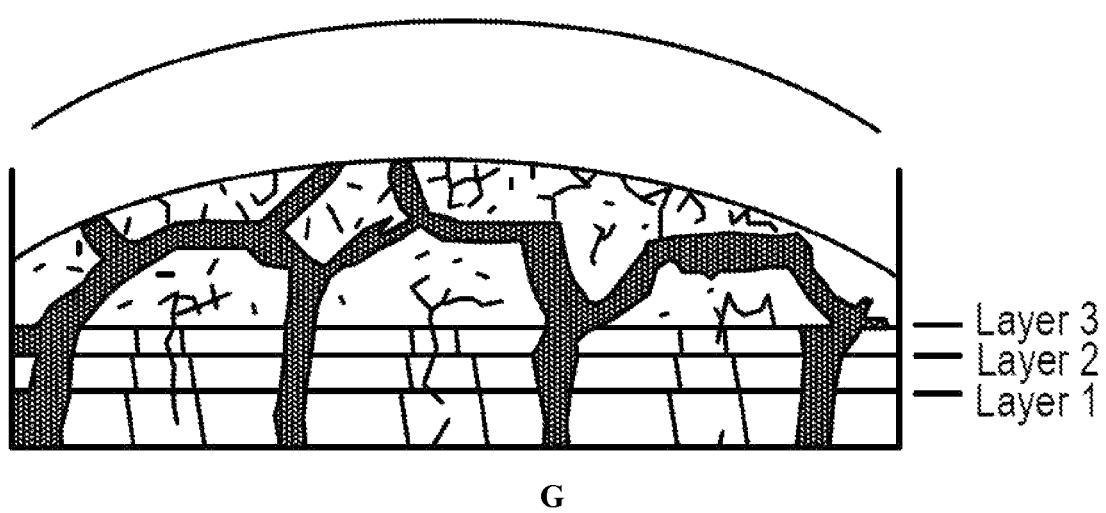

Referring to FIG. 17, in a particular embodiment, a bioprinted liver structure is designed for providing extracorporeal support (A). In this embodiment, a bioprinted liver structure is composed of a plurality of parenchymal cell cylinders (B). The structure also includes non-parenchymal cells and filler bodies to create compartments and/or channels through which perfusion or flow could be achieved (C).

Figure 19:
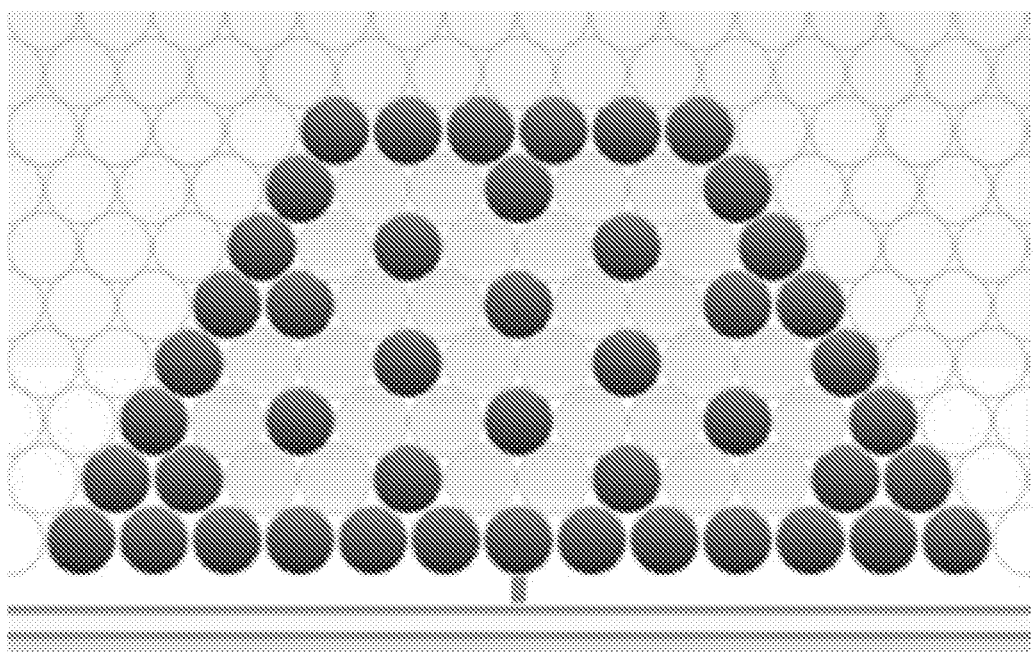
FIG. 19 is a non-limiting schematic representation of an extracorporeal hepatic device containing repeating tubular structures with void spaces (depicted as occupied by temporary filler bodies; dark circles) at regular intervals allowing perfusion across and/or through the engineered liver tissue.

Referring to FIG. 19, in a particular embodiment, a bioprinted liver structure is used as an extracorporeal hepatic device containing repeating tubular structures with void spaces (depicted occupied by temporary filler bodies) at regular intervals allowing perfusion across and/or through the engineered liver tissue.

Methods

Disclosed herein, in some embodiments, are methods for constructing living, three-dimensional liver tissue constructs, the methods comprising the steps of bioprinting bio-ink comprising at least one liver cell type into or onto a form, and fusing of the bio-ink into a living, three-dimensional tissue liver construct. In further embodiments, the tissue construct is for in vitro use.

Also disclosed herein, in some embodiments, are methods of constructing tissues, including engineered liver tissues, comprising the steps of: preparing cohered multicellular aggregates comprising either parenchymal or parenchymal and non-parenchymal cells; placing said cohered multicellular aggregates onto a support; and incubating said multicellular aggregates to allow them to cohere and form an engineered liver tissue; wherein said incubation has a duration of about 1 hours to about 30 days. In some embodiments, the methods utilize bioprinting. In further embodiments, the methods produce engineered liver tissues free or substantially free of any pre-formed scaffold at the time of use.

Also disclosed herein, in some embodiments, are methods of constructing living, three-dimensional liver tissues comprising the steps of: preparing one or more cohered multicellular aggregates comprising mammalian liver cells; placing said one or more cohered multicellular aggregates onto a support; applying, to said one or more cohered multicellular aggregates, one or more of: a layer of a first type of mammalian cells on one or more external surfaces; a layer of a second type of mammalian cells on one or more external surfaces; and incubating said one or more multicellular aggregates to allow them to cohere and to form a tissue; wherein said incubation has a duration of about 1 hour to about 30 days. In some embodiments, the methods utilize bioprinting. In further embodiments, the methods produce engineered liver tissues, free or substantially free of any pre-formed scaffold at the time of use.

Also disclosed herein, in some embodiments, are methods of constructing living, three-dimensional liver tissue constructs comprising the steps of: preparing one or more cohered multicellular aggregates comprising mammalian cells; placing said one or more cohered multicellular aggregates onto a support to form at least one of: at least one layer comprising a plurality of cell types, the cell types spatially arranged relative to each other to create a planar geometry; and/or a plurality of layers, at least one layer compositionally or architecturally distinct from at least one other layer to create a laminar geometry; and incubating said one or more multicellular aggregates to allow them to cohere and to form a living, three-dimensional liver tissue construct.

Preparing Cohered Multicellular Aggregates

In some embodiments, the methods involve preparing cohered multicellular aggregates comprising one or more types of mammalian cells, wherein at least one cellular component represents liver cells. In some embodiments, the methods involve preparing cohered multicellular aggregates comprising liver parenchymal cells. In some embodiments, the methods involve preparing cohered multicellular aggregates further comprising non-parenchymal cells. In some embodiments, the methods involve preparing cohered multicellular aggregates further comprising one or more other cell types, selected from the group: endothelial cells, stellate cells, fibroblasts, Kupffer cells, immune cells, lymphocytes, cancer cells, virus-bearing cells, pathogenic cells, adipocytes, adipogenic cells, smooth muscle cells, or stem/progenitor-derived cells.

There are various ways to make multicellular aggregates having the characteristics described herein. In some embodiments, a multicellular aggregate is fabricated from a cell paste containing a plurality of living cells or with a desired cell density and viscosity. In further embodiments, the cell paste is shaped into a desired shape and a multicellular body formed through maturation (e.g., incubation). In some embodiments, the shape of the multicellular body is determined by the shape of a surrounding mold or frame. In further embodiments, the mold or frame is fabricated by an automated instrument in a defined geometry. In still further embodiments, the mold or frame consists of bio-ink and contains liver-derived cells. In further embodiments, the mold or frame comprises liver-derived non-parenchymal cells and the paste utilized to fill the frame and create the multicellular aggregate comprises parenchymal cells. In some embodiments, the multicellular aggregates are substantially cylindrical. In other embodiments, the multicellular aggregates are hexagonal, square, cuboidal, rectangular, and polyhedral. In still further embodiments, multiple multicellular aggregates are formed by fabricating the surrounding mold or frame in a tessellated pattern of repeating geometry and subsequently or simultaneously filling the molds or frames with cell paste. In further embodiments, the cell paste is incubated in a controlled environment to allow the cells to adhere and/or cohere to one another to form the elongate multicellular body. In another particular embodiment, a multicellular body is produced by shaping a cell paste including a plurality of living cells in a device that holds the cell paste in a three-dimensional shape. In further embodiments, the cell paste is incubated in a controlled environment while it is held in the three dimensional shape for a sufficient time to produce a body that has sufficient cohesion to support itself on a flat surface.

In various embodiments, a cell paste is provided by: 1) collecting cells or cell aggregates (of one or more cell types) and a biocompatible gel or liquid, such as cell culture medium (e.g., in a pre-determined ratio) to result in a cell suspension, and 2) compacting the cellular suspension to produce a cell paste with a desired cell density and viscosity. In various embodiments, compacting is achieved by a number of methods, such as by concentrating a particular cell suspension that resulted from cell culture to achieve the desired cell concentration (density), viscosity, and consistency required for the cell paste. In a particular embodiment, a relatively dilute cell suspension from cell culture is centrifuged for a determined time to achieve a cell concentration in the pellet that allows shaping in a mold. Tangential flow filtration ("TFF") is another suitable method of concentrating or compacting the cells. In some embodiments, compounds are combined with the cell suspension to lend the extrusion properties required. Suitable compounds include, by way of non-limiting examples, surfactant polyols, collagens, hydrogels, peptide hydrogels, amino acid-based gels, Matrigel™, nanofibers, self-assembling nanofibers, gelatin, fibrinogen, etc.

In some embodiments, the cell paste is produced by mixing a plurality of living cells with a tissue culture medium, and compacting the living cells (e.g., by centrifugation). One or more ECM components (or derivative of an ECM component) is optionally included by, resuspending the cell pellet in one or more physiologically acceptable buffers containing the ECM component(s) (or derivative(s) of ECM component(s)) and the resulting cell suspension centrifuged again to form a cell paste.

In some embodiments, the cell density of the cell paste desired for further processing varies with cell types. In further embodiments, interactions between cells determine the properties of the cell paste, and different cell types will have a different relationship between cell density and cell-cell interaction. In still further embodiments, the cells are pre-treated to increase cellular interactions before shaping the cell paste. For example, in some cases, cells are incubated inside a centrifuge tube after centrifugation in order to enhance cell-cell interactions prior to shaping the cell paste. In some embodiments, the cell paste is shaped concomitantly with bioprinting; wherein the cohesion of individual cells to each other to form bio-ink occurs during or after bioprinting.

In various embodiments, many methods are used to shape the cell paste. For example, in a particular embodiment, the cell paste is manually molded or pressed (e.g., after concentration/compaction) to achieve a desired shape. By way of a further example, the cell paste is taken up (e.g., aspirated) into an instrument, such as a micropipette or syringe (e.g., a capillary pipette or a glass/plastic syringe), that shapes the cell paste to conform to an interior surface of the instrument. The cross-sectional shape of the micropipette (e.g., capillary pipette) is alternatively circular, square, rectangular, triangular, or other non-circular cross-sectional shape. In some embodiments, the cell paste is shaped by depositing it into a preformed mold, such as a plastic mold, metal mold, or a gel mold. In some embodiments, centrifugal casting or continuous casting is used to shape the cell paste. In some embodiments, the shaping of the bio-ink occurs concomitantly or after bioprinting. In further embodiments, the shaping of the bio-ink occurs as the result of a co-printed mold; wherein the mold is optionally deposited via bioprinting; wherein the mold comprises one or more of: bio-ink, bio-ink that further comprises an extrusion compound, gel, hydrogel, synthetic polymer, carbohydrate, protein, or mammalian cells, or combinations thereof. In still further embodiments, one or more components of the co-printed mold are removed after bioprinting; wherein the removal method is selected from one of: physical means, solubilization with aqueous media; chemical treatment; enzymatic treatment; modulating temperature. In further embodiments, the co-printed mold remains associated with the tissue after fabrication. In still further embodiments, only the cellular component(s) of the co-printed mold remain associated with the tissue after fabrication.

In some embodiments, multicellular aggregates of a defined shape are also suitable to build the engineered liver tissues described herein. Spherical multicellular aggregates are optionally generated by a variety of methods, including, but not limited to, cellular self-assembly, the use of molds, and hanging drop methods. In further embodiments, a method to produce substantially spherical multicellular aggregates comprises the steps of 1) providing a cell paste containing a plurality of pre-selected cells or cell aggregates with a desired cell density and viscosity, 2) manipulating the cell paste into a cylindrical shape, 3) cutting cylinders into equal fragments, 4) optionally letting the fragments round up overnight on a gyratory shaker, and 5) optionally allowing the substantially spherical multicellular aggregates to mature over a period of 1 hour to 7 days. In further embodiments, multicellular aggregates are generated via acoustic focusing methodologies.

In some embodiments, a partially adhered and/or cohered cell paste is used for bioprinting; wherein cohesion and bio-ink formation occurs primarily post-printing. In other embodiments, the cellular paste is shaped in a first step prior to bioprinting. In further embodiments, the cell paste is transferred from the first shaping device (e.g., capillary pipette) to a second shaping device (e.g., a mold) that allows nutrients and/or oxygen to be supplied to the cells while they are retained in the second shaping device for an additional maturation period. One example of a suitable shaping device that allows the cells to be supplied with nutrients and oxygen is a mold for producing a plurality of multicellular aggregates (e.g., substantially identical multicellular aggregates). By way of further example, such a mold includes a biocompatible substrate made of a material that is resistant to migration and ingrowth of cells into the substrate and resistant to adherence of cells to the substrate. In various embodiments, the substrate is suitably be made of Teflon® (PTFE), stainless steel, NovoGel™, agarose, polyethylene glycol, glass, metal, plastic, or gel materials (e.g., agarose or other hydrogels), and similar materials. In some embodiments, the mold is also suitably configured to allow supplying tissue culture media to the cell paste (e.g., by dispensing tissue culture media onto the top of the mold).

Thus, in embodiments where a second shaping device is used, the partially adhered and/or cohered cell paste is transferred from the first shaping device (e.g., a capillary pipette) to the second shaping device (e.g., a mold). In further embodiments, the partially adhered and/or cohered cell paste is transferred by the first shaping device (e.g., the capillary pipette) into the grooves of a mold. In still further embodiments, following a maturation period in which the mold is incubated along with the cell paste retained therein in a controlled environment to allow the cells in the cell paste to further adhere and/or cohere to one another to form the multicellular aggregate, the cohesion of the cells will be sufficiently strong to allow the resulting multicellular aggregate to be picked up with an implement (e.g., a capillary pipette). In still further embodiments, the capillary pipette is suitably be part of a printing head of a bioprinter or similar apparatus operable to automatically place the multicellular aggregate into a three-dimensional construct.

In some embodiments, the cross-sectional shape and size of the multicellular aggregates will substantially correspond to the cross-sectional shapes and sizes of the first shaping device and optionally the second shaping device used to make the multicellular aggregates, and the skilled artisan will be able to select suitable shaping devices having suitable cross-sectional shapes, cross-sectional areas, diameters, and lengths suitable for creating multicellular aggregates having the cross-sectional shapes, cross-sectional areas, diameters, and lengths discussed above.

Placing Cohered Multicellular Aggregates onto a Support

A number of methods are suitable to place multicellular aggregates on a support to produce a desired three-dimensional structure. For example, in some embodiments, the multicellular aggregates are manually placed in contact with one another, deposited in place by extrusion from a pipette, nozzle, or needle, or positioned by an automated, computer-assisted device such as a bioprinter.

As described herein, in various embodiments, multicellular aggregates have many suitable shapes and sizes. In some embodiments, multicellular aggregates are elongate with any of several suitable cross-sectional shapes including, by way of non-limiting example, circular, oval, square, triangular, polygonal, and irregular. In further embodiments, multicellular aggregates are elongate and in the form of a cylinder. In some embodiments, elongate multicellular aggregates are of similar lengths and/or diameters. In other embodiments, elongate multicellular aggregates are of differing lengths and/or diameters. In some embodiments, multicellular aggregates are substantially spherical. In some embodiments, the engineered liver tissues include substantially spherical multicellular aggregates that are substantially similar in size. In other embodiments, the engineered liver tissues include substantially spherical multicellular aggregates that are of differing sizes. In some embodiments, engineered liver tissues of different shapes and sizes are formed by arranging multicellular aggregates of various shapes and sizes.

In some embodiments, the cohered multicellular aggregates are placed onto a support. In various embodiments, the support is any suitable biocompatible surface. In still further embodiments, suitable biocompatible surfaces include, by way of non-limiting examples, polymeric material, porous membranes, plastic, glass, metal, hydrogel, and combinations thereof. In some embodiments, the support is coated with a biocompatible substance including, by way of non-limiting examples, a hydrogel, a protein, a chemical, a peptide, antibodies, growth factors, or combinations thereof. In one embodiment, the support is coated with NovoGel™. In another embodiment, the support is coated with agarose. In one embodiment, the cohered multicellular aggregates are placed into the wells of a biocompatible multi-well container.

Once placement of the cohered multicellular aggregates is complete, in some embodiments, a tissue culture medium is poured over the top of the construct. In further embodiments, the tissue culture medium enters the spaces between the multicellular bodies to support the cells in the multicellular bodies.

Applying a Layer of a First Type of Cells and/or a Layer of a Second Type of Cells A number of methods are suitable to apply one or more layers of cells on one or more external surfaces of the cohered mammalian cell construct. For example, in some embodiments, applying a layer of cells comprises coating one or more surfaces of said cohered multicellular aggregates with a suspension, sheet, monolayer, or fused aggregates of cells. In various embodiments, 1, 2, 3, 4, or more surfaces of the cohered mammalian cell construct are coated.

In some embodiments, applying a layer of cells comprises bioprinting an additional layer of fused multicellular aggregates. In other embodiments, applying a layer of cells comprises bioprinting, spraying, or ink jetting a solution, suspension, or liquid concentrate of cells. In further embodiments, a suitable cell suspension comprises about $1 \times 10^4$ about $1 \times 10^6$ cells/µl. In still further embodiments, a suitable cell suspension comprises about $1 \times 10^5$ about $1.5 \times 10^5$ cells/µl. In further embodiments, applying a layer of cells comprises dispensing a suspension of cells directly onto one or more surfaces of the cohered mammalian cell construct as spatially-distributed droplets. In still further embodiments, applying a layer of cells comprises dispensing a suspension of cells directly onto one or more surfaces of the cohered mammalian cell construct as a spray. Layers of cells are, in various embodiments, applied at any suitable time in the construction process. In some embodiments, one or more layers of cells are applied on one or more external surfaces of the cohered mammalian cell construct immediately after bioprinting (e.g., up to 10 min.). In other embodiments, one or more layers are applied after bioprinting (e.g., after 10 min.). In yet other embodiments, one or more layers are applied during maturation of the construct.

In some embodiments, the methods further comprise the step of culturing a layer of cells on a support. In such embodiments, applying a layer of cells, in some cases, comprises placing one or more surfaces of the engineered liver tissue construct in direct contact with an established culture of cells. In further embodiments, the construct is bioprinted directly onto a cultured layer of cells or a monolayer of cells. Any type of cultured cell layer on a biocompatible support is suitable. In some embodiments, multicellular aggregates are bioprinted onto a layer of endothelial cells. In other embodiments, multicellular aggregates are bioprinted onto a layer of non-parenchymal cells. In further embodiments, the layer of cells adheres and/or coheres with the multicellular aggregates of the bioprinted construct. In some embodiments, each layer of a multi-layered structure are bioprinted. In further embodiments, the individual layers comprise variable forms of bio-ink, including but not limited to: cohered cell aggregates, cell paste, cell paste in combination with extrusion compound(s) or other additives, cell monolayers, and cell sheets.

Co-Printed Molds Used to Fabricate Compartmentalized Tissues

In some embodiments, the methods comprise preparing one or more bio-inks comprising non-parenchymal cells; preparing one or more bio-inks comprising parenchymal cells, such as hepatocytes or hepatocyte-like cells; depositing the bio-inks onto a support; and incubating the deposited bio-inks for a duration of about 1 hour to about 30 days to form a living, three-dimensional liver tissue construct comprising at least one compartment, the compartment comprising an interior comprising parenchymal cells confined by a border comprising non-parenchymal cells.

In some embodiments, the methods comprise preparing one or more cohered multicellular aggregates comprising mammalian liver cells; placing the one or more cohered multicellular aggregates onto a support to form at least one of: at least one layer comprising a plurality of cell types, the cell types spatially arranged relative to each other to create a planar geometry; and a plurality of layers, at least one layer compositionally or architecturally distinct from at least one other layer to create a laminar geometry; and incubating said one or more multicellular aggregates for a duration of about 1 hour to about 30 days to allow them to cohere and to form a living, three-dimensional liver tissue construct.

Figure 2:
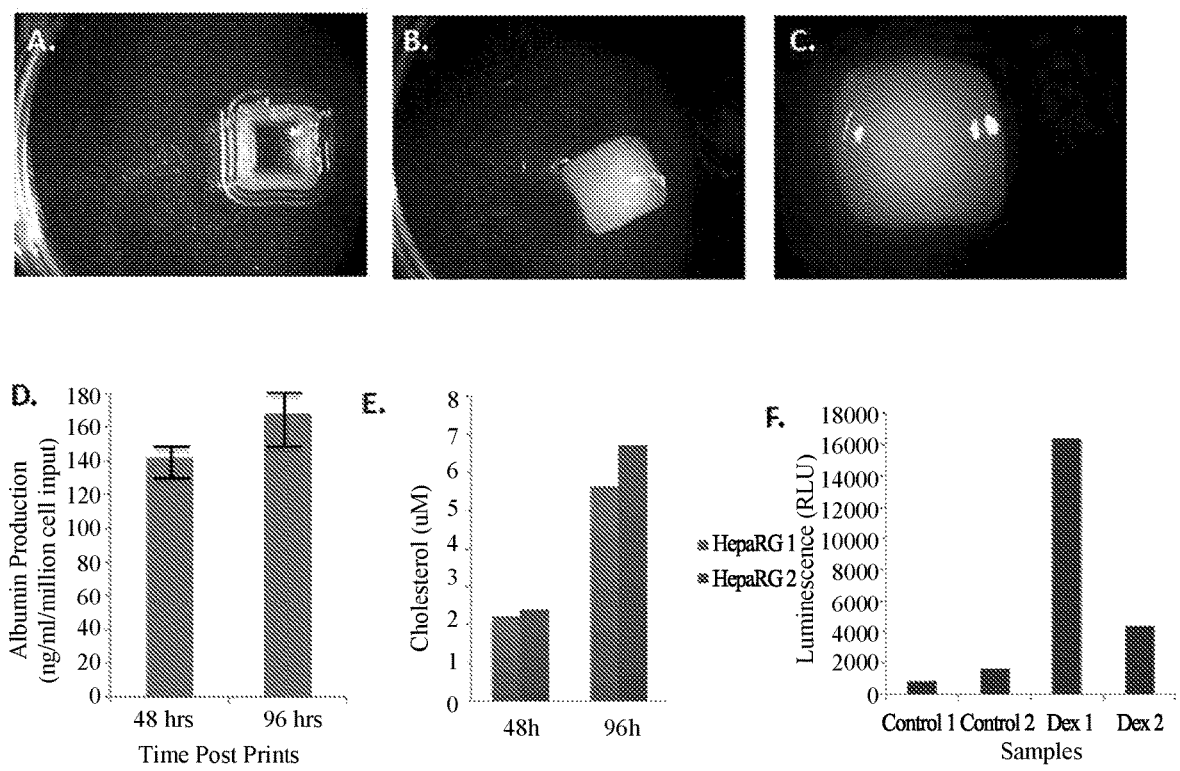
FIG. 2 is a non-limiting, exemplary demonstration of maturation and biochemical characterization of bio-printed liver constructs containing HepaRG cells. HepaRG cells were deposited into the center of the perimeter box, followed by maturation for 96 hours (A-C). Bio-printed liver constructs are metabolically active producing albumin (D) and cholesterol (E) at 96 hours. Following dexamethasone treatment, cytochrome P450 (CYP3A4) activity is more than 5-fold higher than non-treated controls (F).

Referring to FIG. 2, in a particular embodiment, liver constructs containing HepaRG cells were bio-printed, matured, and biochemically characterized. First, a perimeter box with dimensions of 4 mm×4 mm×1 mm was printed with bio-ink containing endothelial cells and hepatic stellates. Second, HepRG cells were deposited into the center of the perimeter box. This was followed by maturation for 96 hours at 37° C. Third, fusion of the bio-printed construct was observed at 20 hours post print. In this embodiment, the bio-printed liver constructs were metabolically active producing albumin and cholesterol at 96 hours.

Figure 3:
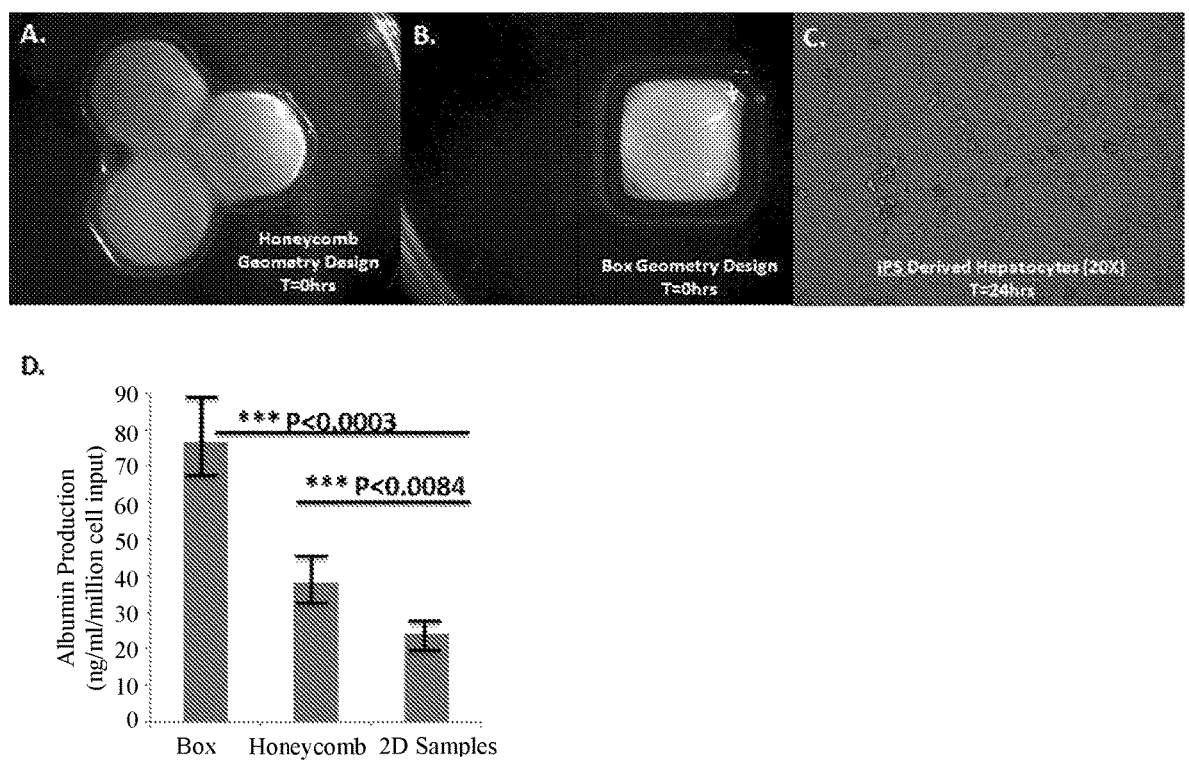
FIG. 3 is a non-limiting, example of bio-printed structures in defined geometric patterns (A, B) containing iPSC-derived hepatocytes (C) that synthesize significantly higher albumin levels (D), per million input cells, in the engineered, bioprinted construct than 2D culture controls.

Referring to FIG. 3, in a particular embodiment, liver constructs are bioprinted with borders of non-parenchymal cells and fills of parenchymal cells each made with an extrusion compound.

Figure 4:
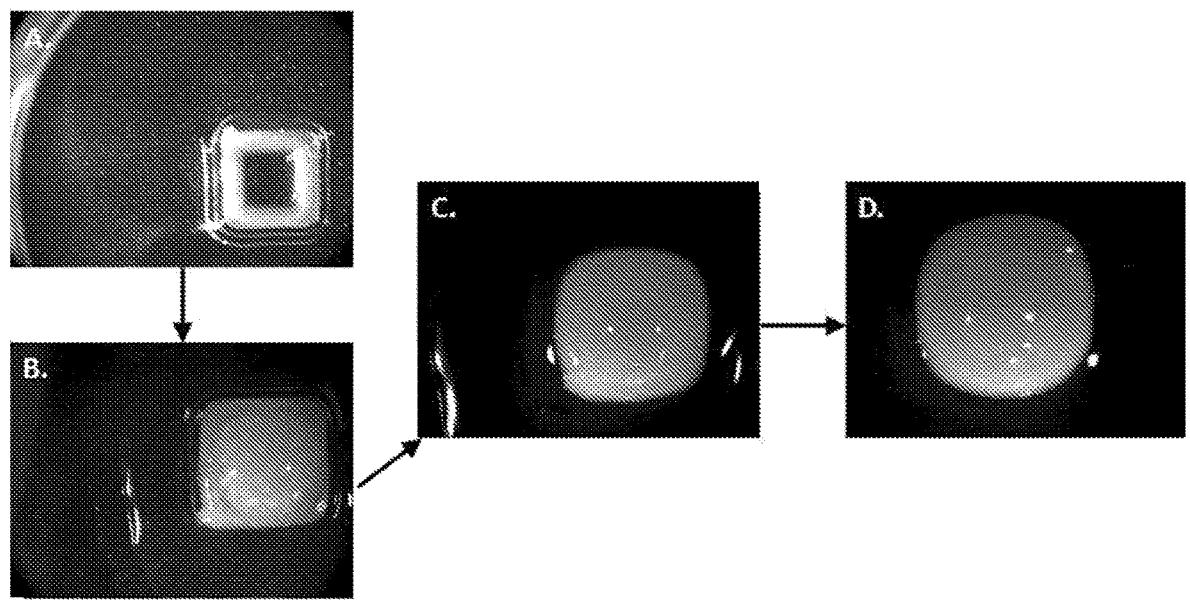
FIG. 4 is a non-limiting, exemplary demonstration of maturation of a bio-printed liver construct (A) containing discrete spheroids of non-parenchymal cells (B). The bio-printed construct remained fused and stable upon incubation for an additional 24 hours (C, D).

Referring to FIG. 4, in a particular embodiment, liver constructs are bioprinted with a border including endothelial cells and hepatic stellates, a fill including primary hepatocytes, and a third compositional component introduced as spatially-dispersed spheroids including endothelial cells and hepatic stellates within the fill.

Figure 5:
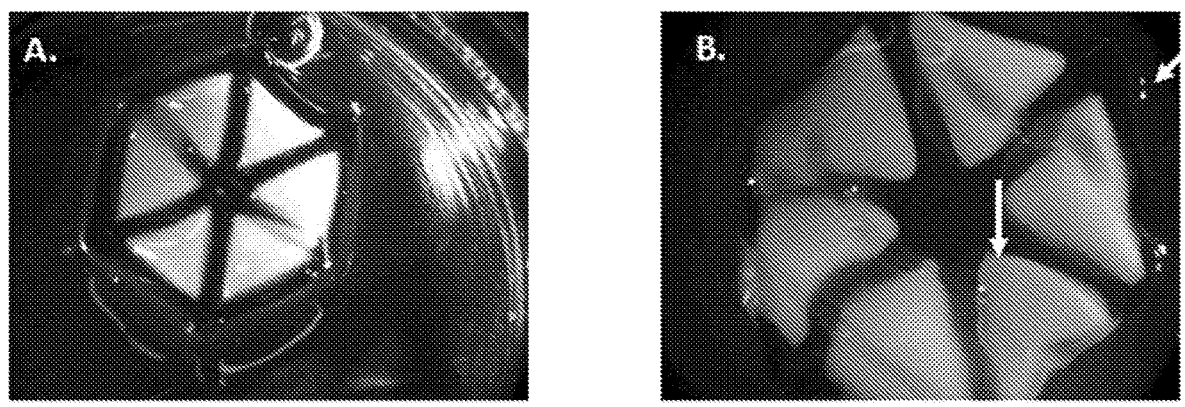
FIG. 5 is a non-limiting, exemplary demonstration of dissolution of the co-printed mold which allows spatial and temporal control over the printing process of the hepatic cells and results in the generation of user-specified compartments of a defined shape and size in the x, y, and z axes. Hepatic tissue is shown after printing (A), arrows indicate regions where the co-printed mold has dissolved 24 hours post print and areas where additional cellular inputs can be added (B).
Figure 6:
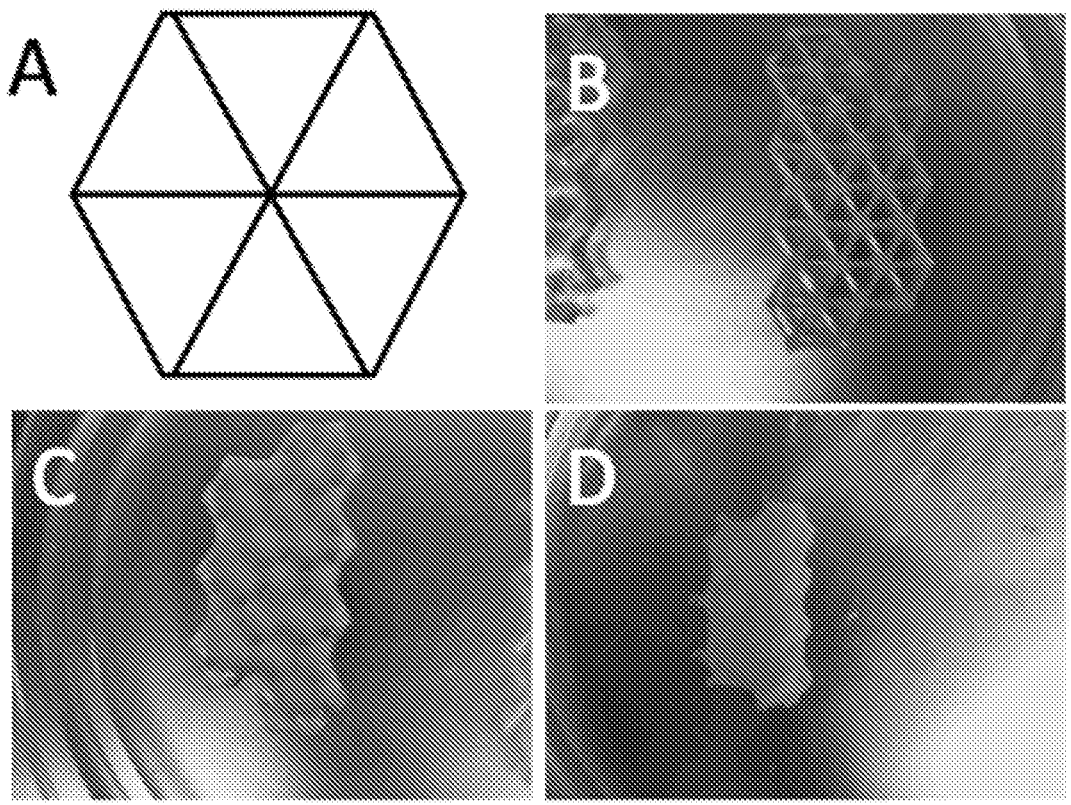
FIG. 6 is a macroscopic image depicting a non-limiting example of an engineered liver tissue, in this case, a multi-layered liver tissue bioprinted using a continuous deposition mechanism using bio-ink composed of multiple liver cell types and a water-soluble extrusion compound (e.g., PF-127). (A) shows a schematic diagram of a single functional unit highlighting the planar geometry created by patterning bio-ink and negative space; (B) tessellated, functional units bioprinted with PF-127 containing $2\times10^8$ cells; (C) shows the construct 20 minutes after application of media; and (D) shows the construct 16 hours after application of media to the structure and dissolution of the extrusion compound. Note retention of the planar geometry over time.

Referring to FIG. 5, in a particular embodiment, liver constructs are bioprinted with a co-mold fabricated from a material that does not contain cells (A), and dissolves in an aqueous media (e.g., PF-127) leaving only fills and establishing a negative space (B).

Referring to FIG. 6, in a particular embodiment, liver constructs are bioprinted using a continuous deposition technique using bio-ink composed of multiple liver cell types encapsulated in a water-soluble extrusion compound (e.g., PF-127) to form a tessellated functional unit pattern.

Figure 8:
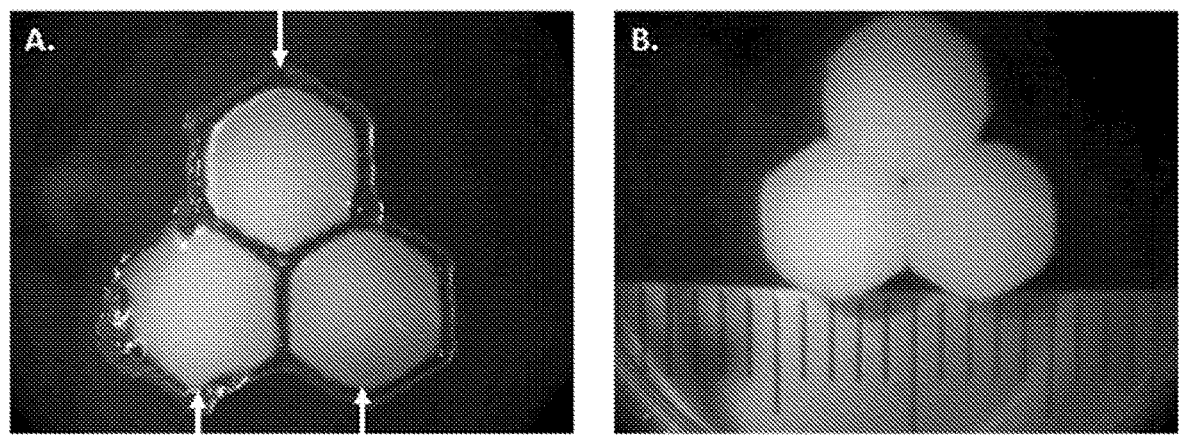
FIG. 8 is a non-limiting example of dissolution of a co-printed mold allowing fusion of distinct compartmentalized hepatic cellular regions (A; marked by arrows). Over time (B; T=24 hours) the regions fuse into a solid bio-printed tissue.

Referring to FIG. 8, in a particular embodiment, compartmentalized liver constructs are bioprinted with a co-printed mold that does not contain cells used to shape multicellular aggregates into hexagons (A). In this embodiment, the non-cellular material disappears to yield a scaffold-free tissue at the time of use (B).

Figure 10:
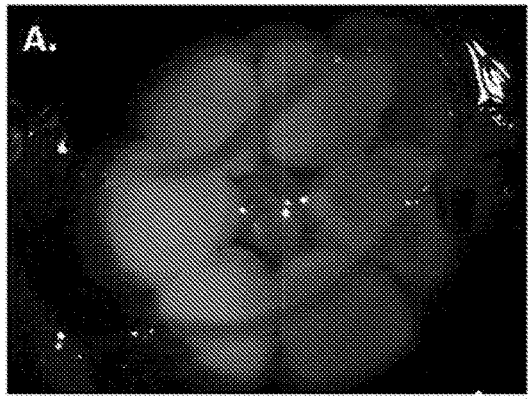
FIG. 10 is a non-limiting example of a co-printed mold (A; 4% Gelatin and 2% Alginate) bioprinted by continuous deposition with a syringe deposition module (SDM) to produce a fused 3D liver tissue construct. Addition of endothelial bio-ink in the center of the structure increases the complexity of the construct (B). E-Cadherin (C) and CD31 (D) staining demonstrate epithelial and endothelial cells present throughout the areas in which they were bioprinted at 144 hours post-print. TUNEL staining demonstrates limited cell death within the core of the engineered liver tissue following 144 h incubation (E).
Figure 10:
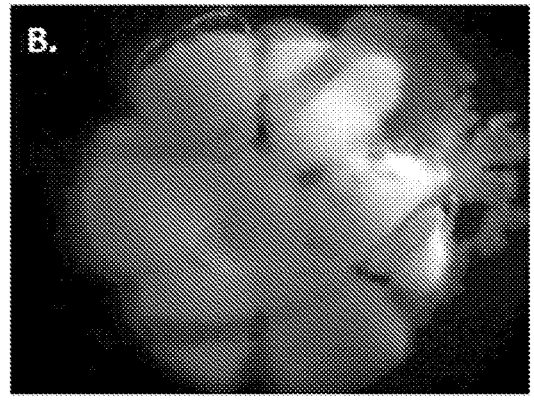
Figure 10:
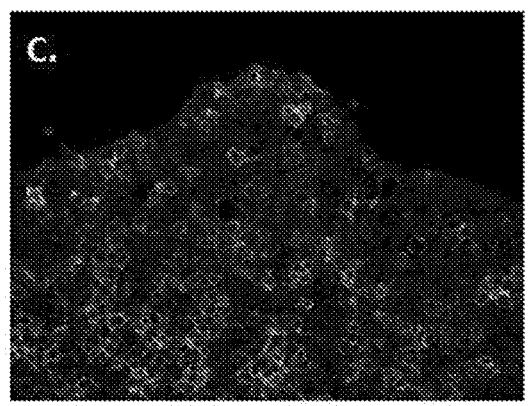
Figure 10:
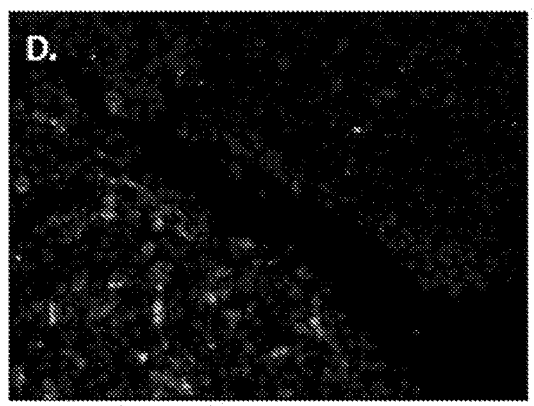
Figure 10:

Referring to FIG. 10, in a particular embodiment, compartmentalized liver constructs are bioprinted with a co-mold used as a border which is filled with HepG2 cells.

Figure 11:
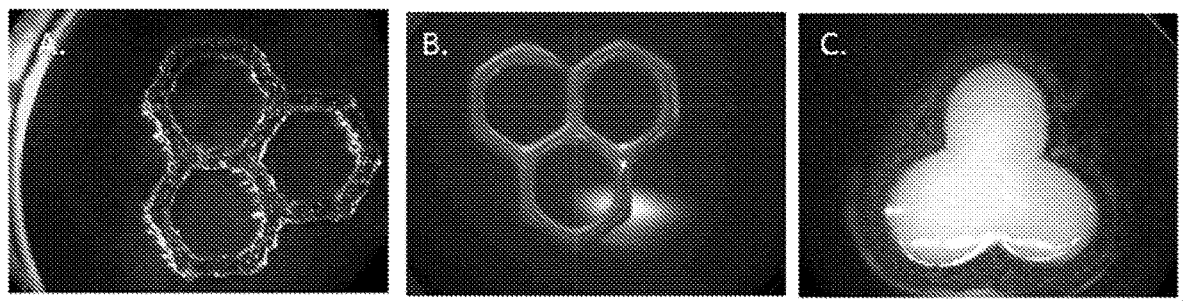
FIG. 11 is a non-limiting example of a co-printed mold (co-mold) comprised of hydrogel (4% gelatin: 2% alginate) (A) or bio-ink comprised of non-parenchymal cells and a hydrogel-based extrusion compound (B). The bio-ink co-mold lines contained $150\times10^6$ cells per mL of hydrogel extrusion compound. Addition of HepG2 cells to the co-mold structure and incubation for 24 h, results in a fused, bioprinted liver structure (C). Dissolution of the extrusion compound occurs over time in aqueous media.

Referring to FIG. 11, in a particular embodiment, a co-printed mold containing cells is bio-printed as a border into which parenchymal cells are used as a fill, in this case, HepG2 cells.

Figure 12:
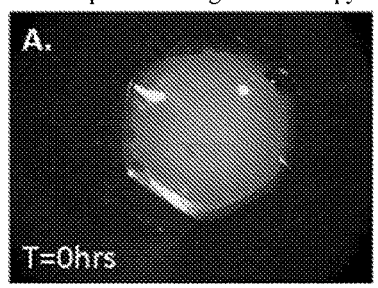
FIG. 12 is a non-limiting example of a dense, cellular liver tissue, fabricated by continuous deposition using two syringe deposition modules (SDM) on the NovoGen MMX Bioprinter. The co-mold lines containing 4% gelatin and 2% alginate were deposited by the first SDM module followed by filling of HepG2 bio-paste with a second SDM. Tissue is shown at t=0 (A), and t=48 hours (B) after printing. Also shown is H&E staining of tissue 48 hours after printing at 20× magnification (C).
Figure 12:
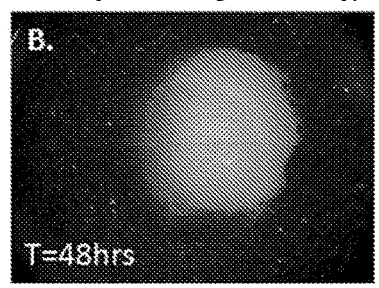
Figure 12:
Figure 13:
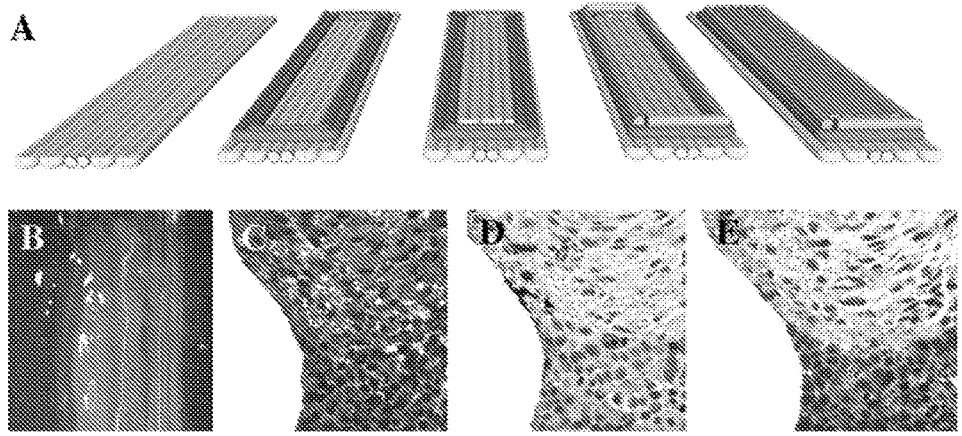
FIG. 13 is a non-limiting example of a bioprinted neotissue with laminar geometry. A NovoGel™ hydrogel base and co-printed confining box were bioprinted, followed by deposition of a first layer comprising liver epithelial cell bio-ink (HepG2 cells), onto which a second layer was bioprinted comprised of hepatic stellate cells and endothelial cells. In this example, the stellate: EC layer was bioprinted via continuous deposition of bio-ink containing a hydrogel extrusion compound (A). Gross images of construct immediately after fabrication demonstrating the two distinct layers of bio-ink (B). Hematoxylin and Eosin staining of sections of formalin-fixed paraffin-embedded constructs (C) following 48 hours of culture reveals distinct morphology of the two layers and establishment of a laminar geometry. CD31-positive cells are restricted to the upper layer of the construct where a suspension of endothelial cells and hepatic stellate cells were bioprinted (D), while IGF-2-positive HepG2 are found only in the bottom layer (E).
Figure 14:
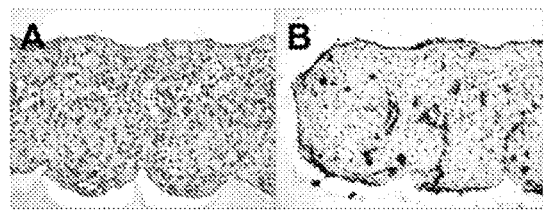
FIG. 14 is a non-limiting example of cell patterning and layering in bioprinted liver tissues. Hematoxylin and Eosin staining of paraffin-embedded tissue sections reveals a contiguous neotissue (A) formed by bioprinting polytypic cell populations containing vascular endothelial cells and hepatic stellate cells. Staining of the tissue sections with antibody directed at CD31 reveals the presence of centrally-located EC-lined microvessels and an external layer of CD31-positive EC (B).

Referring to FIG. 12, in a particular embodiment, compartmentalized liver constructs are bioprinted using a non-parenchymal border and a parenchymal fill (A) to achieve a high, tissue-like density (C).

Incubating Multicellular Aggregates

In some embodiments, the multicellular aggregates are incubated. In further embodiments, the incubation allows the multicellular aggregates adhere and/or cohere to form a tissue, such as a liver tissue. In some embodiments, the multicellular aggregates cohere to form a tissue in a cell culture environment (e.g., a Petri dish, cell culture flask, bioreactor, etc.). In further embodiments, the multicellular aggregates cohere to form a tissue in an environment with conditions suitable to facilitate growth of the cell types included in the multicellular aggregates. In one embodiment, the multicellular aggregates are incubated at about 37° C., in a humidified atmosphere containing about 5% CO2, in the presence of cell culture medium containing factors and/or ions to foster adherence and/or coherence. In other embodiments, the multicellular aggregates are maintained in an environment that contains 0.1% to 21% O2.

The incubation, in various embodiments, has any suitable duration. In further various embodiments, the incubation has a duration of about 20, 30, 40, 50, 60, 70, 80, 90, 100, 110, 120, 130, 140, 150, 160, 170, 180, or more minutes, including increments therein. In further various embodiments, the incubation has a duration of about 1, 2, 3, 4, 5, 6, 7, 8, 9, 10, 11, 12, 13, 14, 15, 16, 17, 18, 19, 20, 21, 22, 23, 24, 36, 48, or more hours, including increments therein. In further various embodiments, the incubation has a duration of about 1, 2, 3, 4, 5, 6, 7, 8, 9, 10, 11, 12, 13, 14, 15, 16, 17, 18, 19, 20, or more days, including increments therein. Several factors influence the time required for multicellular aggregates to cohere to form a tissue including, by way of non-limiting examples, cell types, cell type ratios, culture conditions, and the presence of additives such as growth factors.

Additional Steps for Increasing Viability of the Engineered Tissue

In some embodiments, the method further comprises steps for increasing the viability of the engineered tissue. In further embodiments, these steps involve providing direct contact between the tissue and a nutrient medium through a temporary or semi-permanent lattice of confinement material. In some embodiments, the tissue is constrained in a porous or gapped material. Direct access of at least some of the cells of the engineered tissue to nutrients increases the viability of the engineered tissue.

In further embodiments, the additional and optional steps for increasing the viability of the engineered tissue include: 1) optionally dispensing base layer of confinement material prior to placing cohered multicellular aggregates; 2) optionally dispensing a perimeter of confinement material; 3) bioprinting cells of the tissue within a defined geometry; and 4) dispensing elongate bodies (e.g., cylinders, ribbons, etc.) of confinement material overlaying the nascent tissue in a pattern that introduces gaps in the confinement material, such as a lattice, mesh, or grid.

Many confinement materials are suitable for use in the methods described herein. In some embodiments, hydrogels are exemplary confinement materials possessing one or more advantageous properties including: non-adherent, biocompatible, extrudable, bioprintable, non-cellular, of suitable strength, and not soluble in aqueous conditions. In some embodiments, suitable hydrogels are natural polymers. In one embodiment, the confinement material is comprised of NovoGel™. In further embodiments, suitable hydrogels include those derived from surfactant polyols such as Pluronic F-127, collagen, hyaluronate, fibrin, alginate, agarose, chitosan, gelatin, and derivatives or combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, and combinations thereof.

In some embodiments, the gaps overlaying pattern are distributed uniformly or substantially uniformly around the surface of the tissue. In other embodiments, the gaps are distributed non-uniformly, whereby the cells of the tissue are exposed to nutrients non-uniformly. In non-uniform embodiments, the differential access to nutrients is optionally exploited to influence one or more properties of the tissue. For instance, in some cases, it is desirable to have cells on one surface of a bioprinted tissue proliferate faster than cells on another surface of the bioprinted tissue. In some embodiments, the exposure of various parts of the tissue to nutrients is changed at various times to influence the development of the tissue toward a desired endpoint.

In some embodiments, the confinement material is removed at any suitable time, including but not limited to, immediately after bioprinting (e.g., within 10 minutes), after bioprinting (e.g., after 10 minutes), before the cells are substantially cohered to each other, after the cells are substantially cohered to each other, before the cells produce an extracellular matrix, after the cells produce an extracellular matrix, just prior to use, and the like. In various embodiments, confinement material is removed by any suitable method. For example, in some embodiments, the confinement material is excised, pulled off the cells, digested, or dissolved.

In some embodiments, the methods further comprise the step of subjecting the engineered liver tissue to shear force, caused by fluid flow, agitation, or convective recirculation, on one or more sides.

Three-Dimensional (3D), Engineered, Bioprinted Liver Disorder Models

Provided are models of a liver disorder, comprising a three-dimensional, engineered, bioprinted, biological liver tissue construct. In some embodiments, the model comprises a three-dimensional, engineered, bioprinted, biological liver tissue construct comprising parenchymal cells and non-parenchymal cells, the parenchymal cells comprising hepatocytes or hepatocyte-like cells, wherein at least one component of the liver tissue construct is bioprinted, and wherein the liver tissue construct exhibits at least one phenotype characteristic of a liver disorder.

In some embodiments, the liver tissue construct comprises at least one compartment comprising an interior defined by a border, the interior comprising the parenchymal cells, and the border comprising non-parenchymal cells. In some embodiments, the compartment of the liver tissue construct is defined by a planar geometry. In some embodiments, the liver tissue construct is at least three cells thick in its smallest dimension. In some embodiments, the liver tissue construct is at least three cells thick in its smallest dimension, and the compartment of the liver tissue construct is defined by a planar geometry. In some embodiments, the liver tissue construct comprises a laminar geometry, wherein a first layer comprises the non-parenchymal cells and a second layer comprises parenchymal cells. In some embodiments, the liver tissue construct comprises a laminar geometry, wherein a first layer comprises the non-parenchymal cells and a second layer comprises parenchymal cells. In some embodiments, the liver tissue construct further comprises a third layer of non-parenchymal cells, wherein the first layer is below the second layer, and the second layer is below the third layer. However, different tissue geometries of the three-dimensional, engineered, bioprinted liver tissue construct, as set forth throughout this application (see i.e. FIGS. 1-19), can be utilized for disease modeling.

The time needed to induce lipid accumulation can be reduced by co-culturing the liver tissue construct with adipocytes or adipocyte-like cells. In some embodiments of the liver disorder model, the liver tissue construct further comprises adipocytes or adipocyte-like cells. In some embodiments, the liver tissue construct comprises at least one compartment comprising an interior defined by a border, the interior comprising the parenchymal cells, and the border comprising non-parenchymal cells. In some embodiments, the liver tissue construct further comprises a second border surrounding the border that defines the interior, the second border comprising adipocytes or adipocyte-like cells. In some embodiments, the liver tissue construct comprises a laminar geometry, wherein a first layer comprises the non-parenchymal cells, a second layer comprises parenchymal cells, a third layer comprises the non-parenchymal cells, and the non-parenchymal cells further comprise adipocytes or adipocyte-like cells. However, different tissue geometries of the three-dimensional, engineered, bioprinted liver tissue construct, as set forth throughout this application (see i.e. FIGS. 1-19), can be utilized for disease modeling.

In some embodiments, the time period for inducing steatosis post bio-printing of the liver tissue construct is 3, 7, 14, 21, 28 days or any number of days less than 28 days. As noted, the three-dimensional, engineered, bioprinted, biological liver tissue construct represents a significant advance over 2-dimensional cell cultures because of its improved longevity and multi-cellular complexity. With its improved longevity and multi-cellular complexity, the liver tissue construct is able to remain viable and functional longer than 2d cell culture in order to cover the time periods of (i) the initial post-bioprinting time period needed to induce the disorder in the liver tissue construct, and (ii) the post-induction time period to evaluate the drug efficacy of a candidate therapeutic agent on the liver disorder.

In some embodiments of the liver disorder model, the at least one phenotype is selected from: a lipid accumulation, an inflammation, an oxidative stress, a fibrosis, a hepatocellular ballooning, a microvesicular steatosis, a macrovesicular steatosis, or any combination thereof. In some embodiments, the at least one phenotype is at least two phenotypes. In some embodiments, the at least one phenotype is two phenotypes. In some embodiments, the microvesicular steatosis, the macrovesicular steatosis, or a combination thereof is present in the hepatocytes. In some embodiments, the fibrosis is co-localized with activated smooth muscle actin (SMA$^+$) cells. In some embodiments, deposited collagen forms networks between hepatocytes thereby disrupting cell:cell contact. In some embodiments, the fibrosis is co-localized with activated stellate cells. Activated stellated cells are detectable by, for example, (SMA+), myofibroblast phenotype, and/or collagen production.

In some embodiments, the liver disorder is selected from the group consisting of: a non-alcoholic fatty liver disease (NAFLD), a non-alcoholic steatohepatitis (NASH), hepatitis A, hepatitis B, hepatitis C, alpha-1-antitrypsin deficiency, cirrhosis, a cancer, hemochromatosis, alcohol-related liver disease, primary biliary cirrhosis, a drug-related injury, or any combination thereof.

In some embodiments of the liver disorder model, the liver disorder is a non-alcoholic fatty liver disease (NAFLD), and the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof. In some embodiments, the NAFLD is a steatosis, and the liver tissue construct exhibits at least one phenotype that is a lipid accumulation. In some embodiments, the NAFLD is a non-alcoholic steatohepatitis (NASH), and the liver tissue construct exhibits at least two phenotypes selected from: a lipid accumulation, an inflammation, an oxidative stress, a fibrosis, a hepatocellular ballooning, a microvesicular steatosis, a macrovesicular steatosis, or any combination thereof. In some embodiments, the NAFLD is an intermediate state between a steatosis and a NASH, and the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof. In some embodiments, the NAFLD is a NASH, the and the liver tissue construct exhibits at least one phenotype that is a lipid accumulation and at least one phenotype that is an inflammation. In some embodiments, the NAFLD is a NASH, and the liver tissue construct exhibits at least one phenotype that is a steatosis (e.g., a microvesicular and/or a macrovesicular steatosis) and at least one phenotype that is a fibrosis. In some embodiments, the NAFLD is a NASH, and the liver tissue construct exhibits at least one phenotype that is a fibrosis and at least one phenotype that is a hepatocellular ballooning. In some embodiments, the NAFLD is a NASH, and the liver tissue construct exhibits at least one phenotype that is a fibrosis, at least one phenotype that is a hepatocellular ballooning, and at least one phenotype that is a steatosis (e.g., a microvesicular and/or a macrovesicular steatosis).

In some embodiments of the liver disorder model, the at least one phenotype is at least a lipid accumulation, wherein the lipid accumulation is induced after the liver tissue construct is bio-printed. In some embodiments, the lipid accumulation is induced by applying an agent (i.e., an inducing agent) to the liver tissue construct, wherein the agent is selected from at least one of: a fatty acid, a free fatty acid, an unsaturated fatty acid, a saturated fatty acid, a palmitic acid, a linoleic acid, a linolenic acid, a myristic acid, an oleic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a cholesterol, a high glucose, a high insulin, a genipin, a amiodarone, a valproic acid, an ethanol, a fialuridine, a tamoxifen, a triglycerides, an olanzapine, a glucocorticoids, a IL-17A, an aflatoxin B1, a fructose, a HBx protein, or any combination thereof.

In some embodiments, the liver disorder (e.g., a NAFLD) is induced by applying at least two agents (i.e., at least two inducing agents) to the liver tissue construct selected from: a fructose, a glucose, a fatty acid, a lipopolysaccharide (LPS), a IL1β, a TNFα, or any combination thereof.

In some embodiments, a fatty acid inducing agent has a concentration of: at least about 1 µM, at least about 5 µM, at least about 10 µM, at least about 15 µM, at least about 20 µM, at least about 25 µM, at least about 50 µM, at least about 75 µM, at least about 100 µM, at least about 200 µM, at least about 300 µM, at least about 400 µM, at least about 500 µM, at least about 600 µM, at least about 700 µM, at least about 800 µM, at least about 900 µM, at least about 1000 µM, or any concentration in-between. In some embodiments, a fatty acid inducing agent has a concentration of between about 1 µM and about 1000 µM, between about 10 µM and about 1000 µM, between about 25 µM and about 1000 µM, between about 50 µM and about 1000 µM, or between about 100 µM and about 1000 µM. In some embodiments, a fructose inducing agent has a concentration of at least about 1 mM, at least about 5 mM, or at least about 10 mM. In some embodiments, a fructose inducing agent has a concentration of between about 1 mM and about 50 mM. In some embodiments, the liver disorder is induced by applying a inducing agent (e.g., a fatty acid such as palmitic acid) daily or in a continuous, pulsed, or transient fashion over the course of at least 10 days, at least 14 days, or at least 21 days. In some embodiments, an inducing agent (e.g., at least two inducing agents) is applied to the liver tissue construct for at least 1, 2, 3, 4, 5, 6, 7, 8, 9, 10, 11, 12, 13, 14, 15, 16, 17, 18, 19, 20, 21, 22, 23, 24, 25, 26, 27, 28 or any number of consecutive days.

The time needed to induce lipid accumulation can be reduced by applying a fatty acid uptake enhancer to the liver tissue construct. In some embodiments of the liver disorder model, the further aid induction of lipid accumulation, a fatty acid uptake enhancer, such as genipin, was used in combination with a fatty free acid. In some embodiments, the genipin has a concentration of at least 0.1 µM, 0.2 µM, 0.3 µM, 0.4 µM, 0.5 µM, 0.6 µM, 0.7 µM, 0.8 µM, 0.9 µM, 1.0 µM, 2.0 µM, 3.0 µM, 4.0 µM, 5.0 µM, 6.0 µM, 7.0 µM, 8.0 µM, 9.0 µM, 10.0 µM, or any concentration in-between. In some embodiments, the liver tissue construct is contacted with palmitic acid in combination with genipin for at least 1, 2, 3, 4, 5, 6, 7, 8, 9, 10, 11, 12, 13, 14, 15, 16, 17, 18, 19, 20, 21, 22, 23, 24, 25, 26, 27 days or more to induce lipid accumulation. In other embodiments, the genipin has a concentration of at least 1 uM, 2 uM, 3 uM, 4 uM, 5 uM or more.

As noted, the 3D bioprinted liver tissue construct represents a significant advance over 2D cell cultures because of increased longevity and multicellular complexity. With respect to multicellular complexity, the induction time for NASH can be reduced by incorporating Kupffer cells (KCs) into the parenchymal cells in the liver tissue construct. KCs are resident liver macrophage cells that can produce an inflammatory response when activated. Thus, inflammation can be induced by applying an inflammatory agent, such as a lipopolysaccharide (LPS) or a IL-1β, to activate the Kupffer cells to contribute inflammation. Alternatively, KCs can activated by hepatocellular injury. Once activated, KCs secrete inflammatory cytokines.

In some embodiments of the liver disorder model, the NAFLD is a NASH, and the liver tissue construct exhibits at least one phenotype that is a lipid accumulation and at least one phenotype that is an inflammation. In some embodiments, the parenchymal cells further comprise Kupffer cells, and the Kupffer cells contribute to the inflammation. In some embodiments, the Kupffer cells further contribute to hepatic stellate cell activation and/or fibrosis. In some embodiments, the Kupffer cells are activated to contribute to the inflammation after the lipid accumulation is induced in the liver tissue construct. In some embodiments, the Kupffer cells are activated by an inducing agent, and the inducing agent is a lipopolysaccharide (LPS), a IL-1β, any agent that is capable of inducing the Kupffer cells to contribute to the inflammation, or any combination thereof. In some embodiments, the liver disorder model further comprises the phenotype of a fibrosis.

In some embodiments, the non-parenchymal cells further comprise hepatic stellate cells, and the hepatic stellate cells contribute to the fibrosis. In some embodiments, the hepatic stellate cells are activated to contribute to the fibrosis by the Kupffer cells, thereby enabling the induction of the inflammation and the fibrosis to occur simultaneously. In some embodiments, the fibrosis is induced by an inducing agent, and the inducing agent is at least a TGF-beta, a methotrexate, an ethanol, a $CCl_4$, a thioacetamide, a vinyl chloride, a vitamin A, a hepatitis, an nonalcoholic steatohepatitis, an inflammation, a D-galactosamine, a dimethylnitrosamine, a diethylnitrosamine, or any combination thereof.

In some embodiments, the phenotype characteristics further comprising an oxidative stress, and the oxidative stress is induced by an inducing agent, and the inducing agent is at least an reactive oxygen species, a $H_2O_2$, a superoxide radical, a hydroxy radical, a peroxynitrite, an acetaminophen, a glutathione depletion, a chloropropionic acid, an ethacrynic acid, a NAPQI, a buthionine sulfoximine, a $CCl_4$, a clozapine, a chlorpromazine, an estrogen, a selective estrogen receptor modulator, an iron, a copper, a chromium, a vanadium, a arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

In some embodiments of the liver disorder model, the non-parenchymal cells are derived from cells that exhibit at least one phenotype characteristic of a NAFLD as described herein prior to bioprinting of the liver tissue construct. In some embodiments, the parenchymal cells are derived from cells that exhibit at least one phenotype characteristic of a NAFLD as described herein prior to bioprinting of the liver tissue construct. In some embodiments, the non-parenchymal cells are derived from cells that exhibit at least one phenotype characteristic of a NASH as described herein prior to bioprinting of the liver tissue construct. In some embodiments, the parenchymal cells are derived from cells that exhibit at least one phenotype characteristic of a NASH as described herein prior to bioprinting of the liver tissue construct. In some embodiments, the non-parenchymal cells, the parenchymal cells, or a combination thereof are derived from the tissues of a human subject that had at least one phenotypic characteristic of a NAFLD or NASH as described herein, prior to bioprinting of the liver construct. In some embodiments, the cells are genetically modified to exhibit the at least one phenotype characteristic of a NAFLD as described herein prior to bioprinting of the liver tissue construct.

In some embodiments, the parenchymal cells are derived from one or more of the following sources: adult mammalian liver tissue; fetal mammalian liver tissue; embryonic stem cells (ESC); induced pluripotent stem cells (IPSC); adult stem/progenitor cells derived from the liver; and adult stem/progenitor cells derived from a tissue other than liver.

In some embodiments, the non-parenchymal cells comprise one or more of: endothelial cells, hepatic stellate cells, vascular cells, fibroblasts, mesenchymal cells, immune cells, Kupffer cells, biliary epithelial cells, biliary epithelial-like cells, sinusoidal endothelial cells, liver-derived stem/progenitor cells, adipocytes, adipocyte-like cells, and non-liver-derived stem/progenitor cells.

In some embodiments of the liver disorder model, a plurality of the liver tissue constructs are configured to form an array. In some embodiments, the array is present in wells of a microtiter plate.

In some embodiments of the liver disorder model, the parenchymal cells comprise a parenchymal bioink, the parenchymal bioink comprising at least hepatocytes or hepatocyte-like cells. In some embodiments, the parenchymal bioink further comprises Kupffer cells. In some embodiments, the non-parenchymal cells comprise a non-parenchymal bioink, the non-parenchymal bioink comprising non-parenchymal cells. In some embodiments, the non-parenchymal bioink comprises at least endothelial cells. In some embodiments, the non-parenchymal bioink further comprises hepatic stellate cells.

In some embodiments of the model, the parenchymal bioink further comprises an agent capable of inducing (i.e., an inducing agent) at least one phenotype characteristic of a lipid accumulation, an inflammation, an oxidative stress, a fibrosis, a hepatocellular ballooning, a microvesicular steatosis, a macrovesicular steatosis, or any combination thereof. In some embodiments of the model, the non-parenchymal bioink comprises an agent capable of inducing at least one phenotype characteristic of a lipid accumulation, an inflammation, an oxidative stress, a fibrosis, a hepatocellular ballooning, a microvesicular steatosis, a macrovesicular steatosis, or any combination thereof. In some embodiments, the agent is at least one of: a fatty acid, a free fatty acid, an unsaturated fatty acid, a saturated fatty acid, a palmitic acid, a linoleic acid, a linolenic acid, a myristic acid, an oleic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a cholesterol, a high glucose, a high insulin, a genipin, a amiodarone, a valproic acid, an ethanol, a fialuridine, a tamoxifen, a triglycerides, an olanzapine, a glucocorticoids, a IL-17A, an aflatoxin B1, a fructose, a HBx protein, a lipopolysaccharide (LPS), a IL-1β, a TNF-α, any agent that is capable of inducing the Kupffer cells to contribute to an inflammation, a TGF-β, a methotrexate, an ethanol, a $CCl_4$, a thioacetamide, a vinyl chloride, a vitamin A, a hepatitis, an nonalcoholic steatohepatitis, an inflammation, a D-galactosamine, a dimethylnitrosamine, a diethylnitrosamine, an reactive oxygen species, a $H_2O_2$, a superoxide radical, a hydroxy radical, a peroxynitrite, an acetaminophen, a glutathione depletion, a chloropropionic acid, an ethacrynic acid, a NAPQI, a buthionine sulfoximine, a $CCl_4$, a clozapine, a chlorpromazine, an estrogen, a selective estrogen receptor modulator, an iron, a copper, a chromium, a vanadium, a arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

In some embodiments of the model, the parenchymal bioink further comprises a candidate therapeutic agent. In some embodiments of the model, the non-parenchymal bioink comprises a candidate therapeutic agent. In some embodiments, the candidate therapeutic agent is selected from: a FXR agonist, a PPAR agonist, an ASK1 inhibitor, a GLP-1 agonist, a DPPIV inhibitor, an AMPK activator, a mTOR inhibitor, a 11B-HSD1 inhibitor, a FGF19 analogue, a FGF19 analogue, an anti-mRNA, a caspase inhibitor, a SCD1/ACC inhibitor, a LXRalpha inhibitor, a DGAT1 inhibitor, a vitamin E, a vitamin E analogue, a leptin receptor agonist, a statin, a cholesterol absorption inhibitor, an iBAT inhibitor, a KHK inhibitor, a galectin-3 inhibitor, a broad spectrum immunomodulator, an antioxidant, a TNFα inhibitor, a PDE inhibitor, an AT1 receptor agonist, a CCR2/CCR5 antagonist, a TLR4 antagonist, a LPS antibody, a LTD4 receptor antagonist, an inflammasome modulator, a LOXL2 immunotherapy, a HSP47 inhibitor, a TGFβ inhibitor, or any combination thereof.

In some embodiments of the model, the parenchymal bioink further comprises a genetic or epigenetic vector or molecule. In some embodiments of the model, the non-parenchymal bioink comprises a genetic or epigenetic vector or molecule.

In some embodiments, the parenchymal bioink includes hepatocytes (or hepatocyte-like cells) and Kupffer cells in a ratio of at least 90:10, 80:20, 70:30, 60:40, 50:50, 40:50, 30:70, 20:80, 10:90 or any intermediate ratio. In some embodiments, the non-parenchymal bioink includes endothelial cells and hepatic stellate cells in a ratio of at least 90:10, 80:20, 70:30, 60:40, 50:50, 40:50, 30:70, 20:80, 10:90 or any intermediate ratio.

Another advantage of bioprinting by the methods of this disclosure is that cells can be bioprinted at a high density and high viability. In certain embodiments, the density of the parenchymal cells is greater than $1 \times 10^6$ cells per mL. In certain embodiments, the density of the parenchymal cells is at least $5 \times 10^6$ cells per mL. In certain embodiments, the density of the parenchymal cells is at least $10 \times 10^6$ cells per mL. In certain embodiments, the density of the parenchymal cells is at least $20 \times 10^6$ cells per mL. In certain embodiments, the density of the parenchymal cells is at least $50 \times 10^6$ cells per mL. In certain embodiments, the density of the parenchymal cells is at least $100 \times 10^6$ cells per mL. In certain embodiments, the density of the parenchymal cells is at least $200 \times 10^6$ cells per mL. In certain embodiments, the density of the parenchymal cells is at least $500 \times 10^6$ cells per mL. In certain embodiments, the density of the parenchymal cells is between about $100 \times 10^6$ cells per mL and about $900 \times 10^6$ cells per mL. In certain embodiments, the density of the parenchymal cells is between about $100 \times 10^6$ cells per mL and about $700 \times 10^6$ cells per mL. In certain embodiments, the density of the parenchymal cells is between about $100 \times 10^6$ cells per mL and about $600 \times 10^6$ cells per mL. In certain embodiments, the density of the parenchymal cells is between about $100 \times 10^6$ cells per mL and about $500 \times 10^6$ cells per mL. In certain embodiments, the density of the parenchymal cells is between about $100 \times 10^6$ cells per mL and about $300 \times 10^6$ cells per mL. In certain embodiments, the density of the parenchymal cells is between about $100 \times 10^6$ cells per mL and about $200 \times 10^6$ cells per mL. In certain embodiments, the parenchymal cells is between 70%-100% living cells by volume. In certain embodiments, the viability of the parenchymal cells is greater than 99% living cells by volume. In certain embodiments, the viability of the parenchymal cells is greater than 95% living cells by volume. In certain embodiments, the viability of the parenchymal cells is greater than 90% living cells by volume. In certain embodiments, the viability of the parenchymal cells is greater than 80% living cells by volume. In certain embodiments, the viability of the parenchymal cells is greater than 70% living cells by volume. In certain embodiments, the viability of the parenchymal cells is greater than 60% living cells by volume. In certain embodiments, the viability of the parenchymal cells is greater than 50% living cells by volume. In certain embodiments, the viability of the parenchymal cells is 50-99% living cells by volume. In certain embodiments, this viability is maintained for at least 8, 12, 24, 48, 72, 96, or more hours post bioprinting. In certain embodiments, this viability is maintained for at least 1, 2, 3, 4, 5, 6, 7, 8, 9, 10, 11, 12, 13, 14, 21, or more days post printing.

In certain embodiments, the density of the non-parenchymal cells is greater than $1 \times 10^6$ cells per mL. In certain embodiments, the density of the non-parenchymal cells is at least $5 \times 10^6$ cells per mL. In certain embodiments, the density of the non-parenchymal cells is at least $10 \times 10^6$ cells per mL. In certain embodiments, the density of the non-parenchymal cells is at least $20 \times 10^6$ cells per mL. In certain embodiments, the density of the non-parenchymal cells is at least $50 \times 10^6$ cells per mL. In certain embodiments, the density of the non-parenchymal cells is at least $100 \times 10^6$ cells per mL. In certain embodiments, the density of the non-parenchymal cells is at least $200 \times 10^6$ cells per mL. In certain embodiments, the density of the non-parenchymal cells is at least $500 \times 10^6$ cells per mL. In certain embodiments, the density of the non-parenchymal cells is between about $100 \times 10^6$ cells per mL and about $900 \times 10^6$ cells per mL. In certain embodiments, the density of the non-parenchymal cells is between about $100 \times 10^6$ cells per mL and about $700 \times 10^6$ cells per mL. In certain embodiments, the density of the non-parenchymal cells is between about $100 \times 10^6$ cells per mL and about $600 \times 10^6$ cells per mL. In certain embodiments, the density of the non-parenchymal cells is between about $100 \times 10^6$ cells per mL and about $500 \times 10^6$ cells per mL. In certain embodiments, the density of the non-parenchymal cells is between about $100 \times 10^6$ cells per mL and about $300 \times 10^6$ cells per mL. In certain embodiments, the density of the non-parenchymal cells is between about $100 \times 10^6$ cells per mL and about $200 \times 10^6$ cells per mL. In certain embodiments, the non-parenchymal cells is between 70%-100% living cells by volume. In certain embodiments, the viability of the non-parenchymal cells is greater than 99% living cells by volume. In certain embodiments, the viability of the non-parenchymal cells is greater than 95% living cells by volume. In certain embodiments, the viability of the non-parenchymal cells is greater than 90% living cells by volume. In certain embodiments, the viability of the non-parenchymal cells is greater than 80% living cells by volume. In certain embodiments, the viability of the non-parenchymal cells is greater than 70% living cells by volume. In certain embodiments, the viability of the non-parenchymal cells is greater than 60% living cells by volume. In certain embodiments, the viability of the non-parenchymal cells is greater than 50% living cells by volume. In certain embodiments, the viability of the non-parenchymal cells is 50-99% living cells by volume. In certain embodiments, this viability is maintained for at least 8, 12, 24, 48, 72, 96, or more hours post bioprinting. In certain embodiments, this viability is maintained for at least 1, 2, 3, 4, 5, 6, 7, 8, 9, 10, 11, 12, 13, 14, 21, or more days post printing.

In some embodiments of the model, a parenchymal cell as described herein, a non-parenchymal cell as described herein, or a combination thereof is from a subject having a liver disorder, a subject predisposed to or at risk of developing a liver disorder, a subject without a liver disorder, or a subject with a disease other than a liver disorder. In some embodiments, the parenchymal cell, the non-parenchymal cell, or the combination thereof from the subject comprises diseased cells, non-diseased cells, or a combination thereof. In some embodiments, the liver tissue construct comprising cells from a subject is capable of exhibiting the at least one phenotype in the absence of induction of the phenotype by an inducing agent. In some embodiments, the subject has a liver disorder that shares a phenotype (i.e., one or more phenotypes) in common with the at least one phenotype exhibited by the liver tissue construct.

Disclosed are systems comprising a three-dimensional, engineered, bioprinted biological model of a liver disorder as disclosed herein or a liver tissue construct as disclosed herein and one or more of: an inducing agent as disclosed herein, a candidate therapeutic agent as disclosed herein, or a combination thereof.

In some embodiments of the models, systems, or methods as disclosed herein comprising cells from a subject, the model or method allows for modeling and elucidating donor heterogeneity (e.g., differential responses of diseased and/or non-diseased cells from different subjects with respect to: induction of a liver disorder as described herein, expression of biological molecules such as biomarkers, and/or responsiveness to a candidate therapeutic agent), mechanisms of disease progression, detection of biomarkers, assessment of candidate therapeutic agents, and/or the propensity of various donor backgrounds to a liver disorder as described herein (e.g., a NAFLD, including a NASH).

Methods of Making the Three-Dimensional (3D), Engineered, Bioprinted Liver Disorder Models Disclosed are methods of making a three-dimensional, engineered, bioprinted biological model of a liver disorder as described herein, comprising the steps of contacting a three-dimensional, engineered, bioprinted biological liver tissue construct with an agent (i.e., an inducing agent) that is capable of inducing the liver tissue construct to exhibit at least one phenotype characteristic of a liver disorder as described herein, provided that the three-dimensional, engineered, bioprinted, biological liver tissue construct comprises parenchymal cells and non-parenchymal cells, the parenchymal cells comprises hepatocytes and hepatocyte-like cells, and at least one component of the liver tissue construct is bioprinted.

In some embodiments, the liver tissue construct comprises a parenchymal cell as described herein, a non-parenchymal cell as described herein, or a combination thereof from a subject having a liver disorder.

Disclosed are methods of making a three-dimensional, engineered, bioprinted biological model of a liver disorder as described herein, comprising the steps of: producing a three-dimensional, engineered, bioprinted biological liver tissue construct that exhibits at least one phenotype characteristic of a liver disorder as described herein, wherein the construct comprises a parenchymal cell as described herein, a non-parenchymal cell as described herein, or a combination thereof from a subject having a liver disorder, provided that the three-dimensional, engineered, bioprinted, biological liver tissue construct comprises parenchymal cells and non-parenchymal cells, the parenchymal cells comprise hepatocytes and hepatocyte-like cells, and at least one component of the liver tissue construct is bioprinted.

In some embodiments, the parenchymal cell, the non-parenchymal cell, or the combination thereof from a subject having a liver disorder comprises diseased cells, non-diseased cells, or a combination thereof. In some embodiments, the liver disorder in the subject shares a phenotype (i.e., one or more phenotypes) in common with the at least one phenotype exhibited by the liver tissue construct.

In some embodiments, the liver disorder is selected from the group consisting of: a non-alcoholic fatty liver disease (NAFLD), a non-alcoholic steatohepatitis (NASH), hepatitis A, hepatitis B, hepatitis C, alpha-1-antitrypsin deficiency, cirrhosis, a cancer, hemochromatosis, alcohol-related liver disease, primary biliary cirrhosis, a drug-related injury, or any combination thereof.

In some embodiments of the method, the liver disorder is a non-alcoholic fatty liver disease (NAFLD), and the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof. In some embodiments, the NAFLD is a steatosis, and the liver tissue construct exhibits at least one phenotype that is at least a lipid accumulation. In some embodiments, the NAFLD is a non-alcoholic steatohepatitis (NASH), and the liver tissue construct exhibits at least two phenotypes selected from: a lipid accumulation, an inflammation, an oxidative stress, a fibrosis, a hepatocellular ballooning, a microvesicular steatosis, a macrovesicular steatosis, or any combination thereof. In some embodiments, the NAFLD is an intermediate state between a steatosis and a NASH, and the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof (1) Methods of Inducing the Liver Disorder In some embodiments, the liver tissue construct is induced to exhibit the at least one phenotype by contacting the liver tissue construct with at least one inducing agent selected from: a fatty acid, a free fatty acid, an unsaturated fatty acid, a saturated fatty acid, a palmitic acid, a linoleic acid, a linolenic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a myristic acid, an oleic acid, a stearic acid, a cholesterol, a high glucose, a high insulin, a fatty acid uptake enhancer, a genipin, a amiodarone, a valproic acid, an ethanol, a fialuridine, a tamoxifen, a triglycerides, an olanzapine, a glucocorticoids, an IL-17A, an aflatoxin B1, a fructose, a HBx protein, a lipopolysaccharide (LPS), an IL-1β, a TNF-α, an agent that is capable of activating the Kupffer cells to contribute to an inflammation, a TGF-β, a methotrexate, an ethanol, a CCl4, a thioacetamide, a vinyl chloride, a vitamin A, a hepatitis, an nonalcoholic steatohepatitis, an inflammation, a D-galactosamine, a dimethylnitrosamine, a diethylnitrosamine, a reactive oxygen species, a H2O2, a superoxide radical, a hydroxy radical, a peroxynitrite, an acetaminophen, a glutathione depletion, a chloropropionic acid, an ethacrynic acid, a NAPQI, a buthionine sulfoximine, a CCl4, a clozapine, a chlorpromazine, an estrogen, a selective estrogen receptor modulator, an iron, a copper, a chromium, a vanadium, an arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

In some embodiments, the liver tissue construct is induced to exhibit the at least one phenotype by a genetic or epigenetic modification. In some embodiments, the genetic or epigenetic modification is introduced, for example, by a genetic or epigenetic vector or molecule and/or a genetic engineering method such as, but not limited to, gene editing, gene knock-in, gene knock-out, gene knock-down, exosome-mediated transfer, or RNAi.

In some embodiments, the liver tissue construct is induced to exhibit at least one phenotype of a NAFLD by contacting the liver tissue construct with two or more agents selected from: a fructose, a glucose, a fatty acid, a lipopolysaccharide (LPS), a IL1β, or a TNFα. In some embodiments, the fatty acid is a free fatty acid, an unsaturated fatty acid, a saturated fatty acid, or any combination thereof. In some embodiments, fatty acid is a palmitic acid, an oleic acid, a linoleic acid, a linolenic acid, a myristic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, or any combination thereof. In some embodiments, the fatty acid is a palmitic acid and/or an oleic acid.

In some embodiments, the liver construct is induced to exhibit at least one phenotype that is a lipid accumulation by contacting the liver tissue construct with at least one inducing agent selected from: a fatty acid, a free fatty acid, an unsaturated fatty acid, a saturated fatty acid, a palmitic acid, a linoleic acid, a linolenic acid, a myristic acid, an oleic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a cholesterol, a high glucose, a high insulin, a genipin, an amiodarone, a valproic acid, an ethanol, a fialuridine, a tamoxifen, a triglycerides, an olanzapine, a glucocorticoids, a IL-17A, an aflatoxin B1, a fructose, a HBx protein, or any combination thereof.

In some embodiments, the liver construct is induced to exhibit at least one phenotype that is an inflammation, wherein the parenchymal cells further comprise Kupffer cells, and wherein the Kupffer cells to contribute to the inflammation. In some embodiments, the activation of Kupffer cells in the liver construct is associated with their origin from the tissue of a diseased subject.

In some embodiments, the liver construct is induced to exhibit at least one phenotype that is an inflammation, wherein the parenchymal cells further comprise Kupffer cells, and wherein the method comprises the step of activating the Kupffer cells to contribute to the inflammation. In some embodiments, the step of activating the Kupffer cells occurs before or after a step of inducing lipid accumulation in the liver tissue construct. In some embodiments, the step of activating the Kupffer cells comprises contacting the liver tissue construct with at least one inducing agent selected from: a lipopolysaccharide (LPS), a IL-1β, an agent that is capable of activating the Kupffer cells to contribute to the inflammation, or any combination thereof.

In some embodiments, the method further comprises contacting the liver tissue construct with a fatty acid uptake enhancer. In some embodiments, the fatty acid uptake enhancer is a genipin.

In some embodiments, the non-parenchymal cells of the method further comprise hepatic stellate cells, and the method comprises the step of activating the hepatic stellate cells to contribute to a fibrosis. In some embodiments, the step of activating the hepatic stellate cells occurs by activating the Kupffer cells, which in turn activate the hepatic stellate cells, thereby enabling the induction of an inflammation and the fibrosis to occur simultaneously.

In some embodiments, the liver construct is induced to exhibit at least one phenotype that is a fibrosis by contacting the liver tissue construct with at least one inducing agent selected from: a TGF-β, a methotrexate, an ethanol, a CCl4, a thioacetamide, a vinyl chloride, a vitamin A, a hepatitis, an nonalcoholic steatohepatitis, an inflammation, a D-galactosamine, a dimethylnitrosamine, a diethylnitrosamine, or any combination thereof.

In some embodiments, the liver construct is induced to exhibit at least one phenotype that is an oxidative stress by contacting the liver tissue construct with at least one inducing agent selected from: a reactive oxygen species, a H2O2, a superoxide radical, a hydroxy radical, a peroxynitrite, an acetaminophen, a glutathione depletion, a chloropropionic acid, an ethacrynic acid, a NAPQI, a buthionine sulfoximine, a CCl4, a clozapine, a chlorpromazine, an estrogen, a selective estrogen receptor modulator, an iron, a copper, a chromium, a vanadium, a arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

In some embodiments, the method comprises the step of simultaneously inducing any of the phenotypes as disclosed herein. In some embodiments, the method comprises the step of simultaneously inducing the phenotypes of an inflammation, a steatosis, an oxidative stress, and/or a fibrosis. In some embodiments, the method comprises the step of simultaneously inducing the phenotypes of an inflammation, an oxidative stress, and a fibrosis. In some embodiments, the method comprises the step of simultaneously inducing the phenotypes of an inflammation, a steatosis, and a fibrosis. In some embodiments, the method comprises the step of simultaneously inducing the phenotypes of an inflammation and a steatosis.

In some embodiments, the method comprises the step of inducing any one or more of the phenotypes as disclosed herein before any one or more of the other phenotypes as disclosed herein. In some embodiments, the method comprises the step of inducing the phenotype of a lipid accumulation before a step of simultaneously inducing the phentoypes of an inflammation, an oxidative stress, and a fibrosis. In some embodiments, the method comprises the step of inducing the phenotype of an inflammation before a step of simultaneously inducing the phentoypes of an steatosis and/or a fibrosis. In some embodiments, the method comprises the step of inducing the phenotype of an oxidative stress before a step of simultaneously inducing the phentoypes of an steatosis and/or a fibrosis.

In some embodiments, the liver construct is induced to exhibit at least one phenotype that is a lipid accumulation by culturing the liver tissue construct with adipocytes or adipocyte-like cells.

In some embodiments, the method comprises the step of inducing at least one phenotype characteristic of the liver disorder after the liver tissue construct is bio-printed. In some embodiments, the method comprises the step of inducing the at least one phenotype characteristic of the liver disorder before the liver tissue construct is bio-printed. In some embodiments, the method comprises the step of inducing the at least one phenotype characteristic of the liver disorder during the bio-printing of the liver tissue construct. In some embodiments, the method comprises the steps of inducing the at least one phenotype characteristic of the liver disorder before and after the liver tissue construct is bio-printed. In some embodiments, the method comprises the steps of inducing the at least one phenotype characteristic of the liver disorder before and during bioprinting of the liver tissue construct. In some embodiments, the method comprises the steps of inducing the at least one phenotype characteristic of the liver disorder during and after bioprinting of the liver tissue construct. In some embodiments, the method comprises the steps of inducing the at least one phenotype characteristic of the liver disorder before, during, and after the liver tissue construct is bio-printed. In some embodiments, the method comprises the steps of inducing a plurality of phenotype characteristics of the liver disorder before, during, and/or after bioprinting of the liver tissue construct.

(2) Methods of Inducing the Liver Disorder After Bioprinting of the Liver Tissue Construct In some embodiments, the method comprises the step of inducing at least one phenotype characteristic of the liver disorder after the liver tissue construct is bio-printed. In some embodiments, the at least one phenotype characteristic of the liver disorder is a lipid accumulation. In some embodiments, the step of inducing the lipid accumulation comprises applying an inducing agent, wherein the agent is at least one of: a fatty acid, a free fatty acid, an unsaturated fatty acid, a saturated fatty acid, a palmitic acid, a linoleic acid, a linolenic acid, a myristic acid, an oleic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a cholesterol, a high glucose, a high insulin, a genipin, a amiodarone, a valproic acid, an ethanol, a fialuridine, a tamoxifen, a triglycerides, an olanzapine, a glucocorticoids, a IL-17A, an aflatoxin B1, a fructose, a HBx protein, or any combination thereof. In some embodiments, the method further comprises the step of contacting the liver tissue construct with a fatty acid uptake enhancer. In some embodiments, the fatty acid uptake enhancer is a genipin.

In some embodiments, the liver disorder (e.g., a NAFLD) is induced by applying at least two agents (i.e., at least two inducing agents) to the liver tissue construct selected from: a fructose, a glucose, a fatty acid, a lipopolysaccharide (LPS), a IL113, or a TNFα.

In some embodiments, a fatty acid inducing agent has a concentration of: at least about 1 µM, at least about 5 µM, at least about 10 µM, at least about 15 µM, at least about 20 µM, at least about 25 µM, at least about 50 µM, at least about 75 µM, at least about 100 µM, at least about 200 µM, at least about 300 µM, at least about 400 µM, at least about 500 µM, at least about 600 µM, at least about 700 µM, at least about 800 µM, at least about 900 µM, at least about 1000 µM, or any concentration in-between. In some embodiments, a fatty acid inducing agent has a concentration of between about 1 µM and about 1000 µM, between about 10 µM and about 1000 µM, between about 25 µM and about 1000 µM, between about 50 µM and about 1000 µM, or between about 100 µM and about 1000 µM. In some embodiments, a fructose inducing agent has a concentration of at least about 1 mM, at least about 5 mM, or at least about 10 mM. In some embodiments, a fructose inducing agent has a concentration of between about 1 mM and about 50 mM. In some embodiments, the liver disorder is induced by applying a inducing agent (e.g., a fatty acid such as palmitic acid) daily or in a continuous, pulsed, or transient fashion over the course of at least 10 days, at least 14 days, at least 21 days. In some embodiments, an inducing agent (e.g., at least two inducing agents) is applied to the liver tissue construct for at least 1, 2, 3, 4, 5, 6, 7, 8, 9, 10, 11, 12, 13, 14, 15, 16, 17, 18, 19, 20, 21, 22, 23, 24, 25, 26, 27, 28 or any number of consecutive days.

An advantage of bioprinting by the methods of this disclosure is that cells be can precisely positioned to shorten the time need to induce a liver disorder (e.g., NASH). In particular, the parenchymal cells can be precisely positioned with respect to non-parenchymal cells for purposes of reducing the time needed to induce a liver disorder (e.g., NASH). In particular, the incorporation of Kupffer cells (KCs) and hepatic stellate cells (HSCs) into the liver tissue construct can enable a simultaneous induction of inflammation and fibrosis. In particular, activated KCs release soluble factors that active the nearby HSCs to initiate fibrosis. In some embodiments, the parenchymal cells comprise hepatocytes (or hepatocyte-like cells) and Kupffer cells and the non-parenchymal cells comprise endothelial cells and hepatic stellate cells.

In some embodiments of the method, the phenotype characteristic of the liver disorder further comprises an inflammation. In some embodiments, the parenchymal cells further comprises Kupffer cells, further comprising the step of activating the Kupffer cells to contribute to inflammation. In some embodiments, the step of activating the Kupffer cells occurs before or after the step of inducing lipid accumulation in the liver tissue construct. In some embodiments, the step of activating the Kupffer cells comprises contacting the liver tissue construct with a lipopolysaccharide (LPS), a IL-1β, an agent that is capable of inducing the Kupffer cells to contribute to the inflammation, or any combination thereof.

In some embodiments of the method, the phenotype characteristic of the liver disorder further comprises a fibrosis. In some embodiments, the non-parenchymal cells further comprises hepatic stellate cells, further comprising the step of activating the hepatic stellate cells contribute to the fibrosis. In some embodiments, the step of activating the hepatic stellate cells occurs by activating the Kupffer cells, which in turn activate the hepatic stellate cells, wherein the step of activating the hepatic stellate cells activates the Kupffer cells, or wherein the steps of activating the hepatic stellate cells and Kupffer cells occurs simultaneously, thereby enabling the induction of the inflammation and the fibrosis to occur simultaneously. In some embodiments, the liver tissue construct comprises at least one compartment comprising an interior defined by a border, the interior comprising the parenchymal cells, and the border comprising non-parenchymal cells. By having the hepatic stellate cells contribute to fibrosis in the non-parenchymal border, and simultaneously, the Kupffer cells contribute to inflammation in the parenchymal interior, the induction of a liver disorder (e.g., NASH) can be achieved in a shorter time period.

In some embodiments, the step of inducing the fibrosis is by contacting the liver tissue construct with an inducing agent that is at least one of: a TGF-beta, a methotrexate, an ethanol, a CCl4, a thioacetamide, a vinyl chloride, a vitamin A, a hepatitis, an nonalcoholic steatohepatitis, an inflammation, a D-galactosamine, a dimethylnitrosamine, a diethylnitrosamine, or any combination thereof.

In some embodiments, the phenotype characteristic of the liver disorder further comprises an oxidative stress, and the method further comprises the step of inducing the oxidative state by contacting the liver tissue construct with an inducing agent that is at least one of: a reactive oxygen species, a H2O2, a superoxide radical, a hydroxy radical, a peroxynitrite, an acetaminophen, a glutathione depletion, a chloropropionic acid, an ethacrynic acid, a NAPQI, a buthionine sulfoximine, a CCl4, a clozapine, a chlorpromazine, an estrogen, a selective estrogen receptor modulator, an iron, a copper, a chromium, a vanadium, a arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

In some embodiments, the step of inducing the lipid accumulation occurs before the step of inducing the inflammation. In some embodiments, the method further comprises the steps of inducing the oxidative stress and the fibrosis. In some embodiments, the step of inducing the inflammation, the oxidative stress, and the fibrosis occurs simultaneously. In some embodiments, the step of inducing the lipid accumulation occurs before the step of inducing the inflammation, the oxidative stress, and the fibrosis simultaneously.

The ability to simultaneously induce inflammation, the oxidative stress, and the fibrosis significantly reduces the amount of time needed to induce NASH, thereby enabling a longer period of time for drug testing.

Endogenous Disease Induction: Adipocyte-Liver Tissue Co-Culture.

Following differentiation of pre-adipocytes to mature adipocytes, adipocytes can be cultured in the receiver wells of a 24-well plate with liver tissues cultured in the 24-well transwell basket. The goal is for the adipocytes to provide an endogenous milieu of lipids as well as adipokines necessary for steatosis induction in liver tissues. Additionally, incorporation of a myeloid cell into the 3D liver tissue may facilitate modeling of NASH.

Endogenous Disease Induction: Adipocyte-Liver Tissue Geometry.

Pre-adipocytes could be printed in a NovoGel™ bioink formulation so that the adipocyte bioink forms, for example, a second border around the non-parenchymal border. The pre-adipocytes could then be differentiated to mature adipocytes in co-culture with the 30 liver tissue using media supplementation with factors such as insulin, 3-isobutyl-1-methylxanthine (IBMX), triiodothyronine, and glucose. Alternatively, insulin sensitizers may also be considered.

In some embodiments, the phenotype characteristic comprises a lipid accumulation, and the step of inducing the lipid accumulation in the liver tissue construct occurs by culturing the liver tissue construct with adipocytes or adipocyte-like cells. In some embodiments, the liver tissue construct further comprises adipocytes or adipocyte-like cells. In some embodiments, the liver tissue construct comprises at least one compartment comprising an interior defined by a border, the interior comprising the parenchymal cells, and the border comprising non-parenchymal cells. In some embodiments, the liver tissue construct further comprises a second border surrounding the border that defines the interior, the second border comprising adipocytes or adipocyte-like cells. In some embodiments, the compartment is defined by a planar geometry. In some embodiments, the liver tissue construct is at least three cells thick in its smallest dimension. In some embodiments, the liver tissue construct comprises a laminar geometry, wherein a first layer comprises the non-parenchymal cells and a second layer comprises parenchymal cells. In some embodiments, the non-parenchymal cells further comprise adipocytes or adipocyte-like cells. In some embodiments, the liver tissue construct further comprises a third layer of non-parenchymal cells, wherein the first layer is below the second layer, and the second layer is below the third layer.

In some embodiments of the method, the time period for inducing the liver disorder (e.g., NASH) post bio-printing of the liver tissue construct is 3, 7, 14, 21, 28 days or any number of days less than 28 days. In some embodiments, the induction of lipid accumulation occurs in 21 days or less. In some embodiments, the induction of at least two phenotypes characteristic of the liver disorder (e.g., NASH) occurs in 21 days or less.

In some embodiments of the method, a plurality of the liver tissue constructs are configured to form an array. In some embodiments, the array is present in wells of a microtiter plate.

In some embodiments of the method, the three-dimensional, engineered, bioprinted, biological liver tissue construct is affixed to a non-human animal such that the induction of the at least one characteristic phenotype of the liver disorder occurs after the liver tissue construct is affixed to the non-human animal. In some embodiments, the non-human animal is an immunocompromised rodent. In some embodiments, the non-human animal is reconstituted with a human immune system. In some embodiments, the liver tissue construct is affixed to the non-human animal by implanting the liver tissue construct into the non-human animal.

(3) Methods of Inducing the Liver Disorder Before and/or During Bioprinting of the Liver Tissue Construct In some embodiments, the method comprises the step of inducing at least one phenotype characteristic of the liver disorder during the bioprinting of the liver tissue construct. In some embodiments, the parenchymal cells comprise a parenchymal bioink, the parenchymal bioink comprises at least hepatocytes or hepatocyte-like cells. In some embodiments, the parenchymal bioink further comprises an agent (i.e., an inducing agent as described herein) capable of inducing at least one phenotype that is a lipid accumulation, an inflammation, an oxidative stress, a fibrosis, a hepatocellular ballooning, a microvesicular steatosis, a macrovesicular steatosis, or any combination thereof. In some embodiments, the non-parenchymal cells comprise a non-parenchymal bioink, the non-parenchymal bioink comprises non-parenchymal cells. In some embodiments, the non-parenchymal bioink comprises at least endothelial cells. In some embodiments, the non-parenchymal bioink further comprises hepatic stellate cells. In some embodiments, the non-parenchymal bioink comprises an agent (i.e., an inducing agent as described herein) capable of inducing at least one phenotype that is a lipid accumulation, an inflammation, an oxidative stress, a fibrosis, a hepatocellular ballooning, a microvesicular steatosis, a macrovesicular steatosis, or any combination thereof.

In some embodiments, the inducing agent is at least one of: a fatty acid, a free fatty acid, an unsaturated fatty acid, a saturated fatty acid, a palmitic acid, a linoleic acid, a linolenic acid, a myristic acid, an oleic acid, a stearic acid, a caproic acid, a caprylic acid, a capric acid, a lauric acid, a margaric acid, an arachidic acid, a behenic acid, a lignoceric acid, a palmitoleic acid, an erucic acid, an arachidonic acid, an alpha linolenic acid, a cholesterol, a high glucose, a high insulin, a genipin, a amiodarone, a valproic acid, an ethanol, a fialuridine, a tamoxifen, a triglycerides, an olanzapine, a glucocorticoids, a IL-17A, an aflatoxin B1, a fructose, a HBx protein, a lipopolysaccharide (LPS), a IL-1β, any agent that is capable of inducing the Kupffer cells to contribute to the inflammation, a TGF-beta, a methotrexate, an ethanol, a CCl4, a thioacetamide, a vinyl chloride, a vitamin A, a hepatitis, an nonalcoholic steatohepatitis, an inflammation, a D-galactosamine, a dimethylnitrosamine, a diethylnitrosamine, an reactive oxygen species, a H2O2, a superoxide radical, a hydroxy radical, a peroxynitrite, an acetaminophen, a glutathione depletion, a chloropropionic acid, an ethacrynic acid, a NAPQI, a buthionine sulfoximine, a CCl4, a clozapine, a chlorpromazine, an estrogen, a selective estrogen receptor modulator, an iron, a copper, a chromium, a vanadium, a arsenic, a cobalt, a cadmium, a quinone, a cisplatin, a cyclophosphamide, a doxorubicin, an acrylonitrile, a monosodium urate, a bortezomib, a paraquat, a silica nanoparticles, a PUFA, a PFOS, a PFOA, a pyrethroid pesticides, or any combination thereof.

As noted in the previous section, adipocytes or adipocyte-like cells can be incorporated into the tissue construct, such that the induction process can begin as earliest as during the bioprinting of the liver tissue construct before the liver tissue construct is completely bioprinted. In some embodiments, the phenotype characteristic comprises a lipid accumulation, and the step of inducing the lipid accumulation in the liver tissue construct occurs by culturing the liver tissue construct with adipocytes or adipocyte-like cells. In some embodiments, the liver tissue construct further comprises adipocytes or adipocyte-like cells. In some embodiments, the liver tissue construct comprises at least one compartment comprising an interior defined by a border, the interior comprising the parenchymal cells, and the border comprising non-parenchymal cells. In some embodiments, the liver tissue construct further comprises a second border surrounding the border that defines the interior, the second border comprises adipocytes or adipocyte-like cells. In some embodiments, the liver tissue construct comprises a laminar geometry, wherein a first layer comprises the non-parenchymal cells and a second layer comprises parenchymal cells. In some embodiments, the non-parenchymal cells comprise adipocytes or adipocyte-like cells. In some embodiments, the liver tissue construct further comprises a third layer of non-parenchymal cells, wherein the first layer is below the second layer, and the second layer is below the third layer.

Moreover, the induction process may have begun before bioprinting by virtue of the liver cells being in contact with the agent within the bioink. Additionally, in an effort to make the induction process as efficient as possible, the methods of inducing the liver disorder post-bioprinting, as articulated in the previous section, can still be applied to these liver tissue constructs having bioinks incorporated with agents for inducing the liver disorder. For example, the 3D bioprinted liver tissue construct can comprise a parenchymal region, wherein the parenchymal region comprises a bioink having hepatocytes, Kupffer cells, and a palmitic acid, and this liver tissue construct can be further induced post-bioprinting with additional palmitic acid and an agent that activates the Kupffer cells, such as LPS.

(4) Methods of Inducing the Liver Disorder Before Bioprinting of the Liver Tissue Construct Endogenous Disease Induction: Diseased Cell Sources Non-parenchymal cells sourced from patients with a clinically/pathologically diagnosed liver disorder (e.g., a steatosis and/or NASH) could be used to build the liver tissue. Such cells from a diseased liver have already received the necessary endogenous molecular cues to fuel their activation. Subsequently, culture media could be supplemented as described above to retain the diseased phenotype of the non-parenchymal cells in 3D culture. Additionally, disease hepatocytes may be similarly used in 3D bioprinted liver constructs and probed as to whether the disease phenotype may be retained in 3D culture.

In some embodiments, a parenchymal cell as described herein, a non-parenchymal cell as described herein, or a combination thereof is from a subject having a liver disorder. In some embodiments, the parenchymal cell, the non-parenchymal cell, or the combination thereof from the subject having a liver disorder comprises diseased cells, non-diseased cells, or a combination thereof. In some embodiments, the liver tissue construct comprising cells from a subject having a liver disorder is capable of exhibiting the at least one phenotype in the absence of induction of the phenotype by an inducing agent. In some embodiments, the liver disorder in the subject shares a phenotype (i.e., one or more phenotypes) in common with the at least one phenotype exhibited by the liver tissue construct.

In some embodiments, the method comprises the step of inducing at least one phenotype characteristic before the liver tissue construct is bio-printed. In some embodiments of the method, the non-parenchymal cells are derived from cells that exhibit at least one phenotype characteristic of the liver disorder (e.g., NAFLD) prior to bioprinting of the liver tissue construct. In some embodiments, the parenchymal cells are derived from cells that exhibit at least one phenotype characteristic of the liver disorder (e.g., NAFLD) prior to bioprinting of the liver tissue construct. In some embodiments, the non-parenchymal cells are derived from cells that exhibit at least one phenotype characteristic of the NASH prior to bioprinting of the liver tissue construct. In some embodiments, the parenchymal cells are derived from cells that exhibit at least one phenotype characteristic of the NASH prior to bioprinting of the liver tissue construct. In some embodiments, the cells are genetically modified to exhibit the at least one phenotype characteristic of the liver disorder (e.g., NAFLD) prior to bioprinting of the liver tissue construct. These cells exhibiting the phenotype characteristics of the liver disorder (e.g., NAFLD) can be directly incorporated into the bio-inks and used during the bio-printing of the liver tissue construct, thereby reducing or eliminating the induction time period post bio-printing. In turn, this enables a longer period of time to perform drug testing on the liver disorder model post bio-printing.

Even though the cells may exhibit the phenotype characteristic of the desired liver disorder, the methods of inducing the liver disorder before, during, and after bioprinting, as articulated in the previous sections, can still be applied to these tissue constructs in an effort to make the induction process as efficient as possible. For example, the 3D bioprinted liver tissue construct can comprise a parenchymal region, wherein the parenchymal region comprises a bioink having hepatocytes, Kupffer cells, and an LPS, the non-parenchymal region comprises endothelial cells and stellate cells, the hepatocytes and/or endothelial cells are derived from cells that already exhibit lipid accumulation, this liver tissue construct can be further induced post-bioprinting with a fatty acid uptake enhance (i.e., genipin) and an agent that activates the Kupffer cells, such as LPS.

Moreover, as noted in the previous section, the induction process may have begun before bioprinting by virtue of the liver cells being in contact with the agent within the bioink. Additionally, the methods of inducing the liver disorder post-bioprinting, as articulated in the previous section, can still be applied to these liver tissue constructs having bioinks incorporated with agents for inducing the liver disorder.

Methods of Using the Three-Dimensional, Engineered, Bioprinted Liver Disorder Models for Therapeutic Drug Testing, Such as Drug Efficacy and Toxicity Testing Disclosed are methods of assessing the ability of a candidate therapeutic agent to reverse, reduce or prevent a liver disorder, the method comprising contacting with a candidate therapeutic agent with a three-dimensional, engineered, bioprinted, biological liver tissue construct exhibiting at least one phenotype characteristic of a liver disorder as described herein, provided that the three-dimensional, engineered, bioprinted, biological liver tissue construct comprises parenchymal cells and non-parenchymal cells, the parenchymal cells comprises hepatocytes or hepatocyte-like cells, at least one component of the liver tissue construct is bioprinted; determining the viability or functionality of liver tissue cells; and assessing the ability of the candidate therapeutic agent to reverse, reduce or prevent the liver disorder based on the determined viability or functionality of the liver tissue cells as compared to a control liver tissue construct that does not exhibit the phenotype characteristic of the liver disorder. In some embodiments, the method further comprises removing the therapeutic agent; and assessing whether the absence of the agent results in improved viability or functionality of the liver tissue cells.

In some embodiments of the method, the liver disorder is a NAFLD. In some embodiments, the NAFLD is a steatosis, and the liver tissue construct exhibits at least one phenotype that is a lipid accumulation. In some embodiments, the NAFLD is a non-alcoholic steatohepatitis (NASH), and the liver tissue construct exhibits at least two phenotypes selected from: a lipid accumulation, an inflammation, an oxidative stress, a fibrosis, a hepatocellular ballooning, a microvesicular steatosis, a macrovesicular steatosis, or any combination thereof. In some embodiments, the NAFLD is an intermediate state between a steatosis and a NASH, and the liver tissue construct exhibits at least one phenotype selected from: a lipid accumulation, an inflammation, an oxidative stress, a fibrosis, a hepatocellular ballooning, a microvesicular steatosis, a macrovesicular steatosis, or any combination thereof.

In some embodiments, the step of assessing the ability of the candidate therapeutic agent to reverse, reduce or prevent the liver disorder includes assessing the ability of the candidate therapeutic agent to stop the progression of the liver disorder from a steatosis to a NASH. In some embodiments, the step of assessing the ability of the candidate therapeutic agent to reverse, reduce or prevent the liver disorder includes assessing the ability of the candidate therapeutic agent to stop the progression of the liver disorder from a steatosis to an intermediate state of NAFLD. In some embodiments, the step of assessing the ability of the candidate therapeutic agent to reverse, reduce or prevent the liver disorder includes assessing the ability of the candidate therapeutic agent to stop the progression of the liver disorder from a first intermediate state of NAFLD to a second intermediate state of NAFLD.

In some embodiments, the viability or functionality of the liver tissue cells is determined by measuring an indicator of metabolic activity. For example, cells comprising the construct can show evidence of viability and function in the form of a positive signal by ATP and/or alamarBlue, and liver function in the form of Albumin and/or Urea production. In some embodiments, the viability or functionality of the liver tissue cells is determined by evaluating, as compared to a control, one or more of the following activities: albumin production, urea production, alanine aminotransferase, LDH activity, histology, cell type-specific IHC, or any combination thereof. In some embodiments, the cell type-specific IHC is CD31, desmin, α-SMA, reelin, LOXL2, CK18, p62, CD11b, albumin, CD68, CD 163, or any combination thereof. In some embodiments, the viability or functionality of the liver tissue cells is determined by evaluating one or more of the following: Oil Red O, Perilipin IHC, PLIN5 IHC, Collagen I IHC, Collagen IV IHC, Sirius Red, fibrosis trichrome, or any combination thereof.

In some embodiments, the viability or functionality of the liver tissue cells is determined by evaluating, as compared to a control, gene and/or expression for one or more of the following: fatty acid regulation, hepatic stellate cell activation, or fibrosis.

In some embodiments, the gene expression for fatty acid regulation is CD36, FATP2, FATP5, FABP1, PPARs, or PPARγ. In some embodiments, the gene expression for hepatic stellate cell activation or fibrosis is a gene that is upregulated upon stellate cell activation, such as, for example, aTGFβ, a TIMP, a collagen, α-SMA, or any combination thereof. In some embodiments, the gene expression for hepatic stellate cell activation or fibrosis is a α-SMA, TGF-β1, TIMP1, COL1A1, COL4A3, or any combination thereof. In some embodiments, the gene expression for hepatic stellate cell activation or fibrosis is a gene associated with quiescence that may be reduced or lost upon hepatic stellate cell activation, such as, for example, desmin, GFAP, Reelin, LOXL2, retinoic acid, or any combination thereof. In some embodiments, the viability or functionality of the liver tissue cells is determined by evaluating, as compared to a control, the secretion of a pro-inflammatory cytokine. In some embodiments, the pro-inflammatory cytokine is one or more of: TNF-α, IL-1β, IL-1β, IL-6, IL-8, IL-2, IL-4, IL-12p70, IL-13, IFN-γ, or a combination thereof.

In some embodiments, at least the viability or functionality of the parenchymal cells is determined. In some embodiments, at least the viability or functionality of the non-parenchymal cells is determined. In some embodiments, at least the viability or functionality of the hepatocytes or hepatocyte-like cells is determined.

In some embodiments, the agent is an apoptosis signal-regulating kinsease 1 (ASK1) inhibitor. In some embodiments, the ASK1 inhibitor has a concentration of at least 20 nM. In some embodiments, the ASK1 inhibitor has a concentration of 20 nM to 200 nM. In some embodiments, the candidate therapeutic agent is assessed for at least 21 days, at least 14 days, at least 7 days, or any number of days. In some embodiments, the post-induction time period to evaluate the drug efficacy of a candidate therapeutic agent on the liver disorder model is 3, 7, 14, 21, 28 days or any number of days less than 28 days. The some embodiments of the method, a plurality of the liver tissue constructs are configured to form an array. In some embodiments, the array is present in wells of a microtiter plate.

In some embodiments, the method further comprising the step of assessing a toxicity of the candidate therapeutic agent on the liver tissue cells. In some embodiments, the toxicity is hepatotoxicity. In some embodiments, the hepatotoxicity is one or more of hepatocyte, endothelial cell, hepatic stellate cell, or Kupffer cell toxicity. In some embodiments, the viability or functionality of the liver tissue cells, and the toxicity of the liver cells, are assessed in a single well in a microtiter plate. In some embodiments, the viability or functionality of the liver tissue cells, and the toxicity of the liver cells, are assessed in a single well in a microtiter plate, by evaluating one or more markers specific to the liver disorder and a healthy liver cell. In some embodiments, wherein the liver cells evaluated for viability, functionality, or toxicity comprises at least parenchymal cells. In some embodiments, the parenchymal cells comprise hepatocytes or hepatocyte-like cells. In some embodiments, the parenchymal cells further comprise Kupffer cells. In some embodiments, wherein the liver cells evaluated for viability, functionality, or toxicity comprises at least non-parenchymal cells. In some embodiments, the non-parenchymal cells comprise endothelial cells. In some embodiments, the non-parenchymal cells further comprise hepatic stellate cells.

In some embodiments, the method further comprises the step of assessing a toxicity of the candidate therapeutic agent on a second three-dimensional, engineered, bioprinted biological liver tissue construct, wherein the second liver tissue construct does not exhibit the one phenotype characteristic of the liver disorder. In some embodiments, In some embodiments, the second liver tissue construct has no liver disorder. In some embodiments, the second liver tissue construct comprises parenchymal cells and non-parenchymal cells, the parenchymal cells comprises hepatocytes or hepatocyte-like cells, at least one component of the liver tissue construct is bioprinted. In some embodiments, the toxicity is hepatotoxicity. In some embodiment, the method further comprises the step of assessing the toxicity of the candidate therapeutic agent on the liver tissue construct that exhibits the liver disorder against the toxicity of the candidate therapeutic agent on the liver tissue construct that does not exhibit the liver disorder.

In some embodiments of the method, the three-dimensional, engineered, bioprinted, biological liver tissue construct is affixed to a non-human animal such that the candidate therapeutic agent is applied to the liver tissue construct while the liver tissue construct is affixed to the non-human animal. In some embodiments, the non-human animal is an immunocompromised rodent. In some embodiments, the non-human animal is reconstituted with a human immune system. In some embodiments, the liver tissue construct is affixed to the non-human animal by implanting the liver tissue construct into the non-human animal.

Methods of Simultaneously Inducing a Liver Disorder in a Bioprinted Liver Tissue Construct and Assessing a Candidate Therapeutic Agent's Ability to Reverse, Reduce, or Prevent the Liver Disorder In some embodiments of the methods of assessing the ability of a candidate therapeutic agent to reverse, reduce or prevent a liver disorder, the candidate therapeutic agent can be applied to a bioprinted liver tissue construct in the same time period in which an inducing agent as described herein is applied to the bioprinted liver tissue construct in order to induce a liver disorder. The candidate therapeutic agent can be any candidate therapeutic agent, as described throughout this present disclosure, that is capable of reversing, reducing or preventing a liver disorder or phenotype thereof, such as as NAFLD, NASH, a lipid accumulation, an inflammation, an oxidative stress, a fibrosis, a hepatocellular ballooning, a microvesicular steatosis, a macrovesicular steatosis, or any combination thereof. Similarly, the inducing agent can be any inducing agent, as described throughout this present disclosure, that is capable of inducing a liver disorder or phenotype thereof, such as NAFLD, NASH, a lipid accumulation, an inflammation, an oxidative stress, a fibrosis, a hepatocellular ballooning, a microvesicular steatosis, a macrovesicular steatosis, or any combination thereof. The candidate therapeutic agent and the inducing agent can both be applied daily to the bioprinted liver tissue construct during a first time period, which can be approximately 1, 2, 3, 4, 5, 6, 7, 8, 9, 10, 11, 12, 13, 14, 15, 16, 17, 18, 19, 20, 21, or any number of days. The ability of the candidate therapeutic agent to reverse, reduce or prevent the liver disorder can be assessed during this first time period. The bioprinted liver tissue construct can have any configuration, as described throughout this present disclosure. However, preferably, the bioprinted liver tissue construct is a three-dimensional, engineered, bioprinted, biological liver tissue construct having parenchymal cells and non-parenchymal cells, the parenchymal cells comprise hepatocytes and hepatocyte-like cells, and at least one component of the liver tissue construct is bioprinted.

As an example, the inducing agent having a fructose and a fatty acid can be applied daily to a bioprinted liver tissue for a first time period of up to 21 days or more in which a candidate therapeutic agent is also applied daily to the bioprinted liver tissue construct during this first time period. This inducing agent is designed to induce NAFLD, NASH, a lipid accumulation, an inflammation, an oxidative stress, a fibrosis, a hepatocellular ballooning, a microvesicular steatosis, a macrovesicular steatosis, or any combination thereof. The ability of drug modulators to reverse, reduce or prevent the liver disorder can be assessed during this first time period. Alternatively, after the first time period, the application of the inducing agent can be stopped while continuing the application of the candidate therapeutic acid for a second time period, which can be approximately 1, 2, 3, 4, 5, 6, 7, 8, 9, 10, 11, 12, 13, 14, 15, 16, 17, 18, 19, 20, 21, or any number of days. The ability of the candidate therapeutic agent to reverse, reduce or prevent the liver disorder can be also assessed be during this second time period, and collectively, both the first and the second time periods combined.

In some embodiments, the candidate therapeutic agent is selected from: a FXR agonist, a PPAR agonist, an ASK1 inhibitor, a GLP-1 agonist, a DPPIV inhibitor, an AMPK activator, a mTOR inhibitor, a 11B-HSD1 inhibitor, a FGF19 analogue, a FGF19 analogue, an anti-mRNA, a caspase inhibitor, a SCD1/ACC inhibitor, a LXRalpha inhibitor, a DGAT1 inhibitor, a vitamin E, a vitamin E analogue, a leptin receptor agonist, a statin, a cholesterol absorption inhibitor, an iBAT inhibitor, a KHK inhibitor, a galectin-3 inhibitor, a broad spectrum immunomodulator, an antioxidant, a TNFα inhibitor, a PDE inhibitor, an AT1 receptor agonist, a CCR2/CCR5 antagonist, a TLR4 antagonist, a LPS antibody, a LTD4 receptor antagonist, an inflammasome modulator, a LOXL2 immunotherapy, a HSP47 inhibitor, a TGFβ inhibitor, or any combination thereof.

Methods of Using the Three-Dimensional, Engineered, Bioprinted Liver Disorder Models for Biomarker Discovery Disclosed are methods of identifying a biomarker associated with at least one phenotype characteristic of a liver disorder, the method comprising: contacting a three-dimensional, engineered, bioprinted biological liver tissue construct with an inducing agent as described herein that is capable of inducing the liver tissue construct to exhibit the at least one phenotype as described herein, provided that the three-dimensional, engineered, bioprinted, biological liver tissue construct comprises parenchymal cells and non-parenchymal cells, the parenchymal cells comprise hepatocytes and hepatocyte-like cells, and at least one component of the liver tissue construct is bioprinted; and identifying a biomarker as a biological molecule that is differentially expressed by the construct that exhibits the at least one phenotype as compared to another construct. In some embodiments, the other construct is a control construct without the at least one phenotype (e.g., the construct that has not been contacted with an inducing agent (i.e., the liver construct in the absence of an inducing agent)). In some embodiments, the construct that is contacted with the inducing agent is a first construct and the other construct is a second construct that shares one or more phenotypes in common with the at least one phenotype of the first construct. In some embodiments, the second construct shares all phenotypes in common with the at least one phenotype of the first construct. In some embodiments, the at least one phenotype shared in common is associated with a less severe diseased state in the second construct as compared to the first construct. In some embodiments, the at least one phenotype shared in common is associated with a more severe diseased state in the second construct as compared to the first construct. In some embodiments, the method comprises comparing early disease, mid-disease, and/or late disease phenotypes by selecting for the severity and number of phenotypes in comparison constructs that develop over time.

Disclosed are methods of identifying a biomarker associated with at least one phenotype characteristic of a liver disorder as described herein, the method comprising: preparing a three-dimensional, engineered, bioprinted biological liver tissue construct that exhibits at least one phenotype characteristic of a liver disorder, wherein the construct comprises a parenchymal cell, a non-parenchymal cell, or a combination thereof from a subject having a liver disorder as described herein, provided that the three-dimensional, engineered, bioprinted, biological liver tissue construct comprises parenchymal cells and non-parenchymal cells, the parenchymal cells comprise hepatocytes and hepatocyte-like cells, and at least one component of the liver tissue construct is bioprinted; and identifying a biomarker as a biological molecule that is differentially expressed by the construct that exhibits the at least one phenotype as compared to another construct. In some embodiments, the other construct is a control construct without the at least one phenotype. In some embodiments, the construct that comprises a parenchymal cell, a non-parenchymal cell, or a combination thereof from a subject having a liver disorder is a first construct and the other construct is a second construct that shares one or more phenotypes in common with the at least one phenotype of the first construct. In some embodiments, the second construct shares all phenotypes in common with the at least one phenotype of the first construct. In some embodiments, the at least one phenotype shared in common is associated with a less severe diseased state in the second construct as compared to the first construct. In some embodiments, the at least one phenotype shared in common is associated with a more severe diseased state in the second construct as compared to the first construct. In some embodiments, the method comprises comparing early disease, mid-disease, and/or late disease phenotypes by selecting for the severity and number of phenotypes in comparison constructs that develop over time.

In certain embodiments, the method further comprises determining whether the biomarker is differentially expressed in liver tissue in a subject (i.e., a native tissue) having a liver disorder as compared to expression of the biological molecule in liver tissue in a subject without the liver disorder. In certain embodiments, the liver tissue in the subject having a liver disorder shares a phenotype (i.e., one or more phenotypes) in common with the at least one phenotype exhibited by the liver tissue construct.

For example, the overlap in differentially expressed biological molecules between healthy/diseased liver tissue constructs and healthy/diseased native tissues or in differentially expressed biological molecules in treated (e.g., with an inducing agent as described herein)/untreated liver tissue constructs and healthy/diseased native tissues can identify a candidate biomarker associated with diseased progression and/or a potential target for therapeutic treatment.

In certain embodiments, the biological molecule is a protein or a nucleic acid molecule. In certain embodiments, the biological molecule is a cytokine, DNA, or RNA. In certain embodiments, the biological molecule is a microRNA.

The expression or detection of the biological molecule can be determined by any standard procedure. In some embodiments, expression of the biological molecule is determined by performing a microarray analysis, RNA sequencing, or mass spectrometry.

Despite the rising prevalence of NAFLD and over 25 years of research on this disease there are currently no reliable methods for differentiating the different stages of NAFLD besides the highly invasive liver biopsies. While this limitation has prompted the investigation of novel circulating biomarkers to noninvasively differentiate different stages of the disease, the state-of-the-art is still not there yet largely due to the heterogeneity of NAFLD sampling in the clinic and the variability through NAFLD scoring sampling error from biopsies.

The 3D bioprinted liver tissue construct has the longevity and complexity that is missing in 2D cultures to model a chronic liver disease such as NAFLD over time, and can be used to identify non-invasive biomarkers between different stages of the disease.

In some embodiments, to identify potential biomarkers, various stages and severities of a liver disorder such as NAFLD are modeled and observed in the clinic by using various concentrations and combinations of lipids, lipid uptake enhancers, Kupffer cells, hepatic stellate cells, and inflammatory inducers. This approach enables a tight control of the severity of the various stages of a liver disorder such as NAFLD induced (e.g. NASH+/−fibrosis) in the 3D bioprinted liver tissue constructs thereby reducing the heterogeneity of tissue and media sampling for biomarker discovery.

In some embodiments, to identify potential non-invasive biomarkers to differentiate steatosis and NASH, and differentiate early and late stage NASH, media from steatosis and NASH 3D bioprinted liver disorder models are collected at various time points, then use a label free quantification mass spectrometry approach to evaluate differences in the secreted proteome between different stages of the disease. The levels of various microRNAs (miRNAs), present in isolated extracellular vesicle fractions found in the media, are evaluated using next generation RNA sequencing. To compare the present invention's in-vitro liver disorder models to clinical data, a qualified medial professional, such as a pathologist, can score the in-vitro liver disorder tissues for steatosis, hepatocellular ballooning, and fibrosis using the NASH and fibrosis scoring system, then using available serum samples from NAFLD patients with comparable steatosis, hepatocellular ballooning, and fibrosis scoring, compare the histopathology, secreted proteome, and RNA sequencing profiles between our in vitro samples and clinical samples to potentially identify biomarkers that can delineate the various stages of NAFLD. By tailoring the severity of the various stages of NAFLD in the present invention's in-vitro liver disorder models to match patient samples, the fate of potential biomarkers throughout disease progression can be assessed. Ideal non-invasive biomarkers found in the steatosis and NASH 3D bioprinted liver tissue constructs should not only reflect the presence of NAFLD, but also the severity of the disease, which is essential for early disease diagnosis.

Disclosed are methods of using a three-dimensional, engineered, bioprinted liver tissue construct for biomarker discovery, the method comprising the steps of: receiving a plurality of first media, at a pre-determined frequency, from a first three-dimensional, engineered, bioprinted liver tissue construct exhibiting a first non-alcoholic fatty liver disease (NAFLD); receiving a plurality of second media, at the pre-determined frequency, from a second three-dimensional, engineered, bioprinted liver tissue construct exhibiting a second NAFLD; evaluating the plurality of first and second media for genetic information; and identifying one or more biomarkers that differentiate the first liver tissue construct from the second liver tissue construct based on the evaluated genetic information.

In some embodiments of the method, the first NAFLD is a steatosis and the second NAFLD is a non-alcoholic steatohepatitis (NASH). In some embodiments, the first NAFLD is a steatosis and the second NAFLD is an intermediate state between the steatosis and a NASH. In some embodiments, the first NAFLD is a NASH and the second NAFLD is an intermediate state between the steatosis and a NASH. In some embodiments, the first NAFLD is a first intermediate state between a steatosis and a NASH, the second NAFLD is a second intermediate state between the steatosis and the NASH, and the second NAFLD is different from the first NAFLD. In some embodiments, the intermediate state includes at least two phenotype characteristics of: a lipid accumulation, an inflammation, an oxidative stress, a fibrosis, or any combination thereof. In some embodiments, the intermediate state includes at least three phenotype characteristics of: a lipid accumulation, an inflammation, an oxidative stress, a fibrosis, or any combination thereof.

In some embodiments of the method, the first liver construct exhibits a homogenous liver disorder, the homogenous liver disorder is the first NAFLD and no other liver disorder. In some embodiments, the second liver construct exhibits a homogenous liver disorder, the homogenous liver disorder is the second NAFLD and no other liver disorder. In some embodiments, the first liver construct exhibits a heterogeneous liver disorder, the heterogeneous disorder comprises the first NAFLD and at least one other liver disorder. In some embodiments, the at least one other liver disorder includes at least one of hepatitis A, hepatitis B, hepatitis C, alpha-1-antitrypsin deficiency, cirrhosis, cancer, hemochromatosis, alcohol-related liver disease, primary biliary cirrhosis, a drug-related injury, or any combination thereof. In some embodiments, the second liver construct exhibits a homogenous liver disorder, the homogenous liver disorder is the second NAFLD and no other liver disorder.

In some embodiments of the method, the pre-determined frequency is daily for at least 21 days. In some embodiments, the pre-determined frequency is daily for at least 14 days. In some embodiments, the pre-determined frequency is daily for at least 7 days. In some embodiments, the pre-determined frequency once every 1, 2, 3, 4, 5, 6, 7, 8, 9, 10, 11, 12, 13, 14, 15, 16, 17, 18, 19, 20, 21, 22, 23, 24, 25, 26, or 27 days.

In some embodiments of the method, the steps of evaluating the plurality of first and second media for genetic information comprises determining RNA levels in the plurality of first and second media by performing RNA sequencing on RNAs from the plurality of first and second media. In some embodiments, the RNAs are microRNAs. In some embodiments, the RNAs are from isolated extracellular vesicle fractions found in the plurality of first and second media. In some embodiments, the steps of evaluating the plurality of first and second media for genetic information comprises determining differences in proteome secreted by the plurality of first and second media by performing mass spectrometry on the plurality of first and second media. In some embodiments, the mass spectrometry is a label free quantification mass spectrometry.

In some embodiments, the method further comprises the step of determining one or more mediators from at the least plurality of the first media, wherein the mediator is indicative of a future state of NAFLD. For example, if the first media is from a tissue construct exhibiting a steatosis, the determined mediator can indicate that the steatosis is progressing to a later stage of NAFLD, such as NASH or an intermediate state between steatosis and NASH.

Biomarker discovery is difficult to ascertain from patient samples because patients having liver disorders may suffer from several different liver disorders at any one time, such as a combination any one or more of NAFLD, steatosis, NASH, hepatitis A, hepatitis B, hepatitis C, alpha-1-antitrypsin deficiency, cancer, hemochromatosis, alcohol-related liver disease, and primary biliary cirrhosis, and a drug-related injury. As such, it is difficult to isolate a biomarker specific to only one liver disorder. For example, if there are two patients, one patient has steatosis, and another patient has NASH, it is still difficult to isolate the biomarker that differentiates steatosis from NASH because these two patients are likely to each exhibit phenotype characteristic of several different liver disorders. Therefore, the 3D bioprinted liver tissue construct solves this technical challenge because the present invention provides models and methods to create a liver tissue construct exhibits only one liver disorder and no other liver disorder, thereby homogenizing the liver disorder to only one type. For example, two 3D bioprinted liver tissue constructs can be created, one liver tissue construct exhibiting only steatosis, and another liver tissue construct exhibiting only NASH, and by evaluating the genetic differences between these two liver tissue constructs, a biomarker that differentiates steatosis from NASH can be ascertained. Similarly, biomarkers for different stages of NAFLD can be ascertained by, for example, creating two 3D bioprinted liver tissue constructs, one liver tissue construct exhibiting only steatosis, and another liver tissue construct exhibiting an intermediate state of NAFLD. Ultimately, being able to discover such biomarkers can led to better clinical diagnostics and therapeutic drugs for NAFLD, steatosis, and NASH.

Disclosed are methods of using a three-dimensional, engineered, bioprinted liver tissue construct for biomarker discovery, the method comprising the steps of: receiving a plurality of media from a three-dimensional, engineered, bioprinted liver tissue construct exhibiting only a non-alcoholic fatty liver disease (NAFLD); receiving a plurality of serum from a patient with a comparable NAFLD and at least one other liver disorder; evaluating the plurality of media from the liver tissue construct for genetic information; evaluating the plurality of serum from the patient with the comparable NAFLD for genetic information; and identifying one or more biomarkers that differentiate the evaluated genetic information of the liver tissue construct from the evaluated genetic information of the patient. In some embodiments, the NAFLD is steatosis. In some embodiments, the NAFLD is NASH. In some embodiments, the NAFLD is an intermediate state between the steatosis and a NASH. In some embodiments, the one other liver disorder includes at least one of hepatitis A, hepatitis B, hepatitis C, alpha-1-antitrypsin deficiency, cirrhosis, cancer, hemochromatosis, alcohol-related liver disease, primary biliary cirrhosis, a drug-related injury, or any combination thereof.

In some embodiments of the method, the steps of evaluating the plurality of media from the liver construct and evaluating the plurality of serum from the patient comprises performing RNA sequencing on RNAs from the plurality of media and serum. In some embodiments, the RNAs are microRNAs. In some embodiments, the RNAs from the plurality of media is from isolated extracellular vesicle fractions in the plurality of media. In some embodiments, the step of evaluating the plurality of first and second media for genetic information comprises determining differences in proteome secreted by the plurality of first and second media by performing mass spectrometry on the plurality of first and second media. In some embodiments, the mass spectrometry is a label free quantification mass spectrometry. In some embodiments, the method further comprises the steps of evaluating a histopathology of the tissue construct and a histopathology of a liver sample from the patient.

EXAMPLES

The following specific examples are to be construed as merely illustrative, and not limitative of the remainder of the disclosure in any way whatsoever.

Example 1

Liver Tissue Bioprinted Using Continuous Deposition and Tessellated Functional Unit Structure Engineered liver tissue was bioprinted utilizing a Novo-Gen MMX Bioprinter™ (Organovo, Inc., San Diego, Calif.) using a continuous deposition mechanism. The three-dimensional structure of the liver tissue was based on a repeating functional unit, in this case, a hexagon. The bio-ink was composed of hepatic stellate cells and endothelial cells encapsulated in an extrusion compound (surfactant polyol—PF-127).

Preparation of 30% PF-127

A 30% PF-127 solution (w/w) was made using PBS. PF-127 powder was mixed with chilled PBS using a magnetic stir plate maintained at 4° C. Complete dissolution occurred in approximately 48 hours.

Cell Preparation and Bioprinting

A cell suspension comprised of 82% stellate cells (SC) and 18% human aortic endothelial cells (HAEC) and human adult dermal fibroblasts (HDFa) was separated into 15 mL tubes in order to achieve three cell concentrations: $50 \times 10^6$ cells/mL, $100 \times 10^6$ cells/mL, and $200 \times 10^6$ cells/mL following centrifugation. Each cell pellet was resuspended in 30% PF-127 and aspirated into a 3 cc reservoir using the bioprinter. With a 510 µm dispense tip, the encapsulated cells were bioprinted onto a PDMS base plate into a single hexagon (see FIG. 6A) or hexagon tessellation configuration (see FIG. 6B). Each construct received approximately 200 µL of media and was incubated for 20 minutes at room temperature to evaluate construct integrity.

Multi-Layer Bioprinting

For hexagon tessellation experiments, up to (4) sequential layers were bioprinted resulting in a taller structure with more cellular material present. Following fabrication, each construct initially received approximately 200 µL of complete media to assess construct integrity. Constructs were incubated for 20 minutes at room temperature and were then submerged in 20 mLs of complete media.

Results

Figure 7:
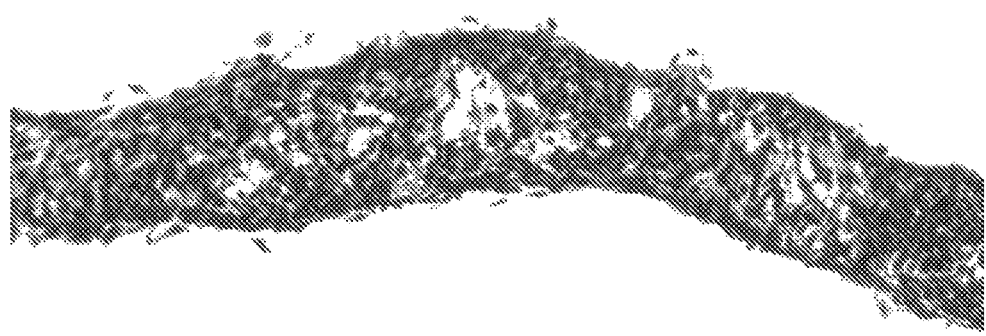
FIG. 7 is a non-limiting photomicrograph of the tessellated construct of FIG. 6, depicting an exemplary "spoke" in the tessellated construct. This photomicrograph demonstrates Hematoxylin and Eosin staining of formalin-fixed paraffin-embedded tissue sections of stellate cells, endothelial cells, and dermal fibroblasts bioprinted by continuous deposition in a multi-layer tessellated hexagonal structure and then cultured for 16 hours.

Following 18 hours of culture in growth media containing 10% fetal bovine serum (which dissolves PF127), cells contained within the bioprinted geometry were cohered to each other sufficiently to generate an intact, contiguous sheet of tissue that retained the geometrical patterning of the original design (see FIG. 6D). Shown in FIG. 7 is H&E staining of a single segment of the tessellated construct, after fixation in 10% neutral buffered formalin. Cells were found to be viable, intact, and confined to their original printed geometry.

Example 2

Forced Layering

Cell populations (homogeneous or heterogeneous) were prepared for bioprinting as either cylindrical bio-ink or as a cell suspension in Pluronic F-127 (Lutrol, BASF). Briefly, for preparation of bio-ink, cells were liberated from standard tissue culture plastic using either recombinant human trypsin (75 µg/mL, Roche) or 0.05% trypsin (Invitrogen). Following enzyme liberation, cells were washed, collected, counted and combined at desired ratios (i.e., 50:50 hepatic stellate cell (hSC): endothelial cell (EC)) and pelleted by centrifugation. Supernatant was then removed from the cell pellet and the cell mixture was aspirated into a glass microcapillary of desired diameter, typically 500 µm or 250 µm, internal diameter. This cylindrical cell preparation was then extruded into a mold, generated from non cell-adherent hydrogel material with channels for bio-ink maturation. The resulting bio-ink cylinders were then cultured in complete cell culture media for an empirically determined amount of time, typically 2 to 24 hours.

Briefly, for hydrogel cell suspension preparation, cells were liberated from standard cell culture vessel using either of the enzyme-mediated protocols described herein. Liberated cells were then washed with serum containing media, collected, counted and centrifuged to form a dense cell pellet. Supernatant was removed from the resulting cell pellet and cells were then resuspended in cold PF-127 (4° C.) at a concentration of 50 to $200 \times 10^6$ cells/mL (ranging from 10 to $300 \times 10^6$ cells/mL). This cell suspension was then aspirated into a syringe, utilizing a NovoGen Bioprinter™ MMX (Organovo, Inc., San Diego, Calif.).

Fabrication of tissue constructs with forced cell patterning, layering, or orientation was then accomplished using the bioprinter. Bioprinting of three-dimensional tissue constructs was performed with cylindrical bio-ink, cellular suspensions in water soluble gels, or combinations thereof. To achieve defined cell patterning or layering, combinations of relevant cell populations were included in the bio-ink or cell suspension preparation and then bioprinted in such a fashion that dissolution of the gel material supporting the cell solution, results in defined cell layering around the deposited bio-ink (see FIG. 13). Cell patterning, organization, or layering was also achieved through the utilization and incorporation of defined, discrete cell populations (e.g., hSC and EC), which resulted in predictable and repeatable organization of cells and cellular structures within the bioprinted tissues (see FIG. 14).

In some experiments, final cellular organization within the bioprinted neotissue was observed after a maturation or culture period. Constructs were maintained in a standard laboratory incubator (37° C., humidified chamber supplemented with 5% $CO_2$) and evaluated over time.

Results

Cell patterning, layering, or arrangement was achieved using bioprinting. By bioprinting with bio-ink containing heterogeneous (i.e., polytypic) cell populations, or by combining bio-ink (homogeneous or heterogeneous cell populations) with high density cell-gel or cell suspensions, distinct cell organization was observed. Maturation of these neotissue constructs in a humidified chamber (incubator) resulted in further establishment of distinct cell arrangement, organization and/or segregation in these bioprinted neotissues.

For example, bioprinting of EC:hSC-laden PF-127 on top of bioprinted bio-ink comprising HepG2 cells results in the establishment of distinct layers of the construct with distinct cell populations and discreet tissue morphology. In the case of bio-ink constructs containing hSC and EC, bioprinted constructs that were matured for more than 3 days in complete media were found to contain a distinct layer of EC at the periphery and organized microvessel networks within the core of the construct. Bioprinted constructs fabricated with bio-ink comprising a homogeneous (i.e., monotypic) population of vascular smooth muscle cell onto which a highly concentrated solution of EC was bioprinted were found to contain a distinct layer of EC at the periphery of the construct.

Example 3

Multi-Well Plates

Cell populations (homogeneous or heterogeneous) were prepared for bioprinting using a variety of bio-ink formats, including cylindrical bio-ink aggregates, suspensions of cellular aggregates, or cell suspensions/pastes, optionally containing extrusion compounds. Briefly, for preparation of cylindrical bio-ink, cells were liberated from standard tissue culture plastic using either recombinant human trypsin (75 μg/mL, Roche) or 0.05% trypsin (Invitrogen). Following enzyme liberation, cells were washed, collected, counted, and combined at desired ratios (i.e., 50:50 hepatic stellate cell (hSC): endothelial cell (EC)) and pelleted by centrifugation. Supernatant was then removed from the cell pellet and the cell mixture was aspirated into a glass microcapillary of desired diameter, typically 500 μm or 250 μm, internal diameter. This cylindrical cell preparation was then extruded into a mold, generated from non cell-adherent hydrogel material with channels for bio-ink maturation. The resulting bio-ink cylinders were then cultured in complete cell culture media for an empirically determined amount of time, typically 2 to 24 hours.

For preparation of a cell suspension or cell paste of cellular aggregates, the cell propagation and liberation protocols described herein were followed. At the time of cell pellet generation, supernatant was removed from the pellet and the pellet was transferred to a custom deposition syringe. This syringe was then mounted to the bioprinter deposition head for direct bioprinting of the cell aggregate solution or paste into multi-well plates.

Replicate tissue constructs were then bioprinted within the wells of either a multi-well tissue culture plate (e.g., 6-well or 24-well) or within a multi-well cell culture insert (i.e., Transwell, BD) and then placed into an appropriate multi-well plate. Following bioprinting, the three-dimensional constructs were matured/conditioned with relevant media for some period of time, typically 3 to 14 days. Following maturation, constructs were harvested, fixed and processed for routine histology and immunohistochemistry.

Results

Bioprinted tissues were successfully fabricated within multi-well culture plates or multi-well culture inserts that were then inserted into multi-well plates. This approach allows for generation of replicate bioprinted tissues that are optionally cultured and treated to generate identical or unique culture conditions. This approach results in a significant increase in bioprinting process throughput and sample generation (see FIG. 16).

Example 4

Stimulation of Bioprinted Neotissues

Cylindrical bio-ink comprising relevant heterogeneous (i.e., polytypic) cell populations were prepared. Physiologically-relevant populations (e.g., hepatic stellate cells (hSC) and human aortic endothelial cells (EC)) of cells were combined at specific ratios to generate proper bio-ink. Cells were maintained and propagated under standard laboratory conditions and cells were cultured in media either purchased from the same vendor as the cells, or media comprising components typically found in the primary literature to be conducive to standard cell culture practices for those particular cell types. Cell processing for bio-ink preparation was as follows: briefly, cells were liberated from standard tissue culture plastic by washing with cation-free phosphate buffered saline (PBS) and then exposed to 0.1-0.05% trypsin (Invitrogen). Liberated cells were then washed in serum-containing media, collected, counted, and combined in an appropriate ratio for the stimulation assay or experiment being conducted, and pelleted by centrifugation. Supernatant was then removed and the cell pellet was aspirated into a glass microcapillary, which was then submerged in complete media for approximately 15 to 20 minutes. This cylindrical bio-ink structure was then extruded into a non cell-adherent hydrogel mold, containing linear channels and held for 2 to 18 hours. Cylindrical bio-ink containing hSC: EC was then used to fabricate bioprinted tissue constructs and maintained and/or matured in a humidified chamber. Tissue segments were fabricated with initial dimensions of 1.25 mm×8 mm×0.25 mm (W×L×H). During the post-bioprinting maturation period some constructs were exposed to the cytokine TGF-β1 to elicit a tissue-specific response (see FIG. 15).

For tissue constructs requiring a homogeneous (i.e., monotypic) cell layer, restricted to the upper surface, a secondary cell preparation was utilized containing the relevant cell type. Typically vascular endothelial cells or small airway epithelial cells (for blood vessel wall and human lung tissue models, respectively) were prepared in a highly concentrated cell suspension. Briefly, cells were liberated as described above, collected, enumerated and pelleted by centrifugation. Supernatant was removed and the cell pellet was resuspended in a small volume of complete media, yielding a highly concentrated cell pellet of $1\times10^5$ cells/μL. This cell suspension was then stored at 4° C. until time of use.

The bioprinted neotissues were then submerged in serum-containing complete cell culture media and placed in a standard humidified chamber, supplemented with 5% CO2 for maturation. The bioprinted neotissues were then cultured and stimulated with a relevant cytokine(s) for a predetermined period of time, formalin-fixed, harvested, and processed for standard histology and immunohistochemistry. The bioprinted tissues were evaluated for characteristics such as, but not limited to for tissue morphology, cell organization, extracellular matrix production, cell proliferation, cell viability, and construct integrity.

Cytokine stimulation was conducted by adding cytokine directly to the culture media and incubating the bioprinted tissues with the added protein to provide direct and prolonged cell access to the proper stimulus. Dose-response experiments were conducted at doses typically ranging from 0.1 to 100 ng/mL, dependent on the ED50 of the experimental cytokine. For experiments in which cytokine stimulation was conducted over more than 48 hours, media was changed and fresh cytokine was added every 48 hours.

Results

Bioprinted neotissues containing physiologically-relevant populations of cells were successfully stimulated with cytokines that had been previously demonstrated to elicit cellular responses in two-dimensional in vitro systems. The responses observed in the bioprinted three-dimensional tissue constructs were observed to be dose-dependent and unique to the cells within the bioprinted construct (see, e.g., FIG. 15).

Example 5

Bioprinting of Co-Molded Functional Liver Tissue Microstructure with Continuous Deposition
Preparation of 30% PF-127

A 30% PF-127 solution (w/w) was made using PBS. PF-127 powder was mixed with chilled PBS using a magnetic stir plate maintained at 4° C. Complete dissolution occurred in approximately 48 hours.
Cell Preparation and Co-Printing of Mold and Fill Three mL of PF-127 solution was aspirated into a 3 cc reservoir using the bioprinter and with a 510 μm dispense tip, 30% PF-127 solution was bioprinted onto a 6 well Transwell into a single hexagon shape and layered sequentially 6 times.

A cell suspension, comprised of $7.8 \times 10^7$ hepatic cells (HepG2), was centrifuged at 1000 g for 6 minutes to create the cell paste. Five μL of cell paste was extruded through a 510 μm needle to fill each of the triangular molds (see FIG. 5A). The hexagon mold was incubated at room temperature for 15 minutes. Three mL of media (DMEM supplemented with 10% FBS and 1× penicillin, streptomycin and amphotericin B) was added to the well with the Transwell supported above followed by incubation at 37° C. and 5% CO2. Within 45 minutes the PF-127 mold dissolved into the media leaving the molded hepatic bio-ink intact to form a planar geometry of cells and void spaces (see FIG. 5B). To remove residual PF-127 from the media, the Transwell was transferred into a new well containing 3 mL of media and incubated for two hours. This was repeated an additional 2 times for a total media exchange of 9 mL over 6 hours.

Post 6 hours the Transwell was transferred to a new well with no media and a cell suspension of $2 \times 10^6$ cells, at a ratio of human aortic endothelial cells at 90% and 10% hepatic stellate cells, was dispensed to fill the voids created by the dissolution of PF-127 mold. The hepatic constructs were incubated for 15 minutes at room temperature. Following the 15 minute incubation, 4 mL of media containing a ratio of 85% media (DMEM supplemented with 10% FBS and 1× penicillin, streptomycin and amphotericin B, to support the hepatic and stellate cells and 15% M199 supplemented with 2% LSGS, 10% FBS, HEPES and 1× penicillin, streptomycin and amphotericin B, to support the human aortic endothelial cells). The construct was incubated at 37° C. and 5% CO2 for 48 hours to form a contiguous construct, with planar geometry comprising a lobular (triangular) arrangement of hepatic parenchyma with intervening endothelial cell-comprising tissue.

Example 6

Bioprinted Liver Tissue 3D bioprinted liver tissues comprised of cryopreserved primary human hepatocytes (Life Technologies, Carlsbad, CA, USA), hepatic stellate cells (ScienCell; Carlsbad, CA, USA), and HUVEC cells (Becton Dickinson; Tewksbury, MA, USA) were bioprinted directly into 24-well Transwell plates (FIG. 20A) using the Organovo NovoGen Bioprinter Instrument (Organovo, San Diego, CA, USA).

Briefly, hepatic stellate cells and HUVEC cells were propagated per the manufacturer's instructions prior to tissue fabrication. Cryopreserved hepatocytes were thawed and prepared for use per the manufacturer's instructions. Separate high density bioinks comprising parenchymal cells (100% cellular paste, generated via compaction having hepatocyte cells) or nonparenchymal cells (150e6 cells/mL of endothelial cells and hepatic stellate cells formulated in hydrogel) were prepared and loaded into separate heads of the NovoGen Bioprinter Instrument within a standard biosafety cabinet. A computer script was then executed to deposit the bioinks in a two-compartment planar geometry ($2 \text{ mm}^2 \times 0.5 \text{ mm}$) onto the membranes of standard 24-well 0.4 μm transwell culture inserts (Corning, Tewksbury, MA USA) via continuous deposition microextrusion with the non-parenchymal cells comprising the border regions of each compartment and the parenchymal cells filling each compartment. Following fabrication, the tissues were fed daily with 600 μL of 3D Liver Tissue Media, consisting of DMEM supplemented with Primary Hepatocyte Maintenance Supplements (Life Technologies, Carlsbad, CA, USA) and EGM-2 (Lonza, Basel, Switzerland), and incubated at 37° C. under humidified atmospheric conditions supplemented with 5% CO2. Tissues were allowed to mature in culture for at least three days following fabrication prior to initiation of experimentation, and were substantially free of pre-formed scaffold at the time of use. For the one month timecourse, tissues were fed daily for a total of 28 days post-fabrication.

Results

Figure 20:
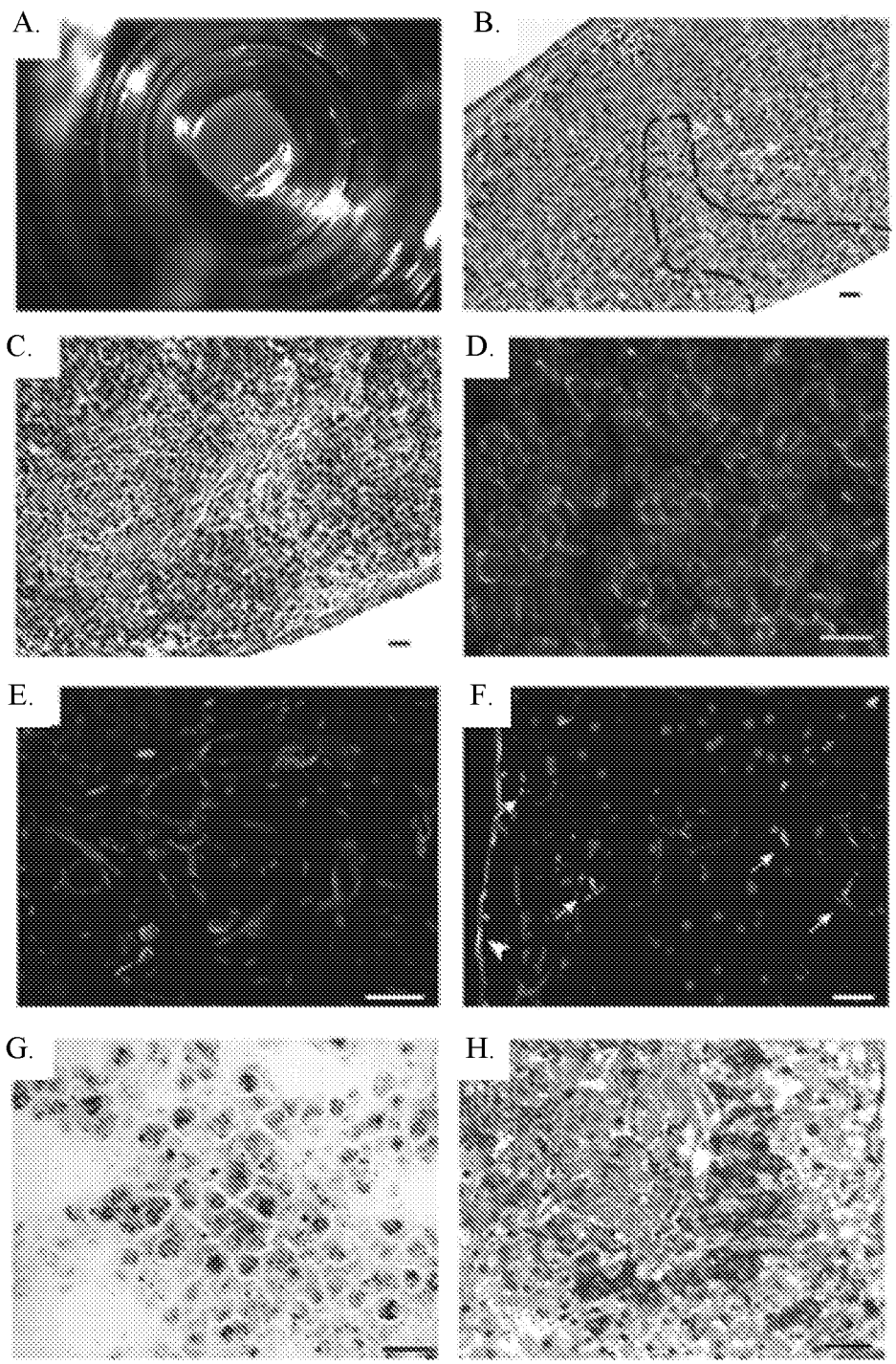
FIG. 20 is an image (A) and histological characterizations ((B)-(H)) of a non-limiting example of a three-dimensional, engineered, bioprinted liver tissue construct for use with liver disorder modeling. (A) shows a macroscopic image of a 3D liver tissue housed in a 24 well transwell. (B) shows H&E staining of a tissue cross-section with compartmentalization between the parenchymal and non-parenchymal fractions indicated by the dashed line. (C) shows extracellular matrix deposition assessed by Masson's trichrome staining. (D) shows immunohistochemical (IHC) staining of the parenchymal compartment for E-cadherin and Albumin. (E) shows IHC staining for CD31 and desmin to assess organization of the endothelial cells and the presence of quiescent hepatic stellates in the non-parenchymal compartment. (F) shows IHC staining for desmin and α-SMA to assess stellate cell activation. White arrows indicate quiescent stellates in the tissue interior that stain positive for desmin and negative for α-SMA. Cells at the tissue periphery stain positive for α-SMA (white arrowhead). (G) shows Oil-red O staining of 3D liver tissue cryosections to measure lipid storage. (H) shows periodic acid-Schiff (PAS) staining to identify glycogen granules. DAPI was utilized to stain the nuclei of the cells in all of the IHC staining samples. Scale bars in the lower right hand corner of images are 25 μm (B-D, G-H) or 50 μm (E, F).

Histologic analyses conducted throughout the maturation and maintenance period show that the bioprinted tissues retained the compartmentalization of parenchymal and non-parenchymal components established at the time of fabrication, and that the tissues condense and remodel over time, yielding stable 3D structures with a minimal thickness of 250 μm in the Z axis, dense tissue-like cellularity, and no evidence of necrosis (FIG. 20B). Masson's trichrome staining of the 3D bioprinted liver tissues revealed defined areas of collagen deposition in the non-parenchymal regions of the tissues, consistent with published evidence that functional endothelial cells produce and secrete extracellular matrix (ECM) during vasculogenesis (FIG. 20C). This ECM allows for the formation of a cohesive tissue unit without the use of exogenous scaffolding materials. Immunofluorescent analyses of the tissues showed robust surface expression of the intercellular junctional protein E-cadherin as well as cytoplasm-localized human albumin in the hepatocytes of the parenchymal compartment (FIG. 20D). Over time in culture, the endothelial cells form extensive networks, with evidence of lumens by day 21 (FIG. 20E). While human and rodent HSCs maintained in standard monolayer culture on plastic undergo activation to a myofibroblast phenotype with concomitant upregulation of smooth muscle actin (α-SMA), the HSC resident in the interior of the 3D liver tissues express desmin and not α-SMA (FIGS. 20E and 20F), suggesting that they are capable of establishing and maintaining a quiescent state within the 3D multicellular environment. A subpopulation of activated stellate cells, identified by their expression of α-SMA, can be identified at the tissue/media interface (FIG. 20F). Lipid storage and glycogen storage, two functions associated with hepatocytes in vivo, were also demonstrated in the bioprinted liver tissues after maturation (FIGS. 20G and 20H, respectively).

Example 7

Bioprinted Liver Tissue For Modeling of NAFLD (Steatosis)

The bioprinted liver tissue construct of Example 6 was treated with nutrient-mediated accumulation to induce a steatosis phenotype. Specifically, to induce steatosis, a first liver tissue construct was treated with palmitic acid (PA) of varying concentrations (200 uM PA or 500 uM PA) daily for 3 weeks in the presence of high glucose media (DMEM-HG). A second liver tissue construct was treated with a 5% and 10% lipid mix of oleic acid (OC) to palmitic acid (PA) at a ratio of 2:1 daily for 3 weeks in the presence of high glucose media (DMEM-HG). Optionally, insulin or genipin (1 uM or 5 uM) can be used to stimulate fatty acid uptake into hepatocytes and enhance the fatty phenotype. Untreated liver tissue constructs maintained in high glucose media (DMEM-HG) were used as controls.

The technical challenge is to make a 3D, bioprinted liver tissue construct having the disorder without adversely affecting hepatocyte function or tissue health (albumin, LOH activity, ALT), which most closely recapitulates the benign nature of steatosis commonly observed in clinical steatosis. Tissue health were assessed at 7 day intervals using biochemical assays that measure hepatocellular function (i.e., albumin) and injury (i.e., LOH and ALT) with n≥5 per treatment group. Greater than 5% fatty infiltrate into hepatocytes is considered steatotic; therefore, morphometric and biochemical assays were conducted to quantify hepatic lipid content. Tissue morphology and extracellular matrix (ECM) deposition were assessed using H&E and Trichrome staining, respectively, at 7 day intervals.

Results

Figure 21:
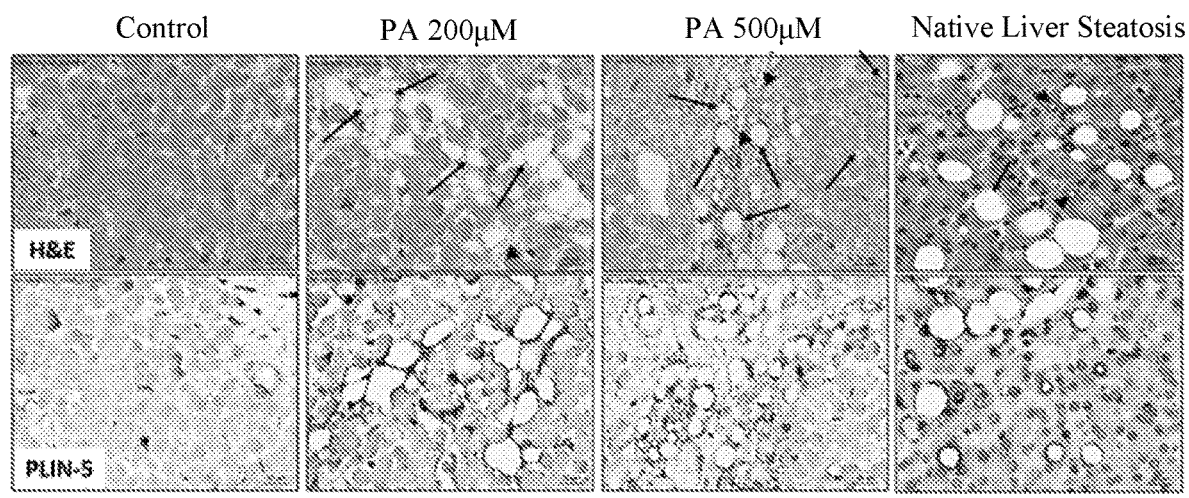
FIG. 21 is a histological characterization (hematoxylin and eosin (H&E) staining, top row; perilipin-5 (PLIN-5) staining, bottom row) of a non-limiting example of a three-dimensional, engineered, bioprinted liver tissue construct induced to exhibit a liver disorder known as steatosis upon treatment with palmitic acid (PA) at the noted concentrations as compared to an untreated control construct and a native human liver tissue exhibiting steatosis.

FIG. 21 shows that palmitic acid treatment for 21 days induces a steatotic phenotype, as evidenced by increased incidence and size of lipid droplets (micro- and macrovesicular) and positive lipid droplet marker staining (PLIN 5) when compared to untreated controls. Increased lipid accumulation after 21 days of PA treatment was confirmed via Oil Red O (ORO) staining and exhibited a significant dose-dependent increase. In FIG. 21, the top panel shows hematoxylin & eosin (H&E) staining, the bottom panel shows Perilipin-5 (PLIN-5) staining in brown following 21 days of treatment with 200 µM and 500 µM palmitic acid (PA). Untreated tissues at day 21 were used as controls. Native liver steatosis included for reference. Arrows indicate putative macrovesicular steatosis, arrowheads indicate putative microvesicular steatosis.

Figure 22:
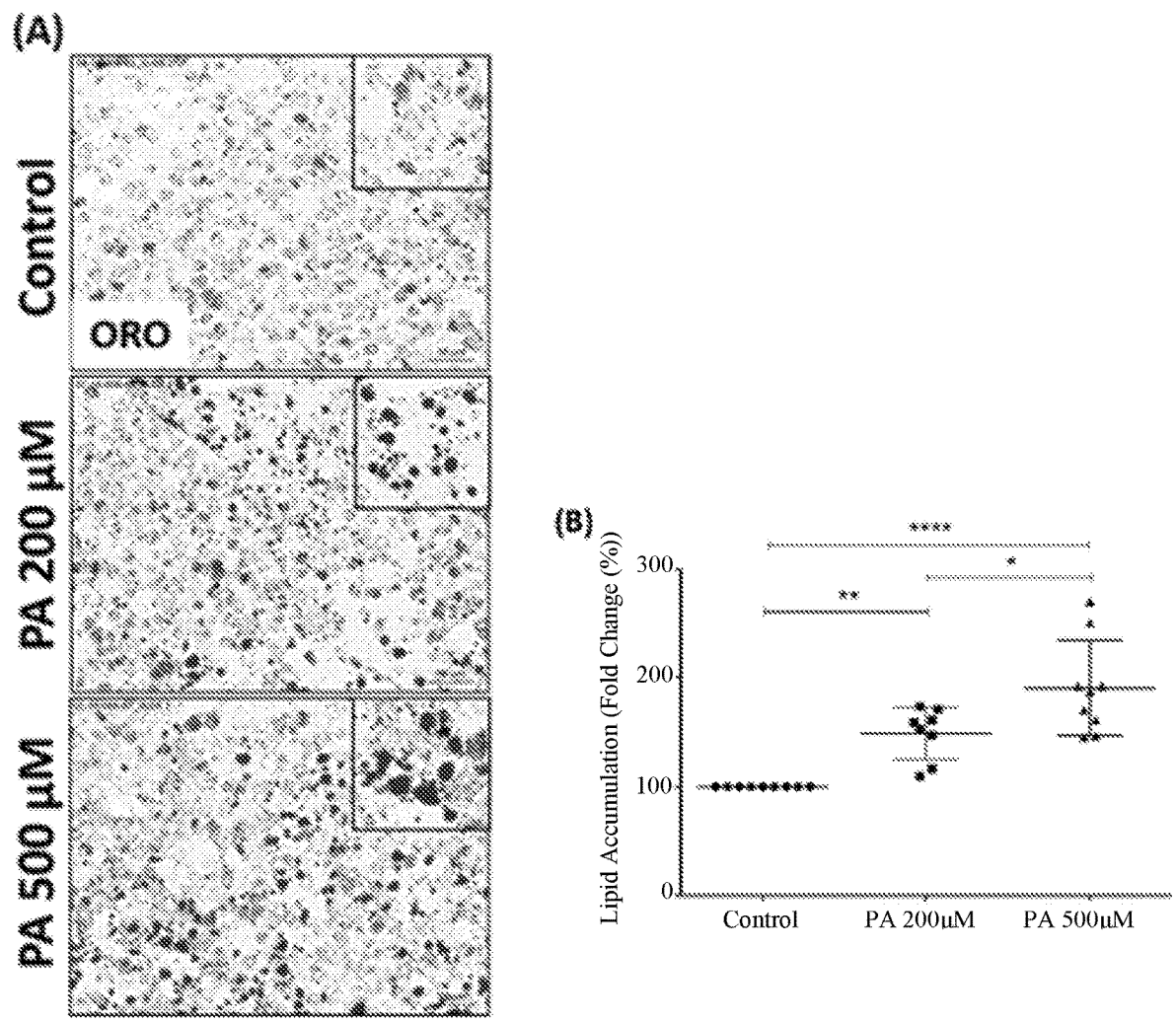
FIG. 22 is a histological characterization (A) and lipid accumulation characterization (B) of a non-limiting example of a three-dimensional, engineered, bioprinted tissue construct induced to exhibit a liver disorder known as steatosis. (A) shows Oil Red O (ORO) staining for untreated liver tissue constructs or constructs treated with the indicated amount of PA. (B) shows a graph the fold change of lipid accumulation in liver tissue constructs without treatment (control) or with the indicated treatments. *=$p<0.05$; =$p<0.01$; **=$p<0.0001$ as determined via one-way ANOVA with Turkey's multiple comparison test.

Additionally, in FIG. 22, after 21 days of palmitic acid treatments, the 3D bioprinted liver tissue construct was stained for lipid content using (a) ORO and (b) fold induction of lipid accumulation, quantified via morphometric analysis using ImageJ. Untreated tissues at day 21 were used as controls. FIG. 22 demonstrates increased lipid accumulation which was confirmed via Oil Red O (ORO) staining in 3D bioprinted liver tissue construct treated with palmitic acid for 21 days. Morphometric quantification of the ORO stain revealed a significant dose-dependent increase in lipid accumulation in palmitic acid treated tissues vs. controls.

The results depicted in FIGS. 21-22 are significant because NAFLD comprises of a spectrum of diseases initially characterized by lipid accumulation in the liver (steatosis). The proposed pathogenesis of NASH follows a 2-hit hypothesis. The first hit is steatosis in individuals who consume little or no alcohol, and are absent of viral hepatitis. The results in FIGS. 21-22 demonstrate that we can model steatosis, the "first hit" in the pathogenesis of NASH using 3d bioprinted liver tissue constructs, which is highly comparable to the clinical histopathology of steatosis used as a reference in FIG. 21.

Example 8

Bioprinted Liver Tissue for Modeling of NAFLD (NASH)

Kupffer cells (KCs) were added to the parenchymal region in the bioprinted liver tissue construct of Example 6. KCs are resident liver macrophage cells and are activated by a number of conditions, including hepatocellular injury and endotoxin (lipopolysaccharide, LPS) exposure from the gut through increased intestinal permeability and portal blood flow. Once activated, KCs secrete inflammatory cytokines that contribute to paracrine activation of injury and apoptotic signaling pathways in hepatocytes.

Separate high density bioinks comprising parenchymal cells (100% cellular paste, generated via compaction having human hepatocyte cells and human Kupffer cells) or non-parenchymal cells (150e6 cells/mL of endothelial cells and hepatic stellate cells formulated in hydrogel) were prepared and loaded into separate heads of the NovoGen Bioprinter™ Instrument within a standard biosafety cabinet. A computer script was then executed to deposit the bioinks in a two-compartment planar geometry (2 mm²×0.5 mm) onto the membranes of standard 24-well 0.4 µm transwell culture inserts (Corning, Tewksbury, MA USA) via continuous deposition microextrusion with the non-parenchymal cells comprising the border regions of each compartment and the parenchymal cells filling each compartment.

Here, the liver tissue construct having KCs was treated with 100 µg/ml of LPS and 500 uM palmitic acid daily for 21 days. LPS was used to activate the KCs in order to initiate inflammation. In turn, activated KCs release factors that activate hepatic stellate cells, which initiate fibrosis. Optionally, the liver tissue construct can be treated with IL-1β to stimulate KC activation. Untreated tissues with and without KCs were used as controls.

Tissue health were assessed at 7 day intervals using biochemical assays on spent media that measure hepatocellular function as outlined in Aim 1 (n≥5/group). Histological endpoints used to assess tissue morphology and composition (H&E, CD31, Desmin, E-cadherin, Albumin), ECM deposition (trichrome), hepatic stellate cell activation (desmin, a-smooth muscle actin ratio), lipid vacuoles (perilipin) and lipid content (Oil red 0) were measured at weekly intervals. In order to determine baseline cytokine production in response to lipid treatment, inflammatory cytokine release were measured at 7 day intervals via chemiluminescence with the V-Plex Pro-Inflammatory Panel (Meso Scale Discovery, Rockville, MD), which measures TNF-α, IL-113, IL-6, IL-8, IL-4, IL-2, IL-13, IL-12p70, IL-10, and interferon-y (IFN-y).

Results

Figure 23:
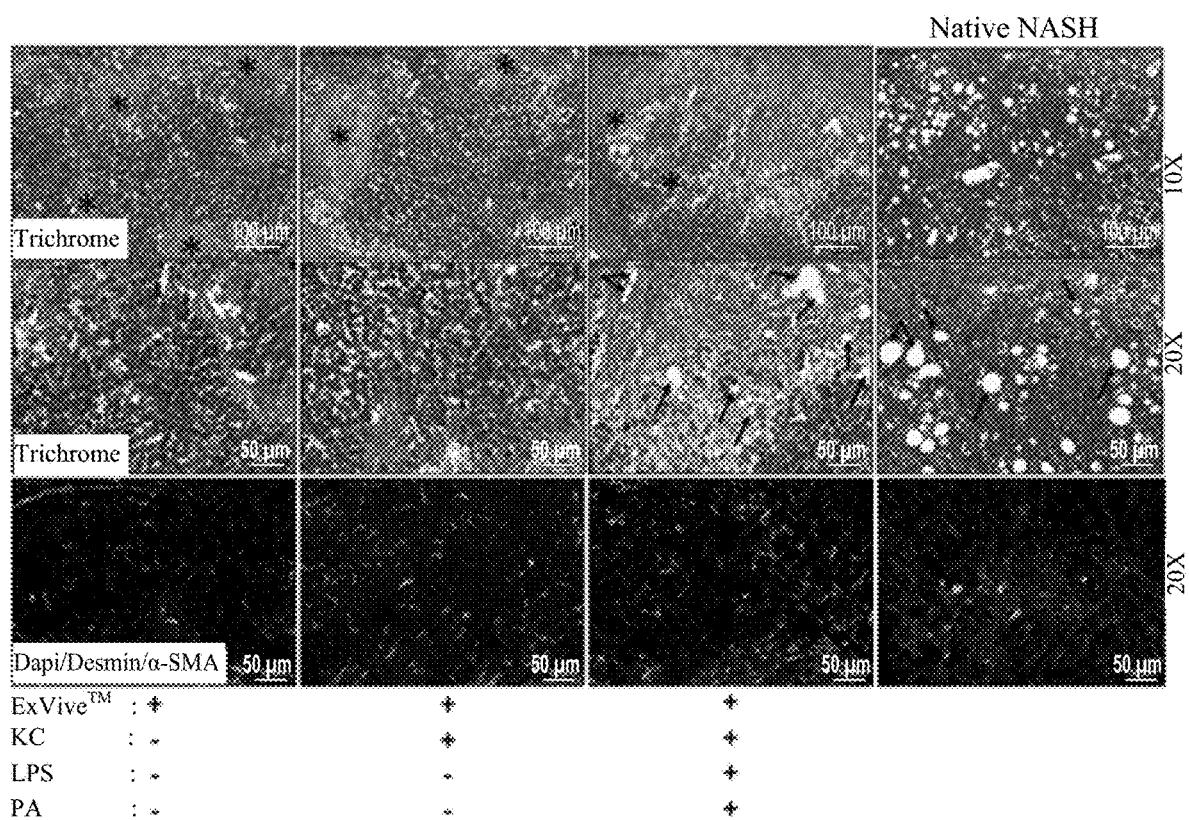
FIG. 23 is a histological characterization (trichrome staining, top two rows; DAPI, desmin, α-SMA staining, bottom row) of a non-limiting example of a three-dimensional, engineered, bioprinted liver tissue construct induced to exhibit a liver disorder known as NASH. KC=Kupffer cells; LPS=lipopolysaccharide; Native NASH=native human liver tissue exhibiting NASH.

FIG. 23 shows increased extracellular matrix (ECM) deposition in untreated immune competent (+KCs) 3D bioprinted liver tissue construct via trichrome staining (blue), and increased proliferation of HSCs (Desmin; green) when compared to controls (−KCs) after 24 days in culture. Furthermore, immune competent 3D bioprinted liver tissue construct treated simultaneously with 500 µM palmitic acid and 100 µg/mL LPS for 21 days displayed dramatically increased fibrosis (assessed by trichrome stain), increased HSC activation (α-SMA; red), increased steatosis (greater incidence of lipid droplets; arrows) vs. untreated controls (+/−KCs). Furthermore, immune competent 3D bioprinted liver tissue construct treated simultaneously with 500 µM palmitic acid and 100 µg/mL LPS for 21 days displayed dramatically increased fibrosis (assessed by trichrome stain), increased HSC activation (α-SMA; red), increased steatosis (greater incidence of lipid droplets; arrows) vs. untreated controls (+/−KCs). Untreated tissues with and without Kupffer cells (KCs) at day 21 were used as controls. In FIG. 23, * denotes NPCs compartments and arrows indicate putative macrovesicular steatosis.

Figure 24:
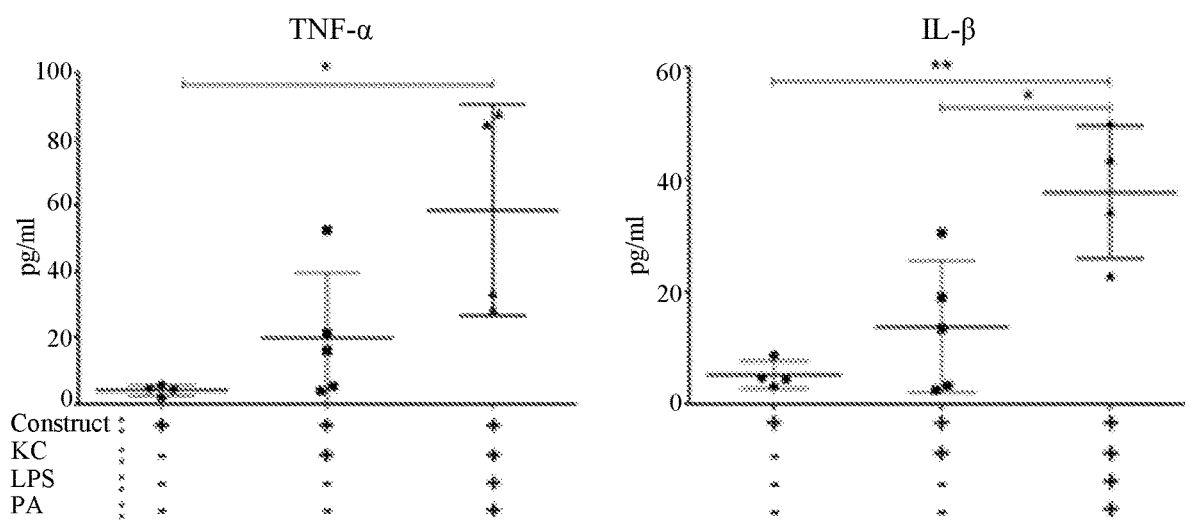
FIG. 24 is an inflammatory cytokine response characterization of a non-limiting example of a three-dimensional, engineered, bioprinted liver tissue construct induced to exhibit a liver disorder known as NASH. (A) shows a graph indicating TNF-α release. (B) shows a graph indicating IL-1β release. In (A) and (B), *=$p<0.05$; **=$p<0.01$.

Also, FIG. 24 shows inflammatory cytokine response in the 3D bioprinted liver tissue construct with Kupffer cells treated with palmitic acid (PA) and lipopolysaccharide (LPS). In FIG. 24, shown are secreted TNF-α levels (top panel) and IL-1β levels (bottom panel) following 21 days treatment with both 500 uM PA and 100 ug/mL LPS. Cytokine levels in untreated tissues with and without Kupffer cells are day 21 were used as controls. In sum, FIG. 24 demonstrates significantly increased secretion of inflammatory cytokines (TNFα and IL1β) from immune competent 3D bioprinted liver tissue construct treated simultaneous with 500 uM palmitic acid and 100 ug/mL LPS for 21 days vs. untreated controls (+/−KCs).

FIGS. 23-24 is significant because they show that following the "first hit," steatosis, the "second hit" in the pathogenesis of NASH involves increased inflammation, hepatocellular injury, and often increased fibrosis. Using immune competent (+KCs) 3D bioprinted liver tissue construct, we have demonstrated increased steatosis (1st hit) along with increased inflammation and fibrosis (2nd hit) vs. controls.

Example 9

Bioprinted Liver Tissue For Modeling of NAFLD (Steatosis)

Figure 25:
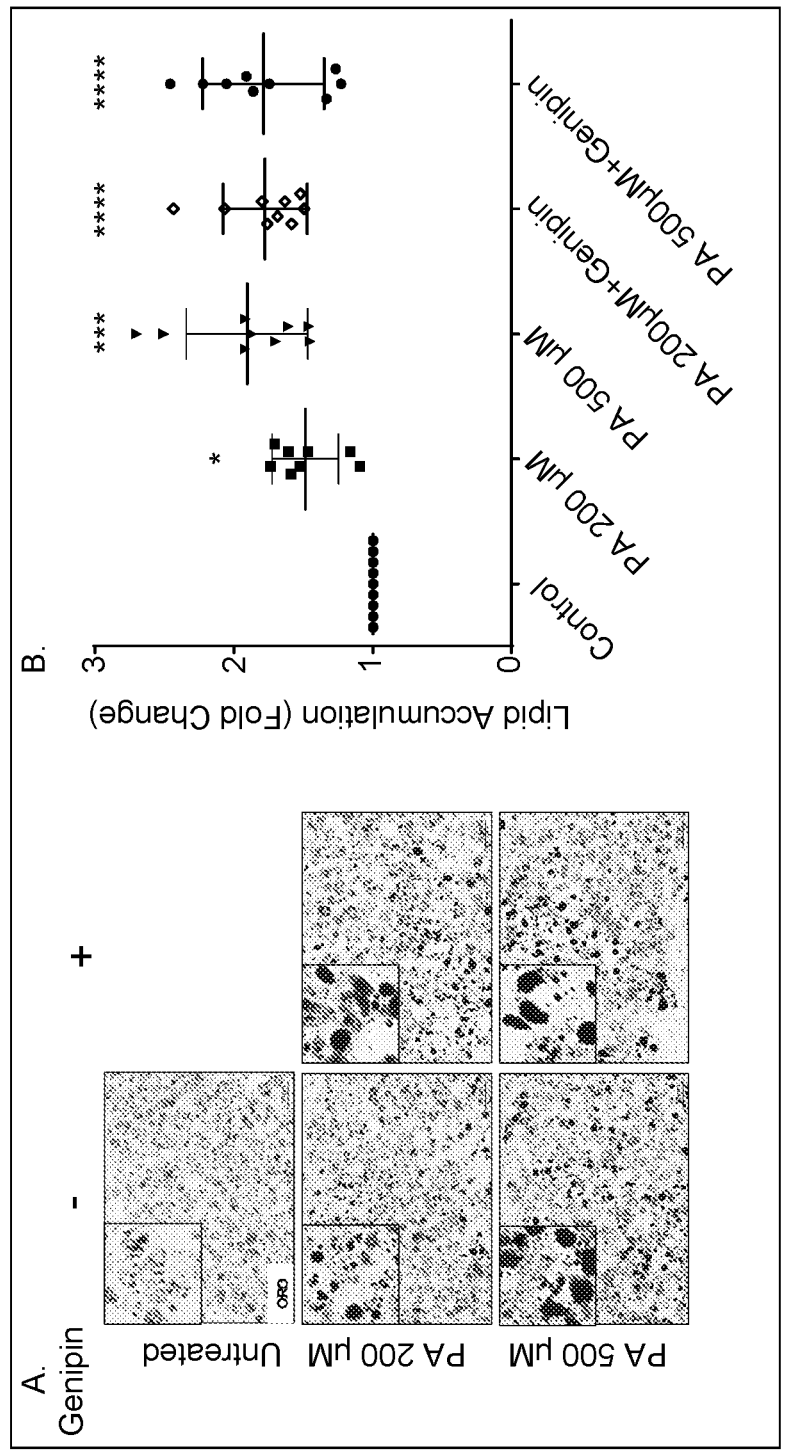
FIG. 25 depicts histological characterizations (A) and lipid accumulation characterizations (B) of non-limiting examples of three-dimensional, engineered, bioprinted liver tissue constructs induced to exhibit NAFLD (steatosis). (A) shows ORO staining for untreated liver tissue constructs or constructs treated with the indicated amount of PA. (B) shows a graph the fold change of lipid accumulation in liver tissue constructs without treatment (control) or with the indicated treatments. *=$p<0.05$; *=$p<0.001$; **=$p<0.0001$ as determined via two-way ANOVA in comparison to control.

Bioprinted liver tissue constructs were treated to induce a NAFLD phenotype, and for this experiment, the NAFLD phenotype was a steatosis phenotype. In FIG. 25(A), bioprinted liver tissue constructs were treated with either: (1) 200 µM Palmitic Acid (PA), (2) 500 µM PA, (3) 200 µM PA and 5 µM Genipin, or (4) 500 µM PA and 5 µM Genipin. After 21 days of such treatment, these bioprinted liver tissue constructs were quantified for lipid accumulation by staining using Oil Red O (ORO) and morphometric analysis using Image J, as depicted in FIG. 25(A). An untreated bioprinted liver tissue construct served as the control. Experiments involving induction of NASH in bioprinted tissues in this and the following Examples included glucose in the basal media for both control and treated tissues. Experiments in this and the following Examples utilized bioprinted liver tissue constructs produced according to Examples 6 or 8.

Significantly, as shown in FIG. 25(B) by the lipid accumulation fold change, a NAFLD phenotype (steatosis) was successfully induced in these bioprinted liver tissue constructs using PA and Genipin. Also, FIG. 25(B) shows that 500 µM PA lead to greater accumulation of lipid droplets than 200 µM PA. Addition of Genipin did not further increase lipid accumulation over 500 µM PA alone.

Example 10

Bioprinted Liver Tissue For Modeling of NAFLD (NASH)

Figure 26:
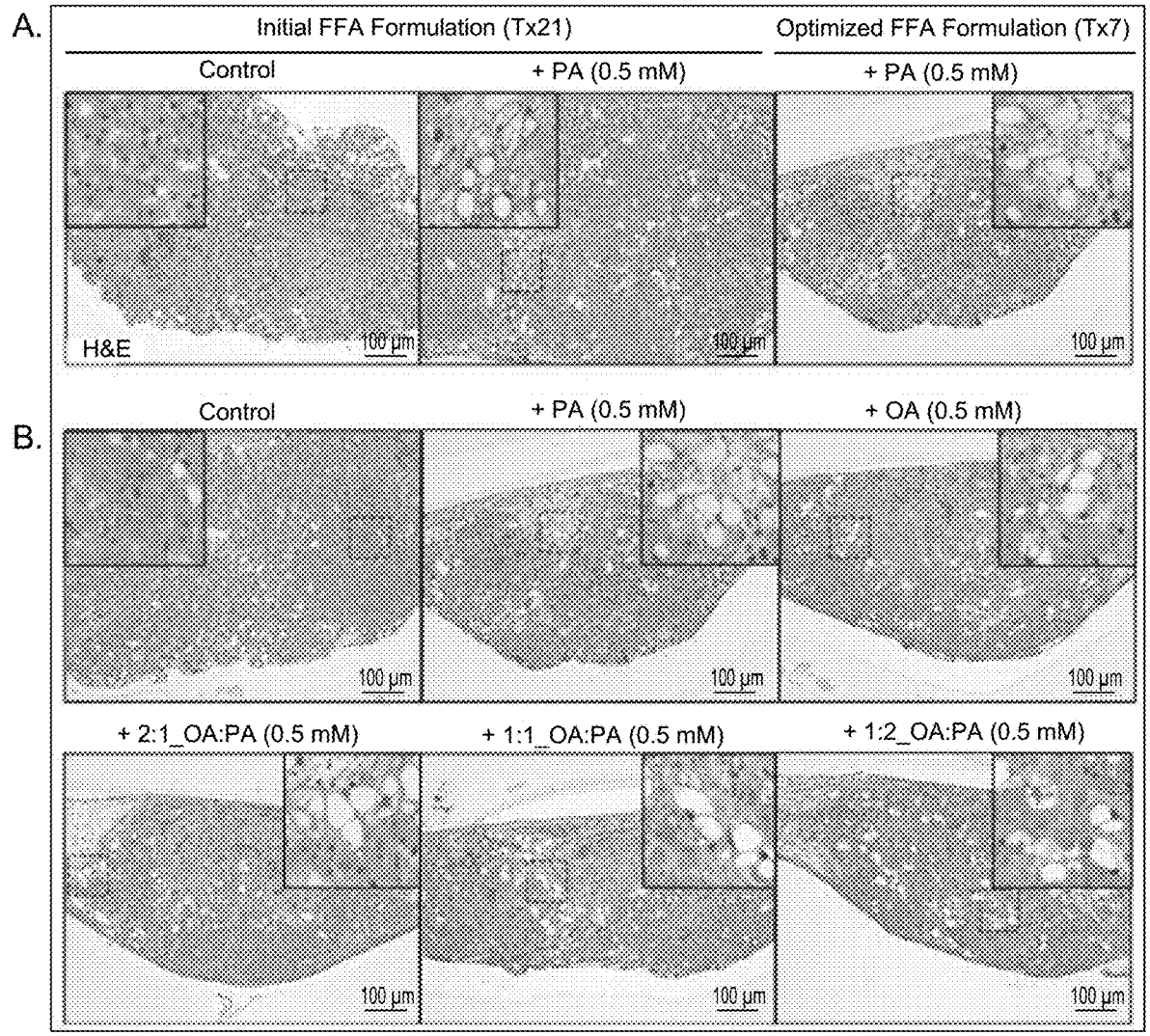
FIG. 26 depicts histological characterizations (H&E staining) of non-limiting examples of three-dimensional, engineered, bioprinted liver tissue constructs induced to exhibit a NAFLD (steatosis) phenotype. (A) shows treatment with PA in either an Initial Free Fatty Acid (FFA) Formulation (Tx21) (10 mM PA in 1% bovine serum albumin (BSA)) or in an Optimized FFA Formulation (Tx7) (5 mM PA in 10% BSA). The control received the initial FFA formulation without PA. Treatment in the optimized formulation resulted in onset of steatosis at 7 days versus 21 days for the initial formulation. (B) shows treatment of tissues with the noted concentrations of PA and/or OA in the optimized FFA formulation versus a control receiving the optimized FFA formulation without PA or OA. Treatments resulted in an increased degree of lipid droplet incidence and sizes. OA=oleic acid

Bioprinted liver tissue constructs were treated to induce a NASH phenotype. As shown in FIG. 26(A), treatment with PA in an optimized formulation of FFA (5 mM PA in 10% Bovine serum albumin (BSA)) versus an initial formulation of FFA (10 mM PA in 1% BSA) lead to earlier onset and increased incidence of steatotic phenotypes (Day 7 rather than Day 21, respectively). FIG. 26(B) shows bioprinted liver tissue constructs that were treated with PA and/or OA in the optimized formulation of FFA: (1) 0.5 mM PA, (2) 0.5 mM Oleic Acid (OA), (3) 2:1 OA:PA (0.5 mM), meaning 2 parts OA to 1 part PA (i.e. a ratio of 2:1), (4) 1:1 OA:PA (0.5 mM), or (5) 1:2 OA:PA (0.5 mM), meaning 1 part OA to 2 parts PA (i.e. a ratio of 1:2). All induction approaches lead to steatotic outcomes. Untreated bioprinted liver tissue constructs were used as controls.

Figure 27:
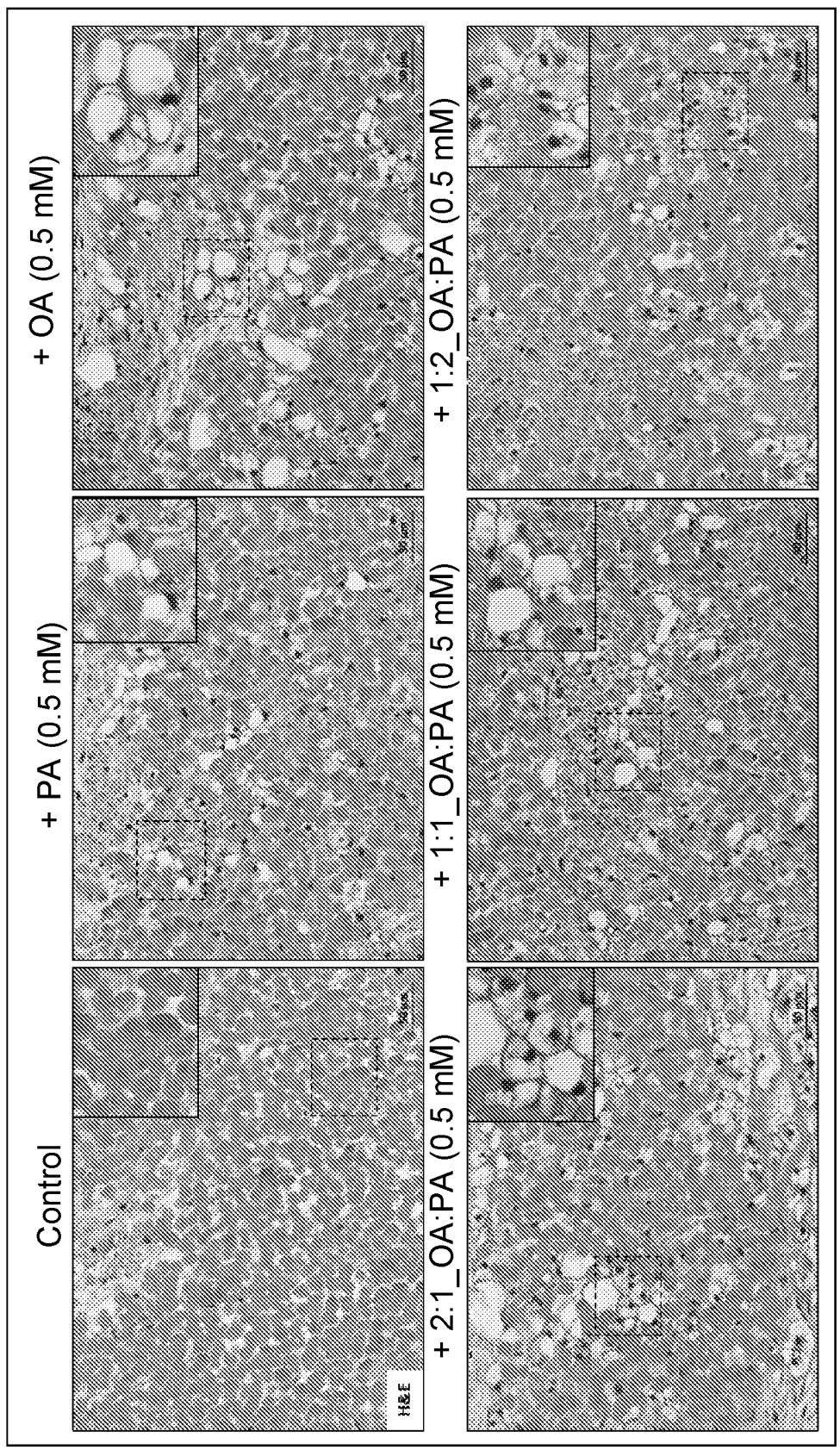
FIG. 27 depicts histological characterizations (H&E staining) of non-limiting examples of three-dimensional, engineered, bioprinted liver tissue constructs induced to exhibit a NAFLD (steatosis) phenotype by noted concentrations of OA and PA as compared to untreated tissues (Control).
Figure 28:
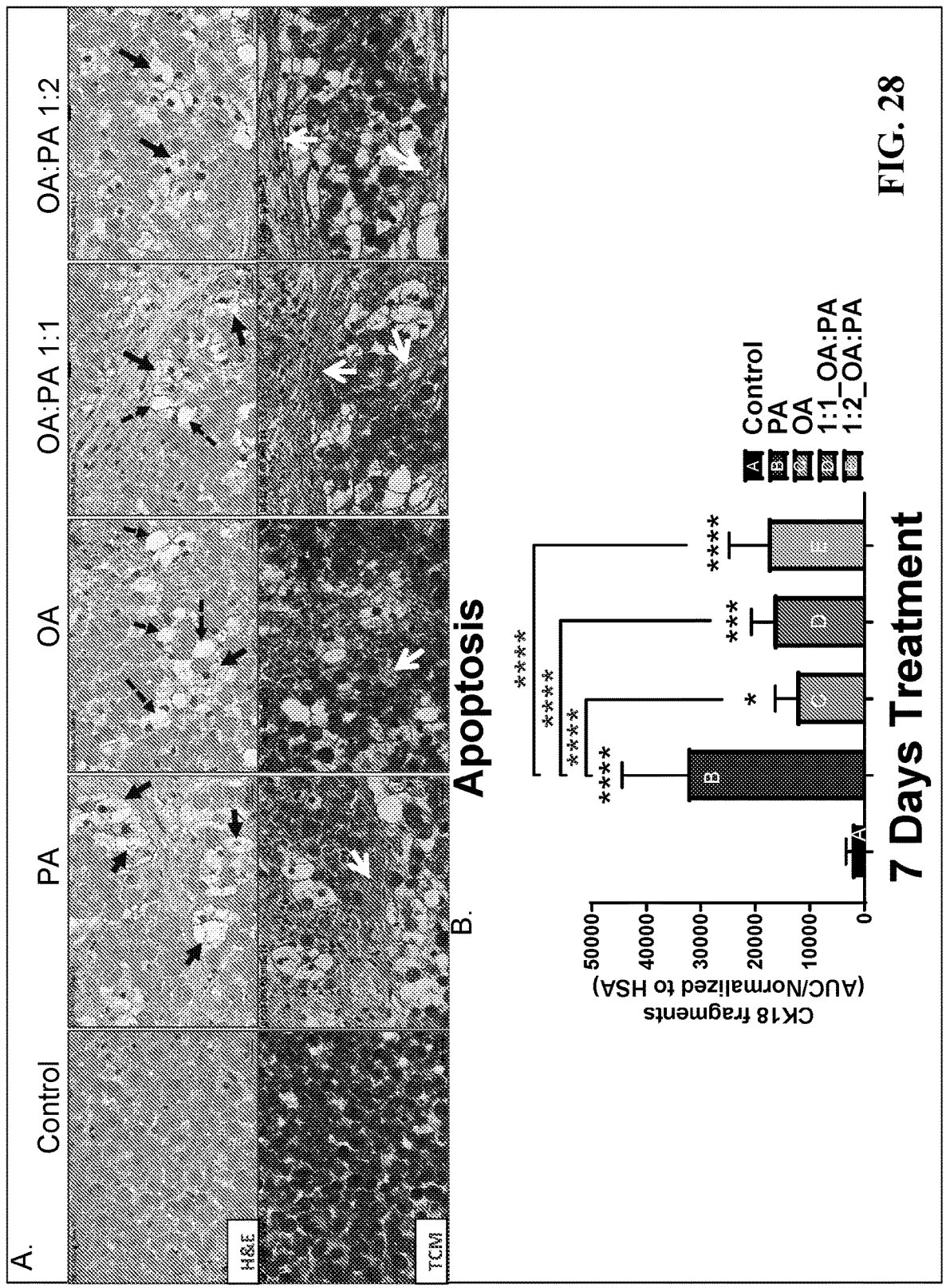
FIG. 28 depicts histological characterizations (A) and CK18 quantifications (B) of non-limiting example of three-dimensional, engineered, bioprinted liver tissue constructs induced to exhibit a NASH phenotype. (A) shows H&E (top row) and TCM staining of liver tissue constructs that were untreated (Control) or treated with OA and/or PA as indicated. Dashed black arrows=macrovesicular steatosis; black arrows=putative ballooned hepatocytes; white arrows=fibrosis. (B) shows a bar graph indicating apoptosis in terms of cytokeratin 18 (CK18) fragments. AUC=area under curve; HSA=human serum albumin. For comparisons to control, *=p<0.05; *=p<0.001; =p<0.0001. For comparisons to PA treatment, **=p<0.0001.

Also significant in FIG. 27, following 14 days of palmitic acid (PA), oleic acid (OA), and various combinations of OA:PA in different ratios, increased lipid droplet (LD) incidence was seen in all free fatty acid (FFA) treated groups with larger sizes of LD's observed in OA and OA:PA 2:1 treatments. As shown in FIG. 28(A), following 7 days of treatment of 1 mM PA, OA, 1:1 OA:PA, and 1:2 OA:PA, respectively, PA treatment displayed increased incidence of putative ballooned hepatocytes (see top row of FIG. 28: all arrows for PA and 1:2 OA:PA, bottommost arrow for OA, and rightmost arrow for 1:1 OA:PA) and fibrosis (see bottom row of FIG. 28, all arrows) versus OA treatment displayed increased incidence of macrovesicular steatosis (see top row of FIG. 28: all arrows for OA except the bottommost arrow, and both leftmost arrows for 1:1 OA:PA) and less fibrosis. PA treatment also exhibited significantly higher levels of caspase cleaved cytokine (CK) 18 fragments, a non-invasive measure of apoptosis when compared to all other FFA treatments and untreated controls. Thus, FIG. 28(B) shows that there was increased cytotoxicity with PA treatment.

Figure 29:
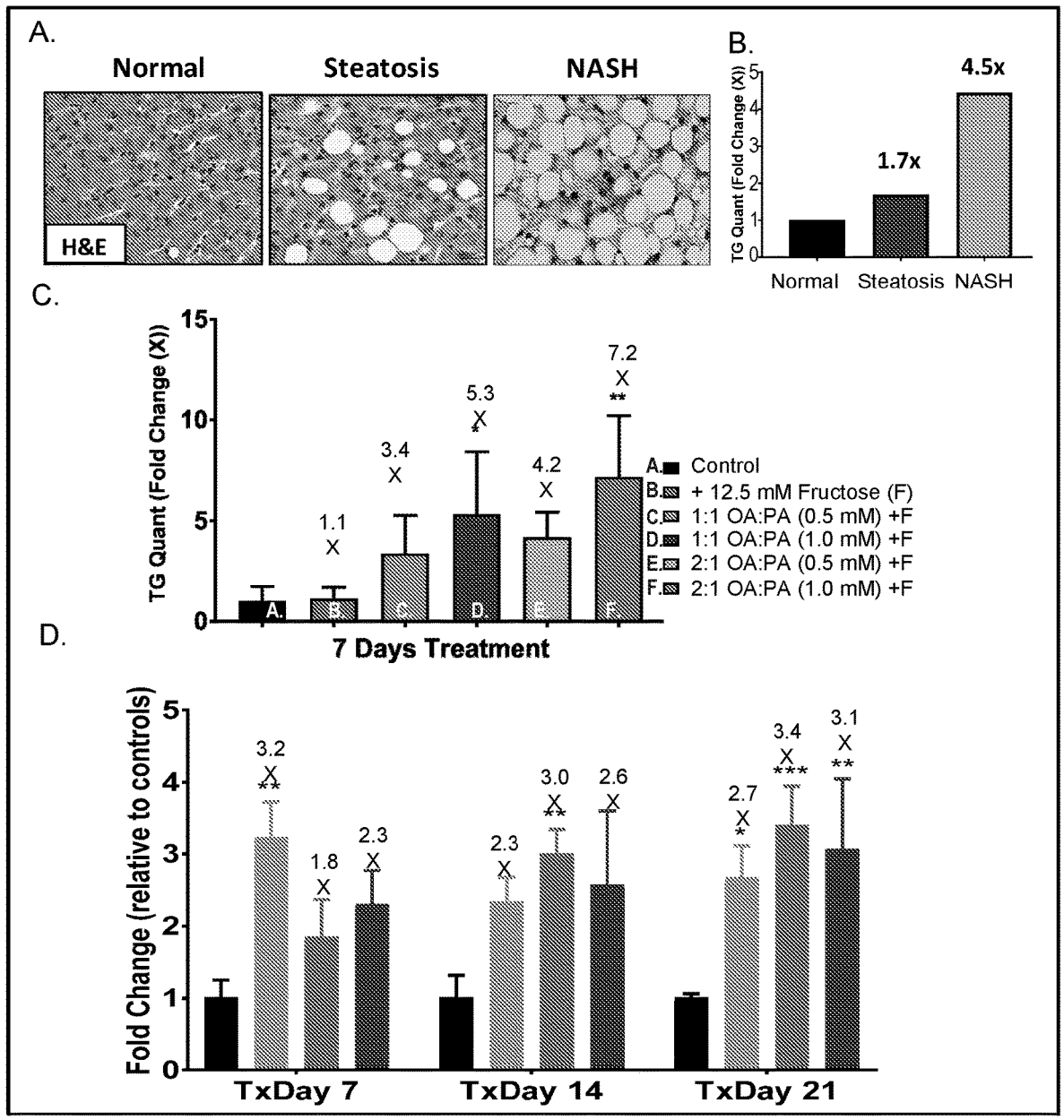
FIG. 29 depicts histological characterizations (A) and quantitative measurements ((B)-(D)) of triglyceride (TG) in human tissues and non-limiting examples of a three-dimensional, engineered, bioprinted liver tissue constructs induced to exhibit a NASH phenotype. (A) shows H&E staining of a native human tissue (Normal), a native human hepatic steatosis tissue (Steatosis), and a native human NASH tissue (NASH). (B) shows the fold change of TG in native human steatosis and NASH tissues as compared to normal tissue. (C) shows TG fold changes in liver tissue constructs after 7 days without treatment (Control) or treatment with the indicated amounts of fructose, OA, and PA. (D) shows TG fold changes in liver tissue constructs after treatment for 7, 14, or 21 days (TxDay 7, TxDay 14, or TxDay 21, respectively) without (Control) or with treatment with the indicated amounts of PA and OA. In (C), *=p<0.05 and **=p<0.001; in (D), *=p<0.05; =p<0.01; *=p<0.001.

FIG. 29 depicts triglyceride (TG) quantification in the bioprinted liver tissue constructs after FFA treatment. FIG. 29(B) shows that native human hepatic steatosis and NASH displayed a 1.7 and 4.5-fold increase in TG quantification when compared to normal livers respectively (n=1). FIG. 29(C) shows that after 7 days of treatment with fructose and a low or high dose of FFAs resulted in measurable, dose-dependent increases in lipid accumulation in bioprinted liver tissues. FIG. 29(D) shows significantly increased TG levels over time in bioprinted liver tissues prepared according to Example 8, following 7, 14, and 21 days of treatment with fructose and FFA, when compared to controls (n=3-4 per group).

Significantly, Example 10, as shown in FIGS. 26-29, demonstrates that a NASH phenotype comprising of at least lipid accumulation (steatosis), hepatocellular ballooning, macrovesicular steatosis, and fibrosis can be induced using FFA treatment, such as PA or OA, on the bioprinted liver tissue constructs.

Example 11

Bioprinted Liver Tissue for Modeling of NAFLD (NASH)

Figure 30:
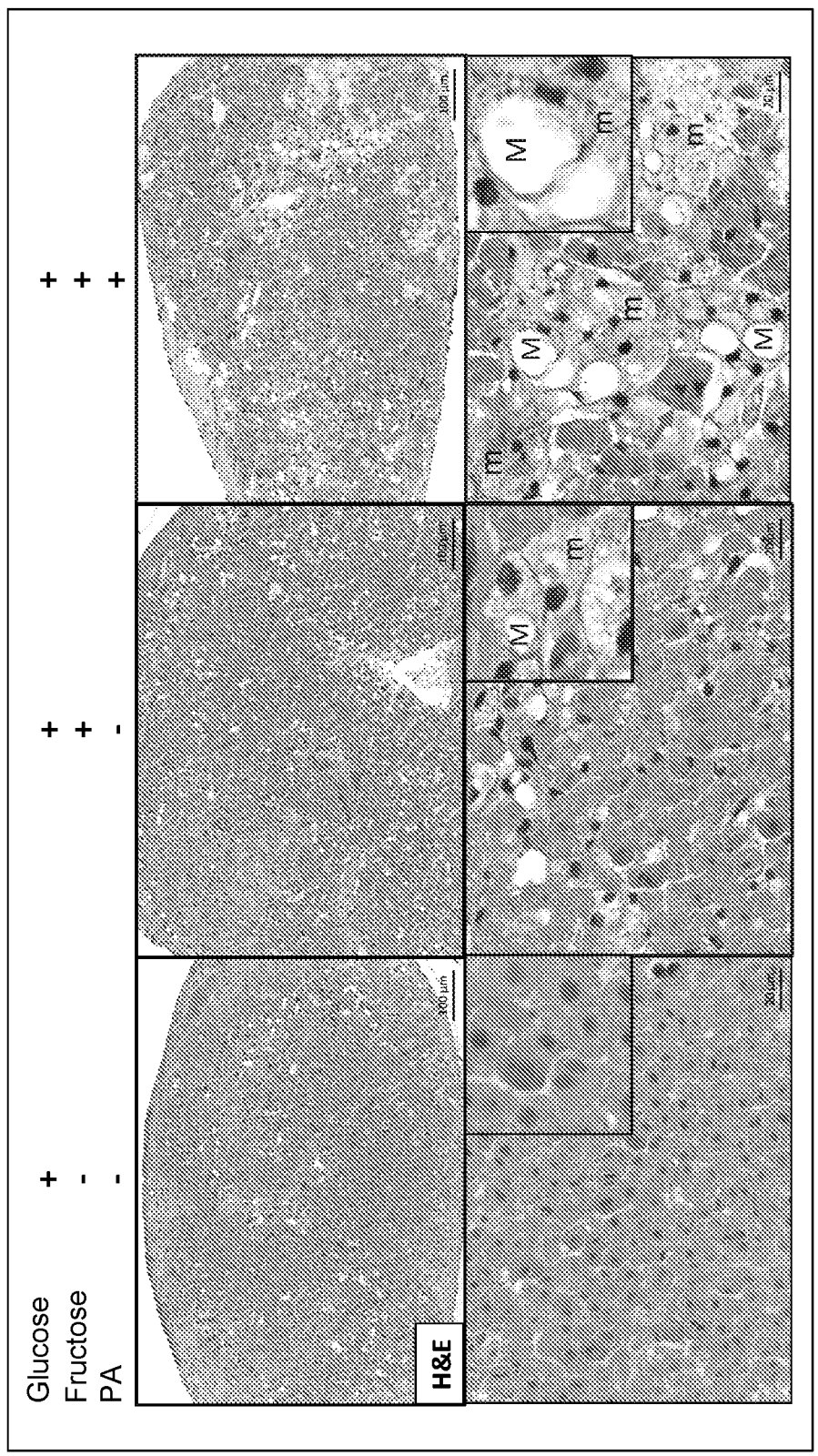
FIG. 30 depicts histological characterizations (H&E staining) of non-limiting examples of three-dimensional, engineered, bioprinted liver tissue constructs induced to exhibit a NAFLD (steatosis) phenotype in the presence of glucose, fructose, or PA. m and M=microvesicular and macrovesicular steatosis.

Bioprinted liver tissue constructs were treated with nutrient-mediated accumulation to induce a NASH phenotype. As depicted in FIG. 30, a first bioprinted liver tissue construct was treated with 21 days of combined glucose (12.5 mM) and fructose (12.5 mM), which displayed induction of microvesicular (m) steatosis. Additionally, a second bioprinted liver tissue construct was treated with 21 days of combined glucose (12.5 mM), fructose (12.5 mM), and 0.5 mM PA, which resulted in a greater induction of both micro (m) and macrovesicular (M) lipid droplet phenotypes with potential hepatocellular injury (see arrow in FIG. 30).

Figure 31:
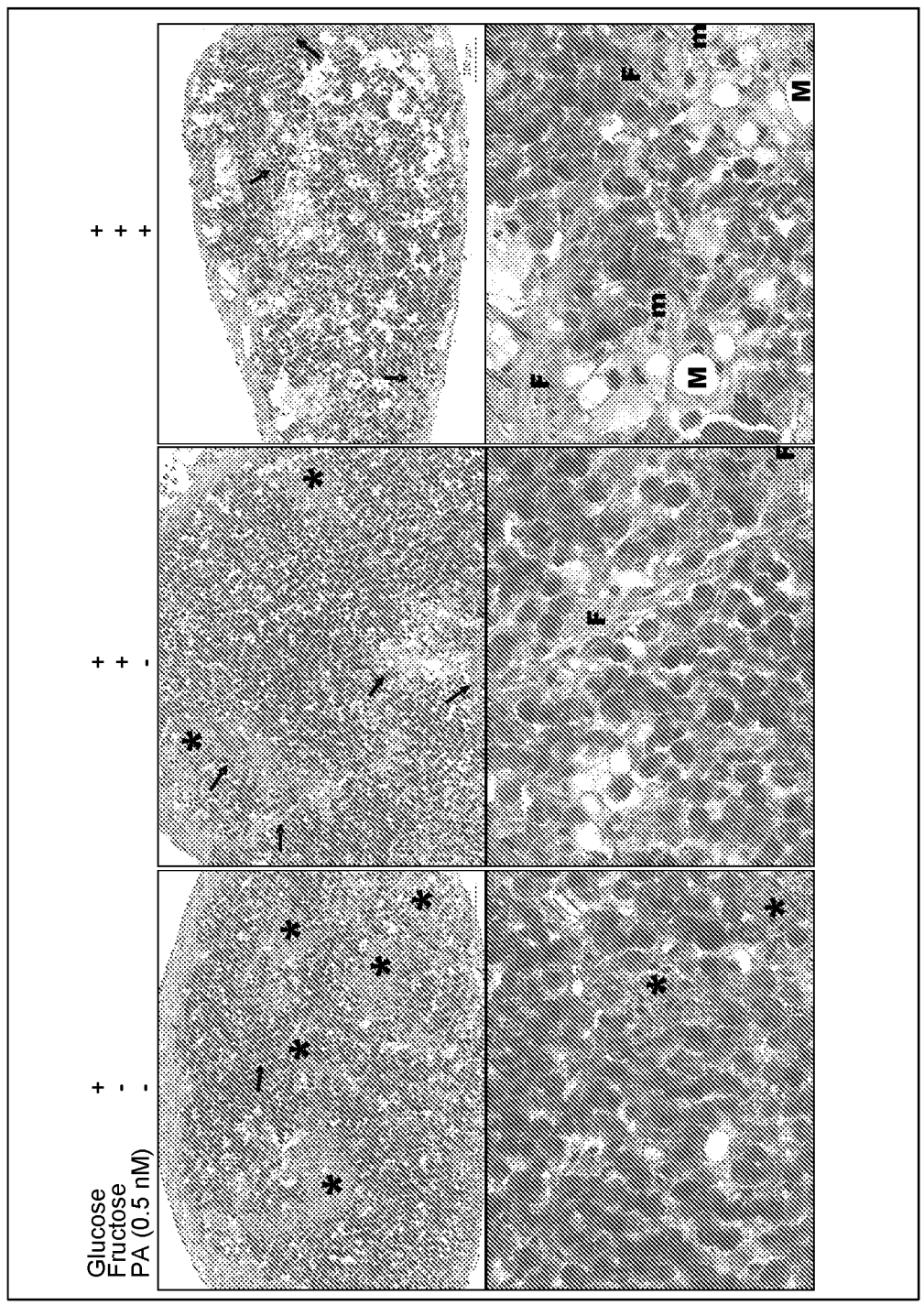
FIG. 31 depicts histological characterizations (TCM staining) of non-limiting examples of three-dimensional, engineered, bioprinted liver tissue constructs induced to exhibit a NASH phenotype. m and M are as defined in FIG. 30. *=non-parenchymal cell rich regions. Arrows indicate fibrosis.
Figure 32:
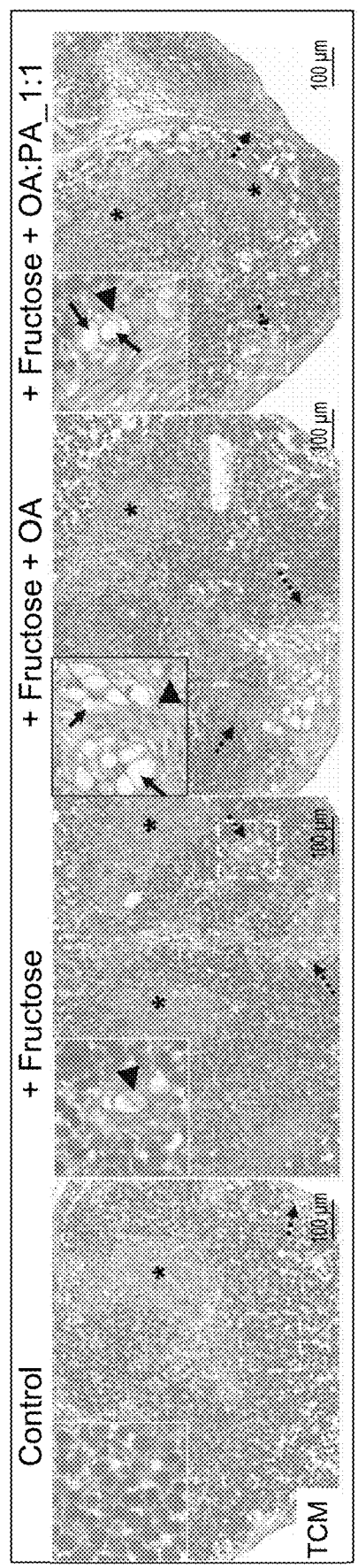
FIG. 32 depicts histological characterizations (TCM staining) of non-limiting examples of three-dimensional, engineered, bioprinted liver tissue constructs induced to exhibit a NASH phenotype. Dashed boxes indicate region of magnification displayed in upper left quadrant of images, showing induction of microvesicular steatosis (arrowheads) and macrovesicular steatosis (arrows) in treated constructs versus control. Arrows not included in the magnified regions highlight areas of collagen deposition and fibrosis.

As shown in FIGS. 31-32, fructose treatment induces fibrosis in the bioprinted liver tissue constructs. In FIG. 31, following 21 days of treatment either (1) fructose (12.5 mM), or (2) fructose (12.5 mM) with PA (0.5 mM), immune competent bioprinted liver tissue constructs displayed increased fibrosis (see arrows in FIG. 31) versus controls. The combination of fructose (12.5 mM) and PA (0.5 mM) induced increased micro (m) and macrovesicular (M) steatosis with fibrosis. In FIG. 31, * denotes non-parenchymal cells (NPC) rich regions. In FIG. 32, bioprinted liver tissue constructs were treated with 14 days of either: (1) fructose only (20 mM), (2) fructose and OA (0.5 mM), or (3) fructose and OA:PA 1:1 (0.5 mM). Significantly, following 14 days of such treatment, immune competent bioprinted liver tissue constructs displayed increased fibrosis (see arrows in FIG. 32) versus controls. Addition of sugars (i.e., fructose) and FFAs (i.e. PA, OA) appeared to induce microvesicular and macrovesicular steatosis, as depicted in the arrows in FIG. 32. In FIG. 32, * denotes NPC rich regions.

Figure 33:
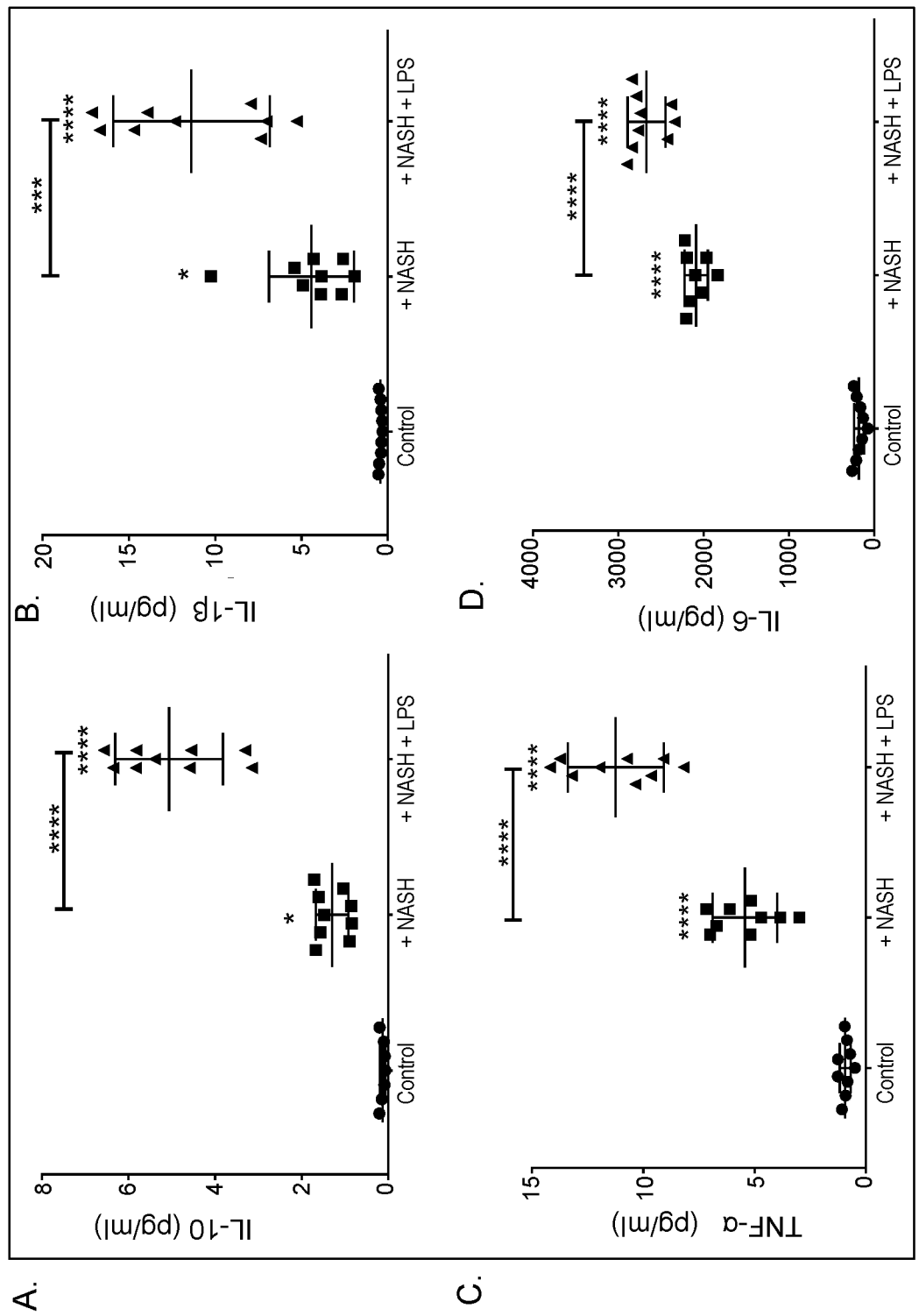
FIG. 33 depicts quantitative measurements of cytokine release (IL-10 in (A), IL-1β in (B), TNF-α in (C), and IL-6 in (D)) in non-limiting examples of three-dimensional, engineered, bioprinted liver tissue constructs induced to exhibit a NASH phenotype. Control=untreated liver tissue construct; +NASH=treatment to induce NASH; +NASH+LPS=treatment to induce NASH and co-treatment with lipopolysaccharide (LPS). *=p<0.05; *=p<0.001; and **=p<0.0001.

In FIG. 33, NASH induction results in increased inflammation in the bioprinted liver tissue constructs. Significantly, in FIG. 33, following 14 days of NASH induction using 500 µM PA and 12.5 mM fructose, the bioprinted liver tissue constructs exhibited increased levels of cytokines IL-10 (A), IL-1β (B), TNF-α (C), and IL-6 (D). The co-treatment of lipopolysaccharide (LPS) at 1 ug/mL with NASH induction resulted in cytokine levels that were significantly increased above NASH induction only. Untreated bioprinted liver tissue constructs were used as controls.

Figure 34:
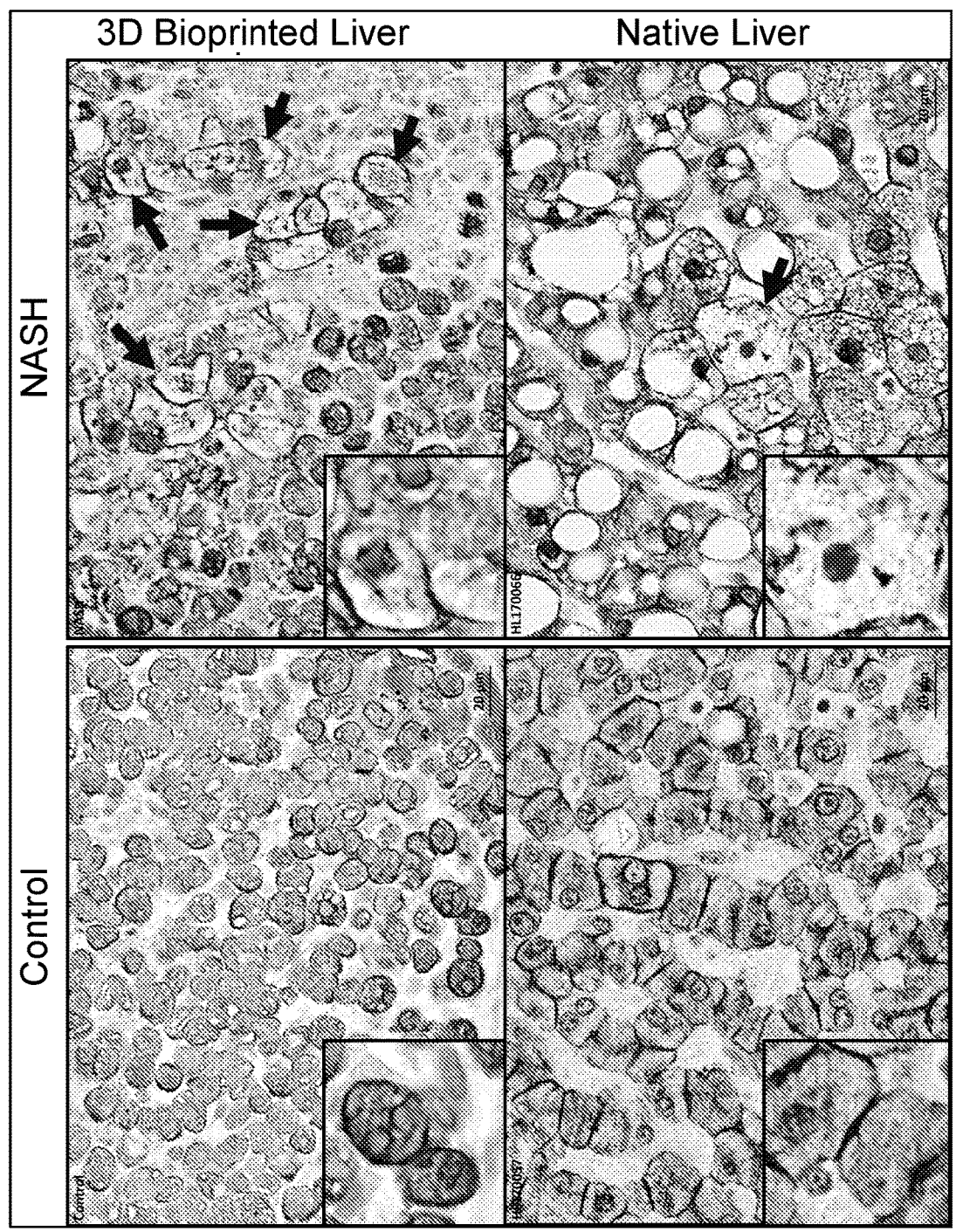
FIG. 34 depicts histological characterizations (CK18 staining) of non-limiting examples of three-dimensional, engineered, bioprinted liver tissue constructs induced to exhibit a NASH phenotype and native human liver tissue exhibiting NASH. Untreated liver tissue constructs and non-diseased human liver tissue are shown as controls. Arrows indicate incidence of larger hepatocytes displaying rarefied cytoplasm's with reduced CK18 staining.

In FIG. 34, NASH induction results in putative hepatocellular ballooning bioprinted liver tissue constructs. Hepatocellular ballooning was identified histologically by larger or swollen hepatocytes with reduced CK18 staining in native diseased livers (NASH, Native Liver) when compared to hepatocytes found in a non-diseased liver (Control, Native Liver). Following 21 days of fructose (12.5 mM) and PA (500 µM) treatment, an increased incidence of larger hepatocytes displaying rarefied cytoplasm with reduced CK18 staining was seen in bioprinted liver tissue constructs (see NASH, Bioprinted Liver) versus controls. Untreated bioprinted liver tissue constructs at day 21 were used as controls.

Significantly, Example 11, as shown in FIGS. 30-34, demonstrates that a NASH phenotype comprising of at least lipid accumulation, fibrosis, hepatocellular ballooning, a microvesicular steatosis, a macrovesicular steatosis, and inflammation can be induced with the bioprinted liver tissue constructs using the methods disclosed in this invention.

And, Examples 10-11, as shown in FIGS. 25-34, demonstrate, for example, that the models exhibit key features of NAFLD/NASH patient phenotypes including combinations of clinical histopathology, fold increases of TG accumulation, lipotoxicity, increased inflammation, hepatocellular injury, and increased fibrosis.

Example 12

Bioprinted Liver Tissues Prepared from Different Donors for Modeling of NAFLD (NASH)

FIGS. 35-39 show that a NASH phenotype can be achieved in bioprinted liver tissue constructs using cells from different donors.

Figure 35:
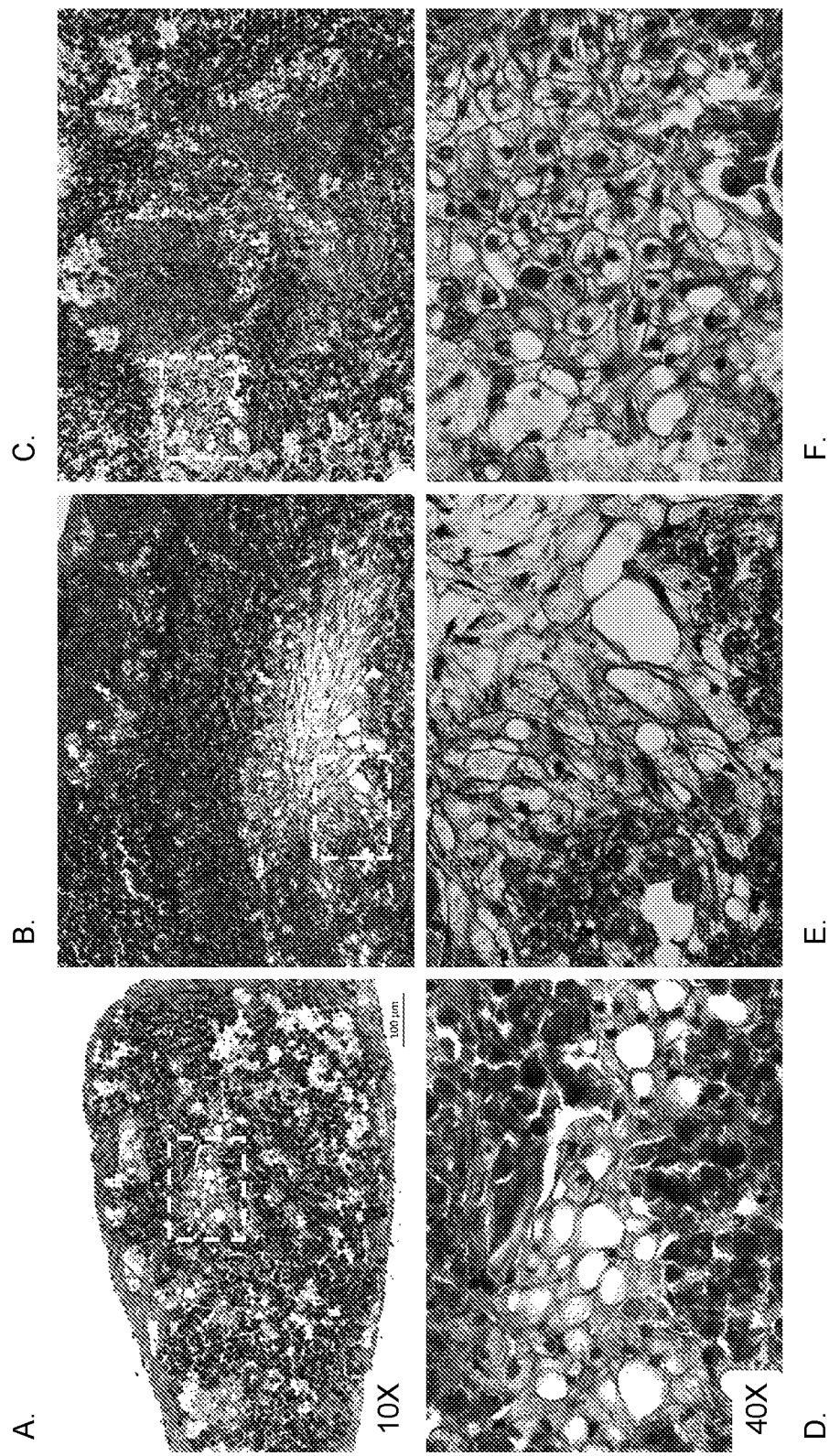
FIG. 35 depicts histological characterizations (TCM staining) of non-limiting examples of three-dimensional, engineered, bioprinted liver tissue constructs induced to exhibit a NASH phenotype prepared using hepatocytes from different donors. (A)-(C) show 10× magnifications of liver tissue constructs prepared using hepatocytes from Donors 1-3, respectively. (D)-(F) show 40× magnifications of the same tissues from Donors 1-3, respectively.
Figure 36:
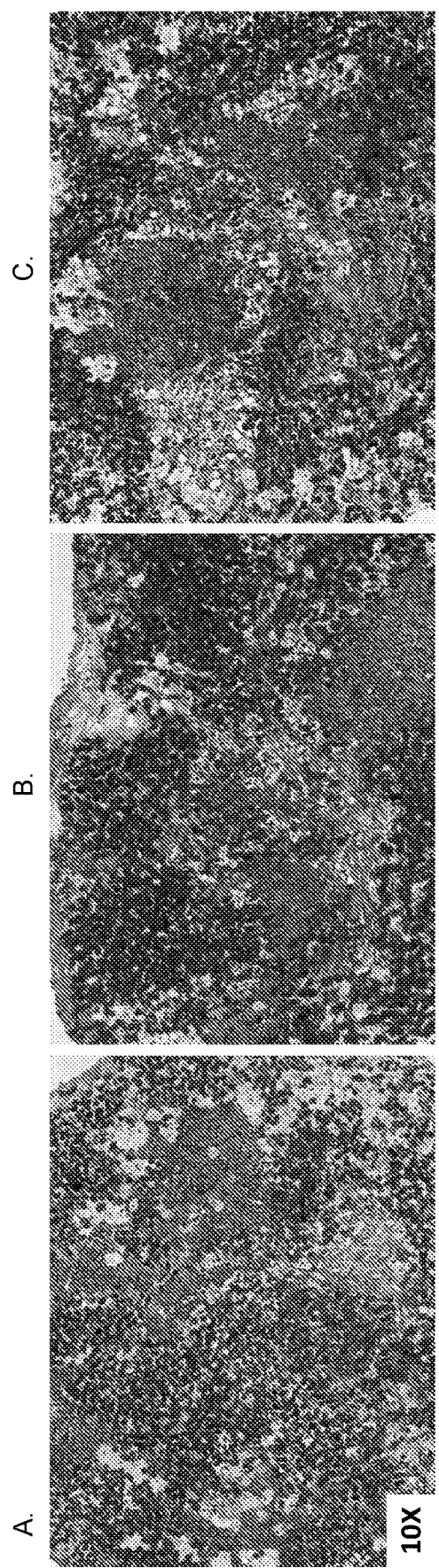
FIG. 36 depicts histological characterizations (TCM staining) of non-limiting examples of three-dimensional, engineered, bioprinted liver tissue constructs induced to exhibit a NASH phenotype. prepared using hepatocytes from different donors. (A)-(C) show 10× magnifications of liver tissue constructs prepared using hepatocytes from Donors 5, 4, and 3, respectively.
Figure 37:
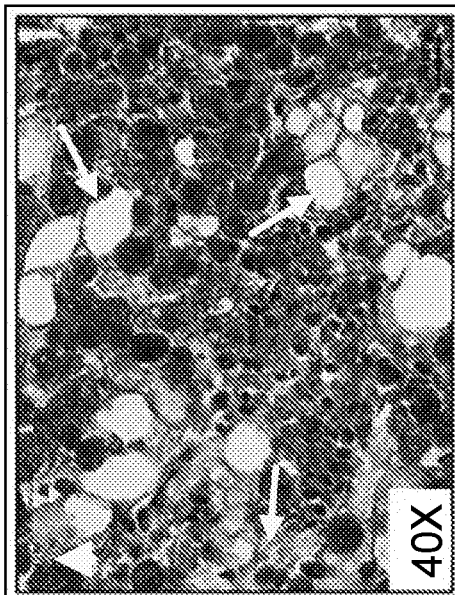
FIG. 37 is a non-limiting, exemplary demonstration of NASH induction in bioprinted human liver tissues prepared using Kupffer cells from different donors. (A)-(D) show magnification of bioprinted tissue using Kupffer cells from a first donor ((A)-(B)) or a second donor ((C)-(D)) at 10× ((A) and (C)) and 40× ((B) and (D)) magnification. Macrovesicular steatosis is indicated by rightmost arrows in (B) and the two uppermost arrows in (D). Microvesicular steatosis is indicated by arrowheads in (B) and (D). Fibrosis is indicated by the leftmost arrow in (B) and the bottommost two arrows in (D).
Figure 37:
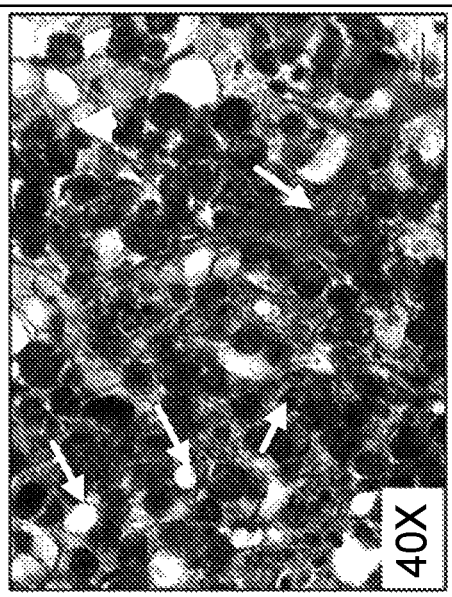
Figure 37:
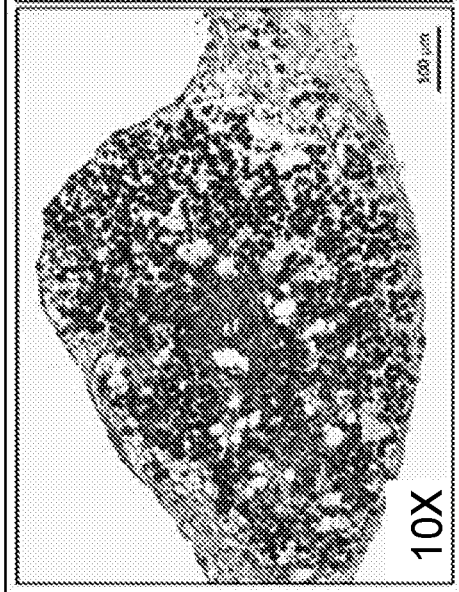
Figure 37:
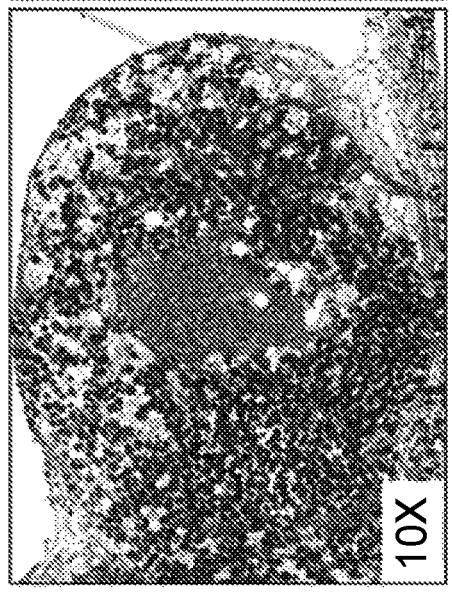

Bioprinted liver tissue constructs were prepared using hepatocytes from different donors without liver disease (i.e., Donors 1-5). FIGS. 35(A)-(C) show that a NASH phenotype, including steatosis and fibrosis, was induced with fructose (12.5 mM) and PA (500 uM) in tissue constructs prepared using hepatocytes from Donors 1-3, respectively. FIGS. 35(A)-(C) show tissues at 10× magnification. FIGS. 35(D)-(F) correspond to tissues (A)-(C), respectively, at 40× magnification. FIGS. 36(A)-(C) show tissues from Donors 5, 4, and 3, respectively, treated for NASH induction as described for FIG. 35. Evaluation of the multiple donors revealed that cells from different hepatocyte donors exhibit a differential propensity for NASH induction. See FIG. 36.

Figure 38:
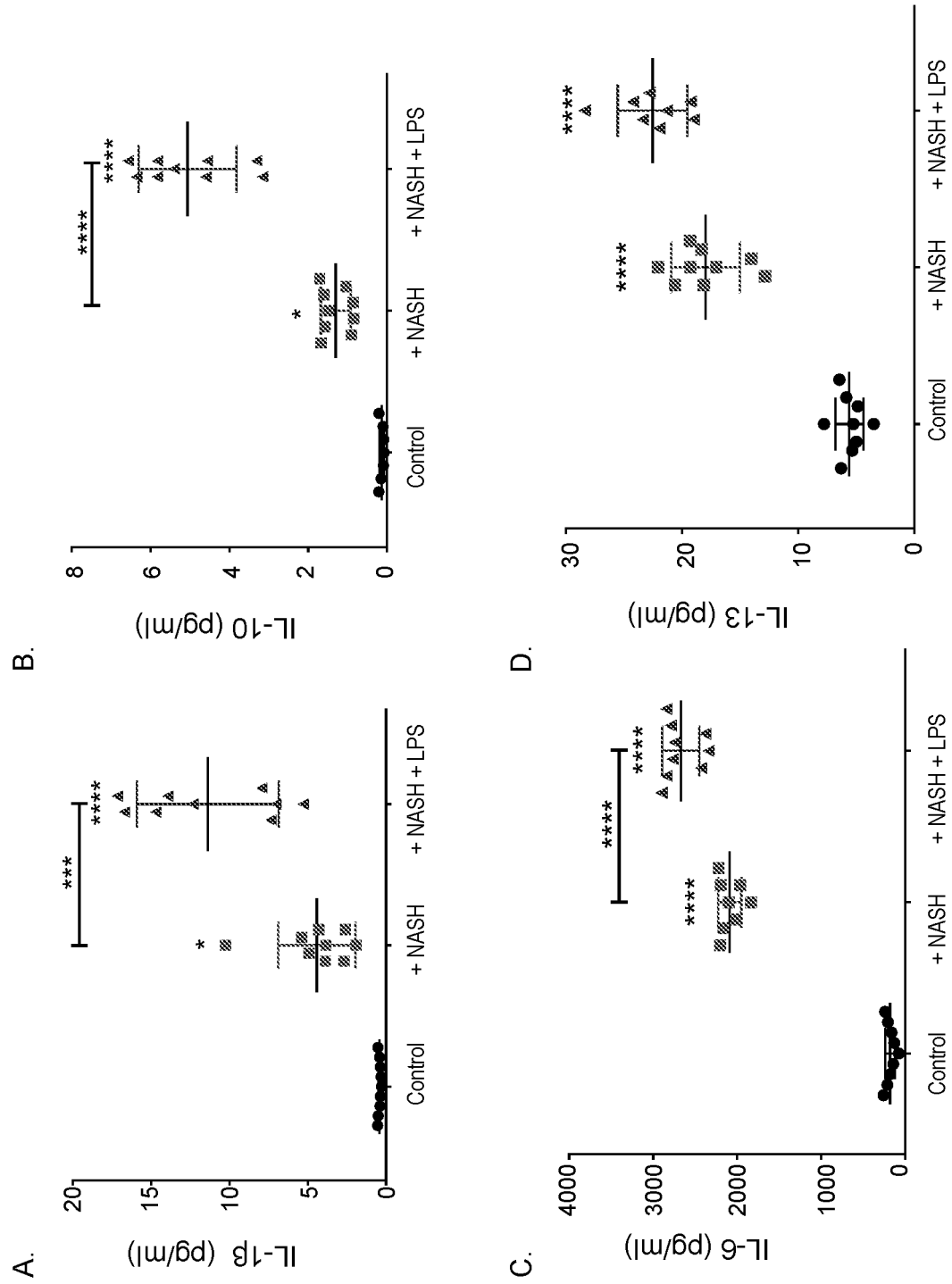
FIG. 38 shows cytokine release in bioprinted human liver tissues prepared using Kupffer cells from the first donor in FIG. 37. (A)-(D) show release of IL-1β, IL-10, IL-6, and IL-13, respectively, in picograms per milliliter (pg/ml) for bioprinted tissues prepared with Kupffer cells from the first donor following 14 days without any treatment (Control), after treatment for NASH induction as described for FIG. 37 (+NASH), and after co-treatment of LPS with NASH induction by (+NASH+LPS).
Figure 39:
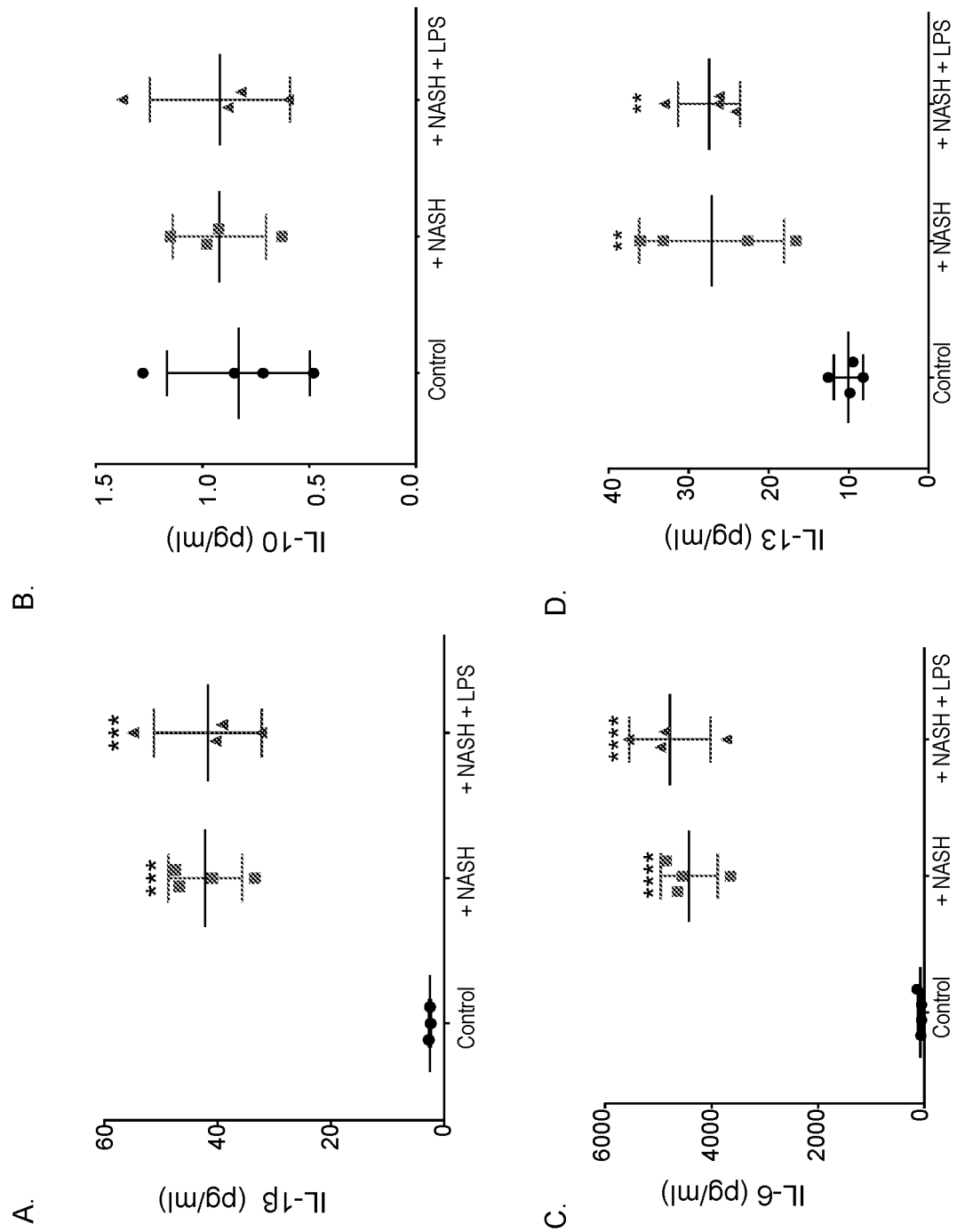
FIG. 39 shows cytokine release in bioprinted human liver tissues prepared using Kupffer cells from the second donor in FIG. 37. (A)-(D) show release of IL-1β, IL-10, IL-6, and IL-13, respectively, in picograms per milliliter (pg/ml) for bioprinted tissues prepared with Kupffer cells from the first donor following 14 days without any treatment (Control), after treatment for NASH induction as described for FIG. 37 (+NASH), and after co-treatment of LPS with NASH induction (+NASH+LPS).

Bioprinted liver tissues constructs were also prepared according to Example 6 but using Kupffer cells from different donors without liver disease. FIGS. 37(A) and (C) show that a NASH phenotype, including steatosis (macro- and microvesicular) and fibrosis, was induced with fructose (12.5 mM) and PA (500 uM) in immune competent tissue constructs prepared using Kupffer cells from a first donor ((A)-(B)) or a second donor ((C)-(D)) at 10× ((A) and (C)) and 40× ((B) and (D)) magnification. Macrovesicular steatosis is indicated by the two rightmost arrows in FIG. 37(B) and the two uppermost arrows in FIG. 37(D). Microvesicular steatosis is indicated by arrowheads in FIGS. 37(B) and (D). Fibrosis is indicated by the leftmost arrow in FIG. 37(B) and the bottommost two arrows in FIG. 37(D). FIGS. 38 and 39 show that inflammatory cytokine release (i.e., IL-1β, IL-6, and IL-13) was significantly increased by NASH induction following 14 days of treatment with 12.5 mM fructose and 500 uM PA (+NASH) or treatment with 12.5 mM fructose, 500 uM PA, and 10 µg/ml LPS (+NASH+LPS), versus untreated controls, using constructs prepared from either the first (FIG. 38) or second (FIG. 39) donor. In contrast, release of the anti-inflammatory cytokine IL-10 was different between the donors.

Significantly, FIGS. 35-39 show that the methods of inducing NASH in bioprinted liver tissue constructs, as disclosed in this invention, were robust and effective across different donors of cells.

Example 13

Bioprinted Liver Tissues for Assessing Drug Efficacy and Toxicity

Figure 40:
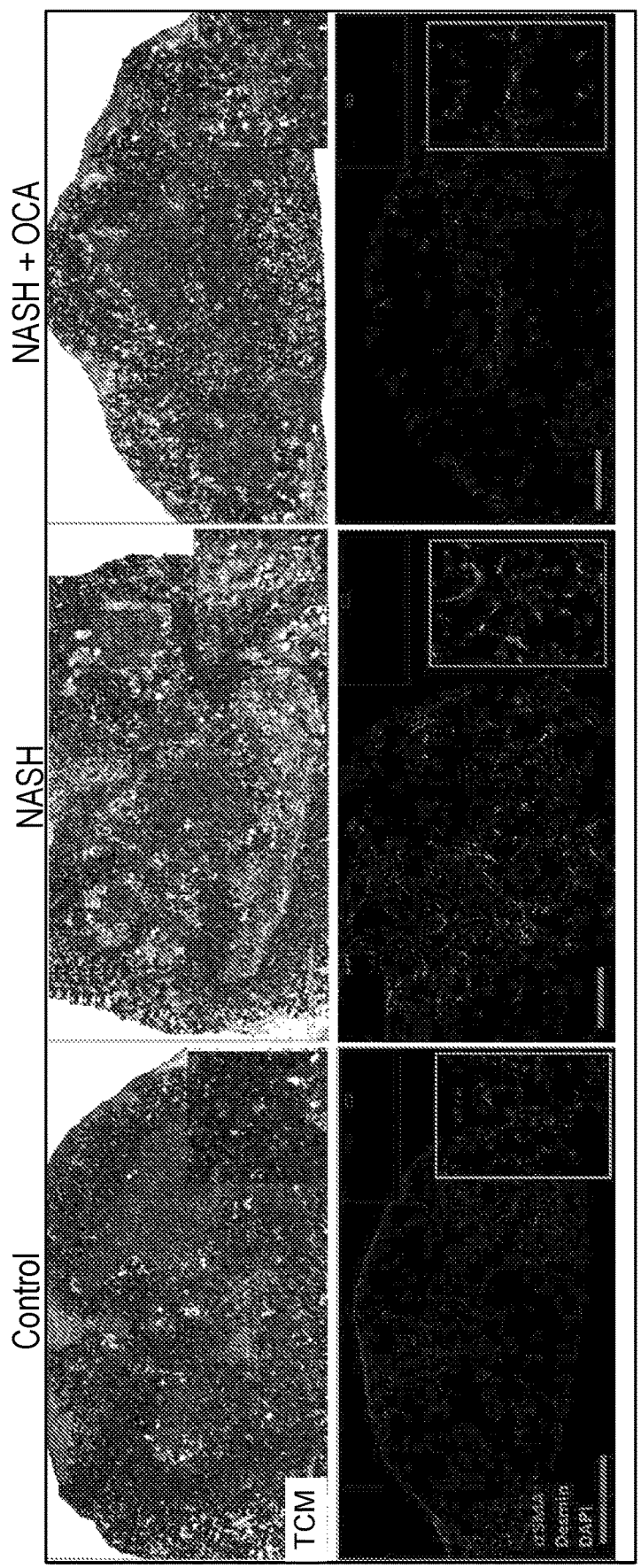
FIG. 40 depicts histological characterizations and different induction and modulation methods of non-limiting examples of three-dimensional, engineered, bioprinted liver tissue constructs induced to exhibit a NASH phenotype.

The assessment of drug efficacy in the bioprinted liver tissue constructs exhibiting a NASH phenotype was investigated. The top panel of FIG. 40 shows that NASH-induced (12.5 mM fructose and 500 uM PA) bioprinted liver tissue constructs treated with the FXR agonist, Obeticholic Acid (OCA), exhibited a reduction in steatosis and fibrosis (stained blue via Trichrome; TCM), and the bottom row shows a reduction stellate cell activation (stained red via alpha-smooth muscle actin; αSMA). The figure shows that protection against disease progression was achieved upon co-administration of OCA, providing proof of concept for application of the NASH model in drug efficacy assessments.

Figure 41:
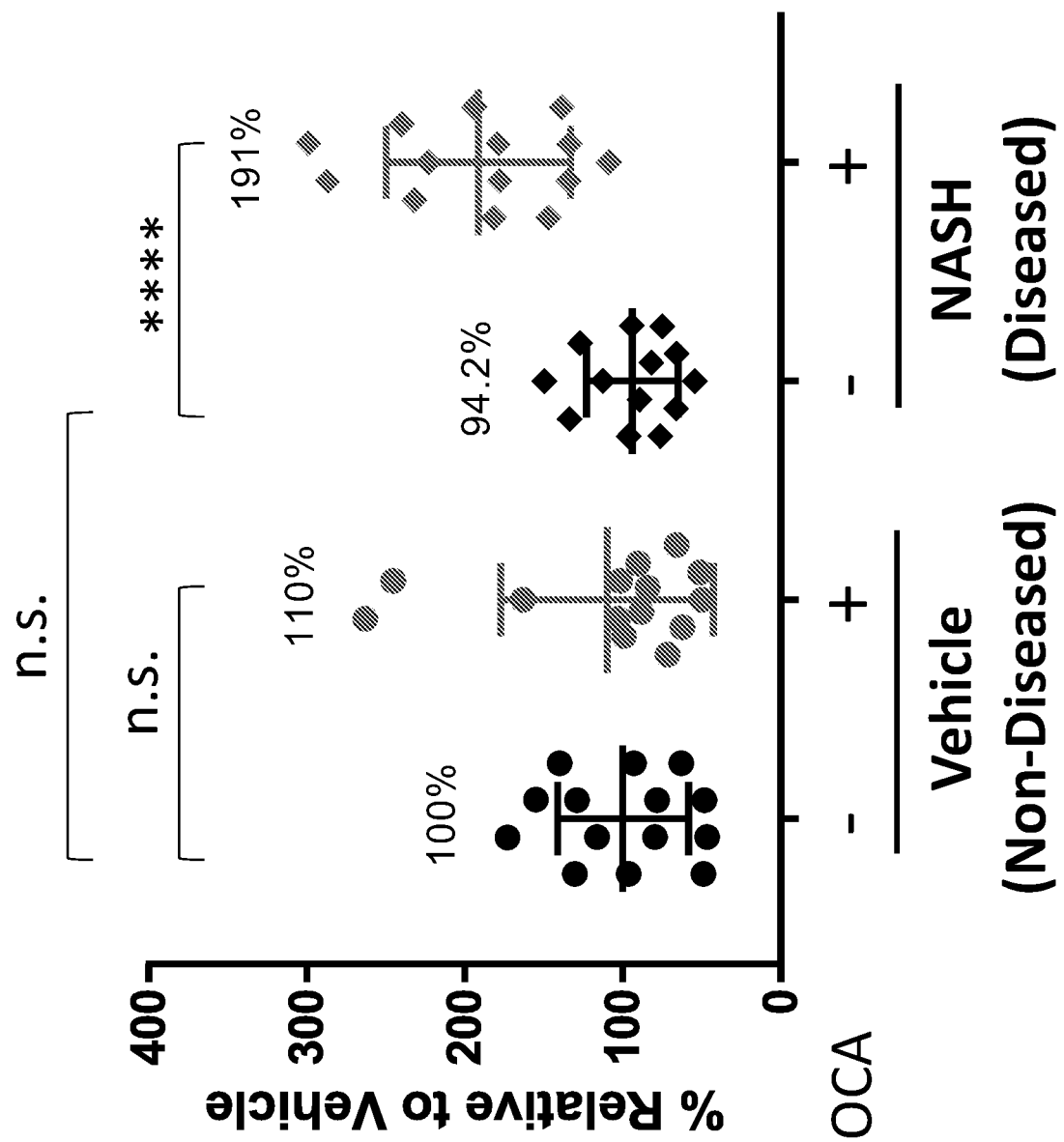
FIG. 41 is a graph showing percentage of alanine transferase (ALT) release relative to vehicle in non-diseased (vehicle-treated) or diseased (NASH-induced) bioprinted liver tissues treated with (+) or without (−) OCA. n. s.=not significant; ****=P<0.0001.

The assessment of drug safety was also investigated using the bioprinted liver tissue constructs. Non-diseased (vehicle-treated) or diseased (NASH-induced with 12.5 mM fructose and 500 uM PA) bioprinted liver tissues were treated with OCA, followed by measurement of alanine transferase (ALT) in the culture medium, a liver enzyme elevated with hepatocellular injury. As shown in FIG. 41, a significant increase in sensitivity, as shown by increased ALT, was observed in diseased tissue following treatment with OCA versus in non-diseased tissue. Significance was determined by One-way ANOVA with Dunnets Multiple Comparisons Test, with the increase in ALT levels for diseased tissue following OCA treatment having a $P<0.0001$ as compared to diseased tissue without OCA treatment. This provides a proof of concept for application of the NASH model in assessment of differential toxicity.

Example 14

Bioprinted Liver Tissue for Modeling of NAFLD (NASH)

Figure 42:
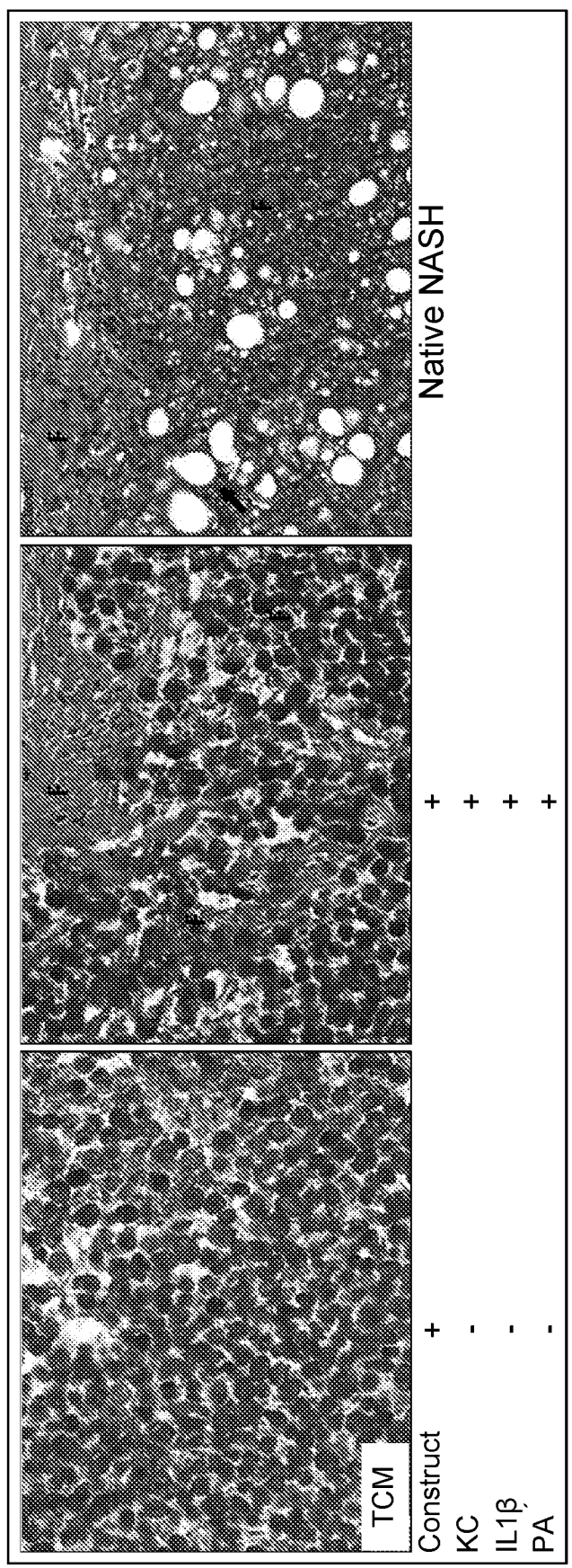
FIG. 42 depicts histological characterizations (TCM staining) of non-limiting examples of three-dimensional, engineered, bioprinted liver tissue constructs induced to exhibit a NASH phenotype with PA and co-treatment of PA with IL1-0. KC=Kupffer cells; Native NASH=a native human liver tissue exhibiting NASH.

Bioprinted liver tissue constructs, similar to the Example 6 bioprinted liver tissue constructs, were treated with 21 days of PA (0.5 mM) and IL113 (100 ng/mL). As depicted in FIG. 42, following 21 days of PA (0.5 mM) and inflammatory cytokines IL1β (100 ng/mL) treatment, immune competent bioprinted liver tissue constructs displayed increased fibrosis when compared to untreated controls. Significantly, Example 14, as provided in FIG. 42, demonstrates that a NASH phenotype comprising of at least lipid accumulation (steatosis) and fibrosis can be achieved in bioprinted liver tissue constructs.

Example 15

Bioprinted Liver Tissue for Modeling of NAFLD (NASH)

Figure 43:
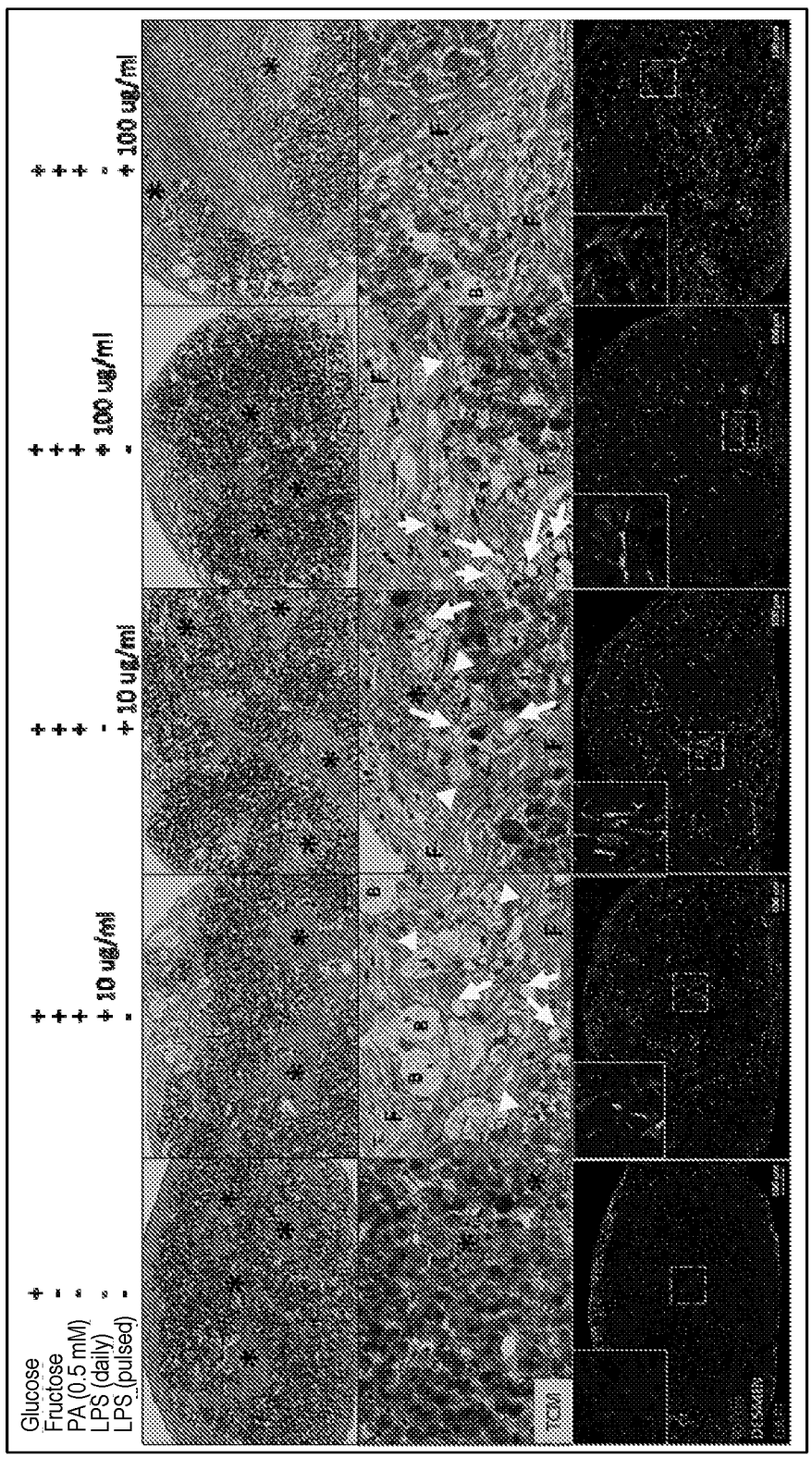
FIG. 43 depicts histological characterizations (top two rows, TCM staining; bottom row, α-smooth muscle actin (α-SMA) immunofluorescence) of non-limiting examples of three-dimensional, engineered, bioprinted liver tissue constructs induced to exhibit a NASH phenotype. *=non-parenchymal cell rich regions; F=fibrosis; arrowhead=microvesicular steatosis; arrow=macrovesicular steatosis; B=hepatocellular ballooning.

Bioprinted liver tissue constructs, similar to the Example 6 bioprinted liver tissue constructs, were treated with 21 days of PA and fructose (12.5 mM), and constitutive 10 ug/mL LPS, pulsed 10 ug/mL LPS, constitutive 100 ug/mL LPS, or pulsed 100 ug/mL LPS treatment. As depicted in FIG. 43, these treated bioprinted liver tissue constructs displayed comparable hepatic stellate cells (HSC) activation (αSMA expression) and subsequent degrees of fibrosis (F), micro (see arrowhead in FIG. 43) and macrovesicular (arrow in FIG. 43) steatosis when compared to controls. Tissues treated constitutively with 100 ug/mL LPS displayed a high degree of fibrosis with putative hepatocellular ballooning (B), which was also observed in the constitutive 10 ug/mL LPA treatment vs. controls. In FIG. 43, * denotes NPC rich regions. Significantly, Example 15, as shown in FIG. 43, demonstrates that a NASH phenotype comprising of at least lipid accumulation (steatosis), microvesicular steatosis, macrovesicular steatosis, hepatocellular ballooning, and fibrosis can be achieved in bioprinted liver tissue constructs.

Example 16

Figure 44:
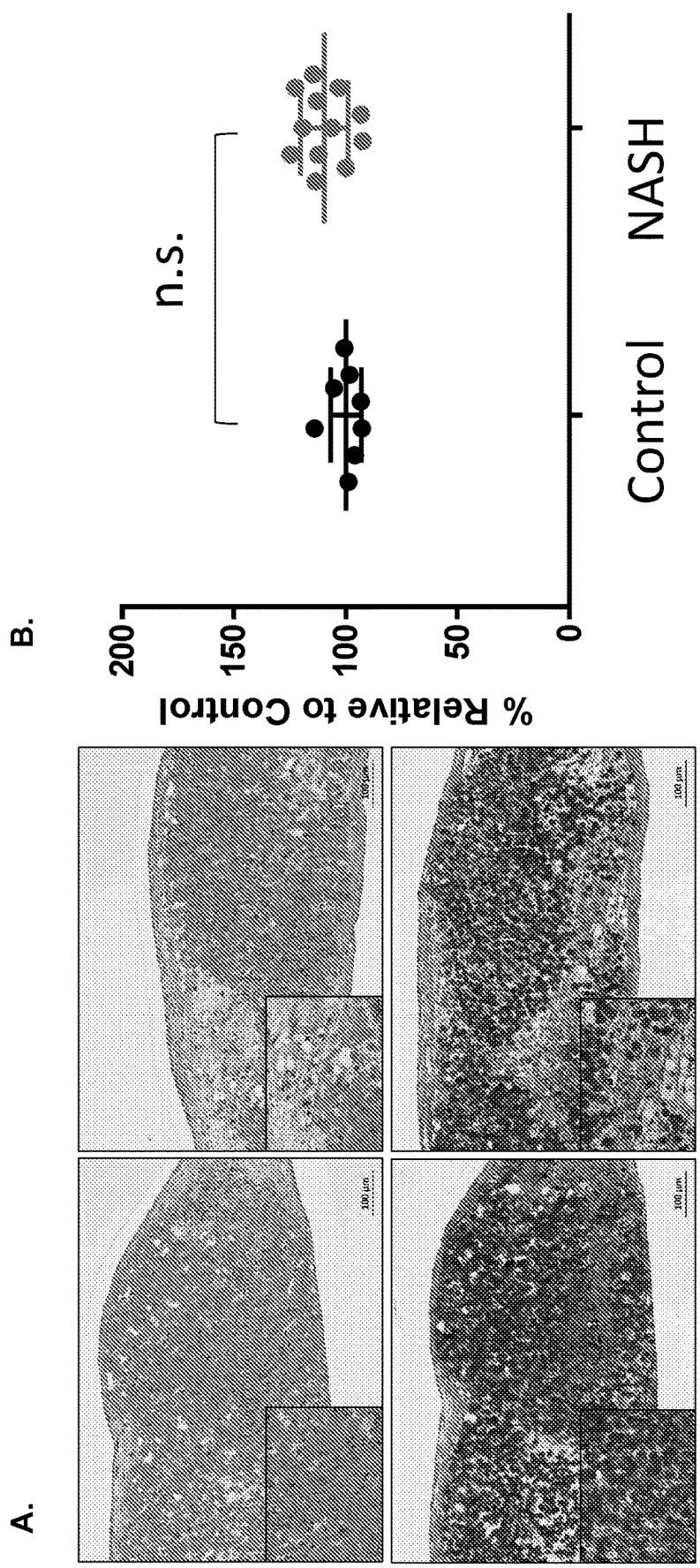
FIG. 44 depicts histological characterizations (A) and analysis of urea production (B) in control and NASH-induced bioprinted liver tissues. (A) shows H&E staining in the top row and Trichrome staining in the bottom row. (B) shows percentages of urea produced relative to control.

Induction of Disease in Bioprinted Liver Tissue does not Adversely Affect Tissue Health The health of NASH-induced tissues as compared to control tissues was investigated. Urea is a waste product produced in the liver, plays a key role in protein catabolism and removal of toxic ammonia, and is commonly used as an indicator of liver health and function. FIG. 44 shows that NASH induction (12.5 mM Fructose+200 µM OA+300 µM PA) did not adversely affect tissue health, as demonstrated by the absence of overt tissue toxicity by histological examination via H&E (A, top row) and Trichrome (A, bottom row) staining. Lack of any adverse effect on tissue health was also demonstrated by absence of any significant different between levels of urea production between for and NASH-induced tissues (B) as determined by one-way ANOVA with Tukey's multiple comparison test.

Example 17

Figure 45:
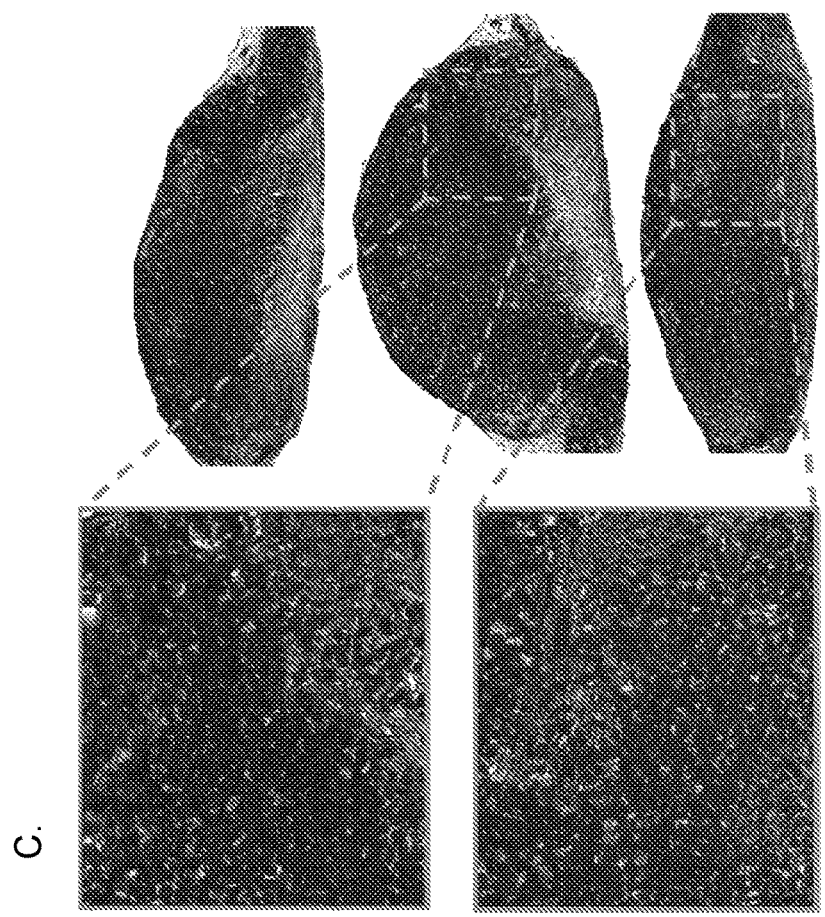
FIG. 45 shows donor tissue and bioprinted liver tissues prepared from the donor tissue. (A) shows tissue from the donor with a fibrotic phenotype as indicated within the dashed square and an expanded view. (B) is a diagram showing the combination of cell types from the donor. HEP=primary hepatocytes from non-diseased tissue; SC, EC, and KC=hepatic stellate cells, liver endothelial cells, and Kupffer cells, respectively, from diseased tissue. (C) shows three independent replicates of liver tissue constructs that were bioprinted from the combination of donor cells and allowed to mature, demonstrating fibrotic phenotypes in each. The fibrotic phenotypes are indicated within the dashed squares and in expanded views for two of the tissues.
Figure 45:
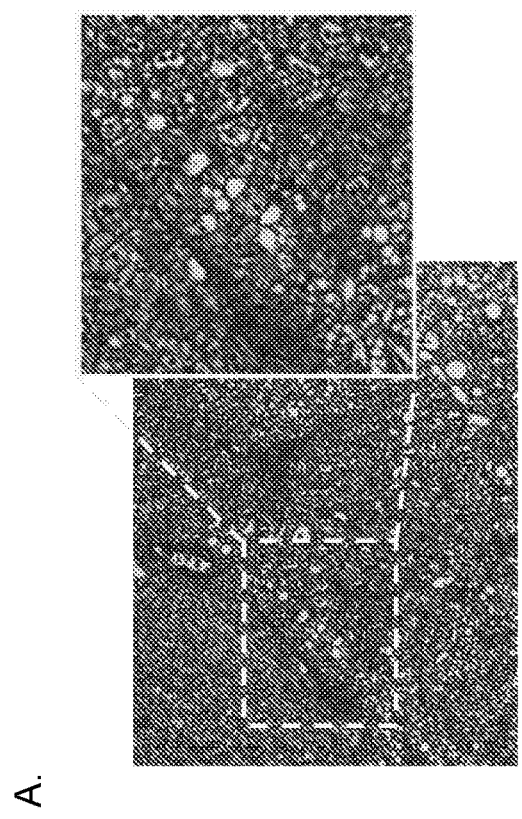
Figure 45:
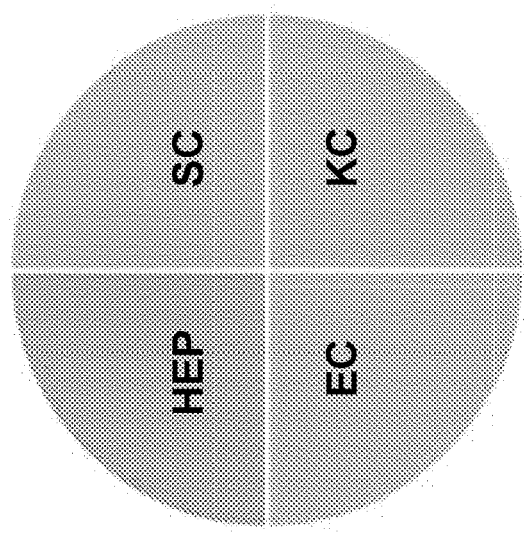

Bioprinted Liver Tissues from Diseased Donors Retain and Re-Establish Pathogenic Features In Vitro Primary hepatocytes from non-diseased tissue as well as hepatic stellate cells, liver endothelial cells, and Kupffer cells from diseased tissue were collected from a single human donor with liver disease and combined. Bioprinted liver tissues were produced from the combined cells according to procedures described in Example 6 and allowed to mature. FIG. 45(A) shows tissue from the donor with a fibrotic phenotype as indicated within the dashed square and an expanded view. The combination of cells from the donor is shown in FIG. 45(B). The right side of FIG. 45(C) shows three independent replicates of liver tissue constructs that were bioprinted from the combination of donor cells and allowed to mature. The left side of FIG. 45(C) shows expanded views of two of the tissues. Hepatic stellate cells in the bioprinted cells were activated, and fibrogenesis initiated and progressed without the addition of any exogenous stimuli such as TGF-β. This showed, and also provides a proof of concept, that disease donor origin cells retain and re-establish pathogenic features after isolation in bioprinted liver tissues. This also demonstrated that combining non-diseased vs. disease-origin cells in a chimeric fashion could make it possible to determine which cell type(s) are responsible for specific pathogenic mechanisms.

Example 18

Bioprinted Liver Tissue for Discovery and Validation of Disease Biomarkers

Figure 46:
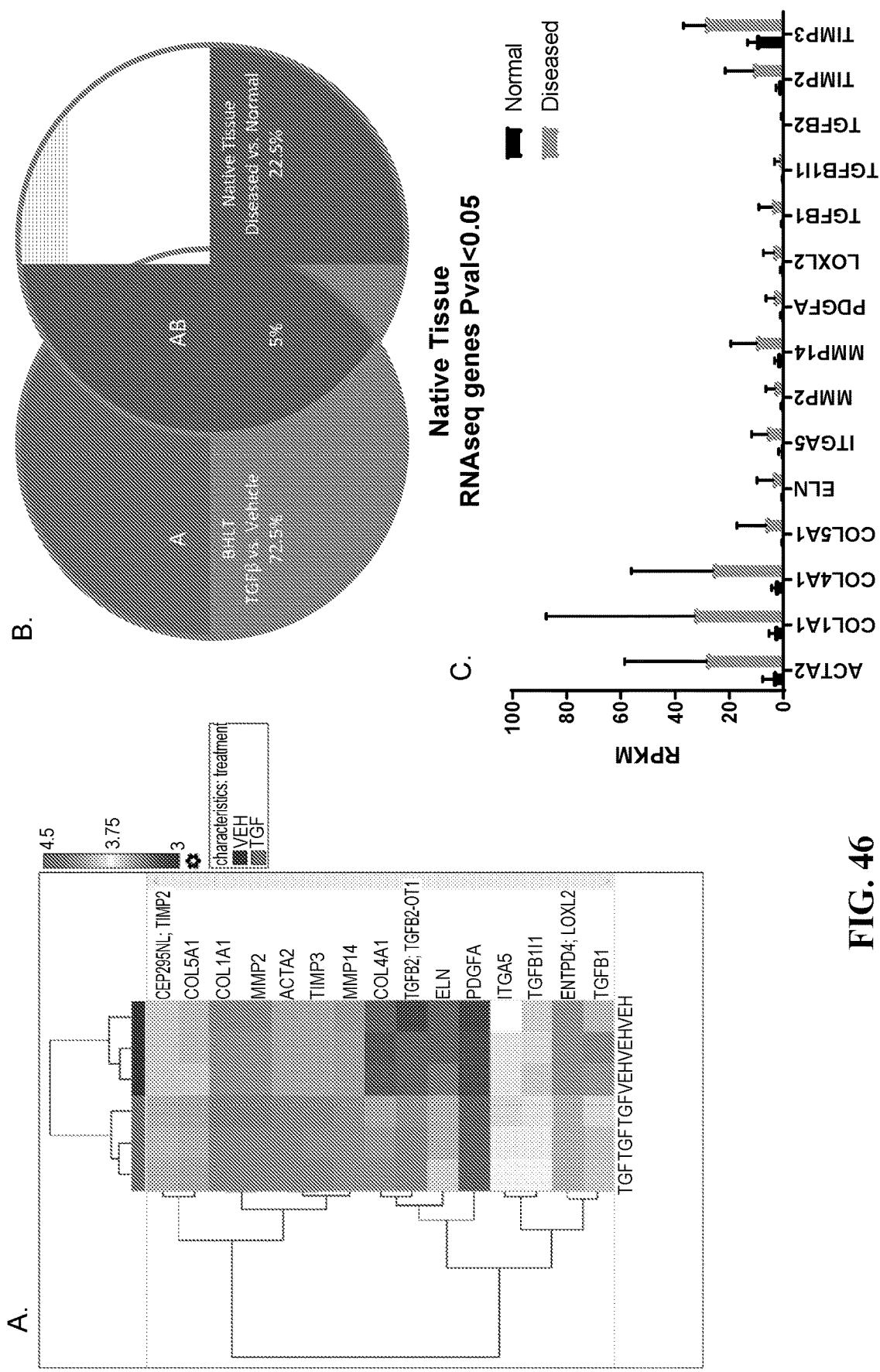
FIG. 46 shows analyses of expression profiles of exemplary disease-associated genes. (A) shows microarray data indicating differences in the expression profile of disease-associated genes by bioprinted human liver tissues after treatment with TGF-$\beta$ ("TGF") as compared to a vehicle control ("VEH"). (B) is a Venn diagram showing the percentages of genes that were significantly modulated in the comparison of bioprinted human liver tissues ("BHLT") treated with TGF-$\beta$ versus vehicle control as well as in the comparison of NASH confirmed ("Diseased") versus healthy ("Normal") tissues collected from human subjects ("Native Tissue"). (C) shows a bar graph of exemplary significantly modulated genes from "AB" in the Venn diagram of (B) for diseased versus normal tissues collected from human subjects as determined by RNAseq analysis.

Bioprinted human liver tissues were treated for 14 days with either TGF-β to elicit a tissue-specific response (e.g., fibrosis) or a vehicle control. RNA was collected and used for microarray analysis according to standard procedures. FIG. 46(A) shows differences observed in the expression profile of exemplary disease-associated genes by bioprinted human liver tissues after treatment with TGF-β ("TGF") as compared to a vehicle control ("VEH"), indicating biomarkers associated with tissue specific responses induced by TGF-β.

In another comparison, a set of five healthy and five confirmed NASH tissues were collected from human subjects. RNA was isolated, and RNAseq analysis was performed according to standard procedures to identify genes that were modulated (i.e., increased or decreased expression) between the healthy and diseased tissues.

FIG. 46(B) shows a venn diagram of the percentage of genes that were significantly modulated in the comparison of bioprinted human liver tissues ("BHLT") treated with TGF-β versus vehicle control as well as in the comparison of NASH confirmed ("Diseased") versus healthy ("Normal") tissues collected from human subjects ("Native Tissue"). The Venn diagram indicates that the expression of 72.5% of genes were significantly modulated in the BHLT TGF-β versus vehicle comparison ("A") and 22.5% were significantly modulated in the native tissue diseased versus normal comparison ("B"), while 5% of the significantly modulated genes were identical between both comparisons ("AB"). For a gene to be considered as "significantly modulated" required at least a minimal level of expression in each comparison tissue as well as a $P<0.05$ for the differences in gene expression between the comparison tissues.

FIG. 46(C) shows a bar graph of exemplary significantly modulated genes from "AB" in the Venn diagram for diseased versus normal tissues collected from human subjects as determined by RNAseq analysis.

This showed, and also provides a proof of concept, that bioprinted liver tissues as described herein can be used to identify biomarkers associated with disease phenotypes of liver disorders and that such biomarkers can be validated by comparison to native tissues. Identification of biomarkers in this manner can also provide putative drug targets for treatment of the disorders.

In summary, the liver disorder models offers a safe, economical, and clinically relevant platform to aid in the discovery of novel therapeutics to treat the condition. These liver disorder models can also be used for the identification of liver-specific biomarkers that can be easily measured noninvasively to diagnose and assess the severity of NAFLD. These models will thereby bridge the costly gap between rodent testing and clinical trials where in the later most drugs fail due to lack of efficacy and/or toxicity.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

All patents, patent applications and publications cited herein are fully incorporated by reference herein.

What is claimed is:

1. A culture comprising a three-dimensional, engineered, bioprinted, biological liver tissue construct and a culture medium, wherein the liver tissue construct comprises parenchymal cells and non-parenchymal cells, the parenchymal cells comprising hepatocytes and the non-parenchymal cells comprising endothelial cells and hepatic stellate cells, and wherein the culture medium comprises: a palmitic acid, an oleic acid, or a combination thereof in a concentration that is capable of inducing a nonalcoholic steatohepatitis (NASH) phenotype in the liver tissue construct, and wherein the liver tissue construct comprises the NASH phenotype comprising a lipid accumulation, a hepatocellular ballooning, a macrovesicular steatosis, and a histological fibrosis induced by the palmitic acid, oleic acid, or combination thereof.

2. The culture of claim 1, wherein the culture medium further comprises a fructose.

3. The culture of claim 2, wherein the liver tissue construct further comprises Kupffer cells.

4. The culture of claim 3, wherein the phenotype further comprises an inflammation.

5. The culture of claim 1, wherein the liver tissue construct further comprises adipocytes.

6. The culture of claim 1, wherein the liver tissue construct comprises at least one compartment comprising an interior defined by a border, the interior comprising the parenchymal cells, and the border comprising the non-parenchymal cells.

7. The culture of claim 6, wherein the liver tissue construct further comprises a second border surrounding the border that defines the interior, the second border comprising adipocytes.

8. The culture of claim 6, wherein the compartment is defined by a planar geometry.

9. The culture of claim 1, wherein the liver tissue construct comprises a laminar geometry, and wherein a first layer comprises the non-parenchymal cells and a second layer comprises the parenchymal cells.

10. The culture of claim 9, wherein the liver tissue construct further comprises a third layer of non-parenchymal cells, wherein the first layer is below the second layer, and the second layer is below the third layer.

11. The culture of claim 1, wherein the culture medium further comprises a fatty acid uptake enhancer.

12. The culture of claim 11, wherein the fatty acid uptake enhancer is genipin.

13. A three-dimensional, engineered, bioprinted biological model of a liver disorder, wherein the model comprises the liver tissue construct from the culture of claim 1, wherein the liver tissue construct comprises an induced the NASH phenotype induced by the palmitic acid, oleic acid, or combination thereof.

14. The model of claim 13, wherein the liver tissue construct further comprises Kupffer cells.

15. The model of claim 14, wherein the phenotype further comprises an inflammation.

* * * * *

UNITED STATES PATENT AND TRADEMARK OFFICE
CERTIFICATE OF CORRECTION

PATENT NO. : 12,252,712 B2
APPLICATION NO. : 16/500521
DATED : March 18, 2025
INVENTOR(S) : Deborah Lynn Greene Nguyen et al.

Page 1 of 1

It is certified that error appears in the above-identified patent and that said Letters Patent is hereby corrected as shown below:

In the Claims

In Column 92, Claim 13, Line 33, delete "comprises an induced the NASH" and insert --comprises the NASH--, therefor.

Signed and Sealed this
Sixteenth Day of September, 2025

Coke Morgan Stewart
*Acting Director of the United States Patent and Trademark Office*